(12) United States Patent
Nuccio et al.

(10) Patent No.: US 12,270,036 B2
(45) Date of Patent: *Apr. 8, 2025

(54) INIR6 TRANSGENIC MAIZE

(71) Applicant: INARI AGRICULTURE TECHNOLOGY, INC., Cambridge, MA (US)

(72) Inventors: Michael Lee Nuccio, Salem, NH (US); Joshua L. Price, Raleigh, NC (US); Michael Andreas Kock, Rheinfelden (DE)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 266 days.

This patent is subject to a terminal disclaimer.

(21) Appl. No.: 17/644,157

(22) Filed: Dec. 14, 2021

(65) Prior Publication Data

US 2022/0098602 A1 Mar. 31, 2022

Related U.S. Application Data

(63) Continuation of application No. 17/249,640, filed on Mar. 8, 2021, now Pat. No. 11,214,811.

(60) Provisional application No. 63/199,951, filed on Feb. 4, 2021, provisional application No. 63/199,930, filed on Feb. 3, 2021, provisional application No. 63/059,813, filed on Jul. 31, 2020, provisional application No. 63/059,963, filed on Jul. 31, 2020, provisional application No. 63/059,916, filed on Jul. 31, 2020, provisional application No. 63/059,860, filed on Jul. 31, 2020.

(51) Int. Cl.
*C12N 15/82* (2006.01)

(52) U.S. Cl.
CPC ...... *C12N 15/8213* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 7,632,985 B2 | 12/2009 | Malven et al. | |
| 8,232,456 B2 | 7/2012 | Long et al. | |
| 8,450,561 B2 | 5/2013 | Beazley et al. | |
| 8,501,407 B2 | 8/2013 | Brinker et al. | |
| 8,575,434 B2 * | 11/2013 | Diehn | C12Q 1/6895 426/655 |
| 8,680,363 B2 | 3/2014 | Bard et al. | |
| 9,447,428 B2 | 9/2016 | Brinker et al. | |
| 9,540,655 B2 | 1/2017 | Cui et al. | |
| 9,738,904 B2 | 8/2017 | Cui et al. | |
| 9,944,944 B2 | 4/2018 | Cui et al. | |
| 11,041,172 B2 | 6/2021 | Cermak | |
| 11,214,811 B1 * | 1/2022 | Nuccio | A01H 5/10 |
| 11,242,534 B1 | 2/2022 | Nuccio et al. | |
| 11,326,177 B2 | 5/2022 | Price et al. | |
| 11,359,210 B2 | 6/2022 | Price et al. | |
| 11,369,073 B2 | 6/2022 | Price et al. | |
| 2010/0275286 A1 | 10/2010 | Wu et al. | |
| 2011/0191877 A1 | 8/2011 | Russel et al. | |
| 2011/0191899 A1 | 8/2011 | Ainley et al. | |
| 2013/0212747 A1 | 8/2013 | Cui et al. | |
| 2013/0296170 A1 | 11/2013 | Hanger et al. | |
| 2013/0324408 A1 | 12/2013 | Cui et al. | |
| 2013/0333071 A1 | 12/2013 | Boukharov et al. | |
| 2014/0041083 A1 | 2/2014 | Cui et al. | |
| 2015/0059010 A1 | 2/2015 | Cigan et al. | |
| 2015/0082478 A1 | 3/2015 | Cigan et al. | |
| 2016/0029631 A1 | 2/2016 | Hellwege et al. | |
| 2017/0166912 A1 | 6/2017 | Brower-Toland et al. | |
| 2018/0163218 A1 | 6/2018 | Corbin et al. | |
| 2019/0136249 A1 | 5/2019 | Sakai et al. | |
| 2019/0352655 A1 | 11/2019 | Niu et al. | |
| 2020/0157554 A1 | 5/2020 | Cigan et al. | |
| 2020/0208172 A1 | 7/2020 | Ikeda et al. | |
| 2020/0399626 A1 | 12/2020 | Liu et al. | |
| 2022/0030806 A1 | 2/2022 | Price et al. | |
| 2022/0030822 A1 | 2/2022 | Nuccio et al. | |
| 2022/0033836 A1 | 2/2022 | Price et al. | |
| 2022/0154194 A1 | 5/2022 | Nuccio et al. | |
| 2022/0251584 A1 | 8/2022 | Nuccio et al. | |
| 2022/0364105 A1 | 11/2022 | Price et al. | |
| 2023/0077473 A1 | 3/2023 | Price et al. | |

(Continued)

FOREIGN PATENT DOCUMENTS

| | | | |
|---|---|---|---|
| WO | 2022026375 A1 | 2/2022 | |
| WO | 2022026379 A1 | 2/2022 | |

(Continued)

OTHER PUBLICATIONS

Bortesi et al., "The CRISPR/Cas9 system for plant genome editing and beyond", Biotechnology Advances, vol. 33, pp. 41-52, Dec. 16, 2014.
Cho et al., "Nonallelic homologous recombination events responsible for copy No. variation within an RNA silencing locus", Plant Direct, vol. 3, 16 pages, Aug. 5, 2019.
Luo et al., "Improperly Terminated, Unpolyadenylated mRNA of Sense Transgenes is Targeted by RDR6-Mediated RNA Silencing in *Arabidopsis*", The Plant Cell, vol. 19, pp. 943-958, Mar. 2007.
Srivastava et al., "Gene Stacking by recombinases", Plant Biotechnology Journal, vol. 14, pp. 471-482, 2016.
Xing et al., "Revealing frequent alternative polyadenylation and widespread low-level transcription read-through of novel plant transcription terminators", Plant Biotechnology Journal, vol. 8, pp. 772-782, 2010.

(Continued)

*Primary Examiner* — Matthew R Keogh
(74) *Attorney, Agent, or Firm* — McKee, Voorhees & Sease, PLC

(57) ABSTRACT

Transgenic INIR6 maize plants comprising modifications of the DP-4114 maize locus which provide for facile excision of the modified DP-4114 transgenic locus or portions thereof, methods of making such plants, and use of such plants to facilitate breeding are disclosed.

9 Claims, 26 Drawing Sheets

Figure 1D:
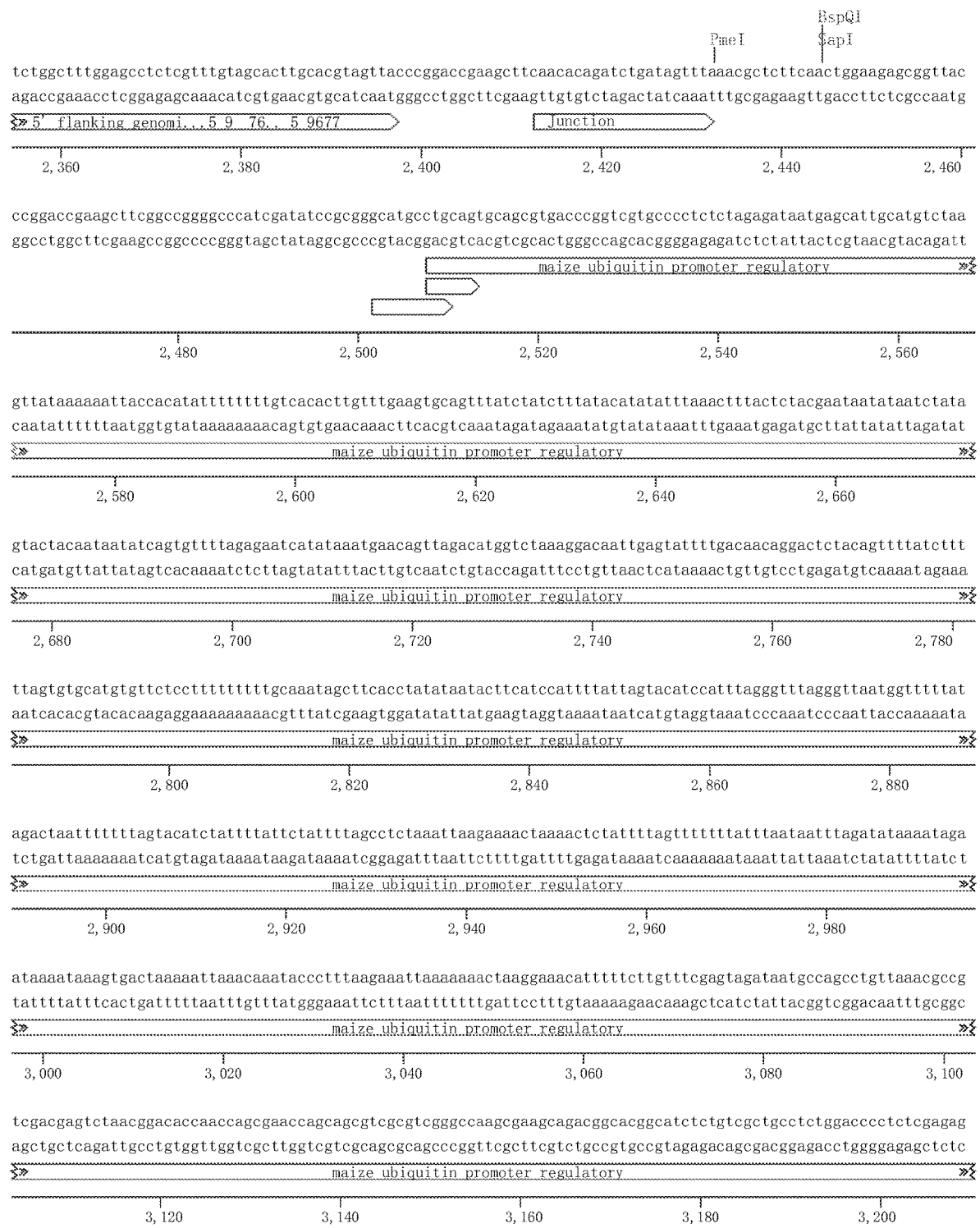

Specification includes a Sequence Listing.

(56) References Cited

U.S. PATENT DOCUMENTS

| | | | |
|---|---|---|---|
| 2023/0078387 | A1 | 3/2023 | Kock et al. |
| 2023/0083144 | A1 | 3/2023 | Nuccio et al. |
| 2023/0087222 | A1 | 3/2023 | Kock et al. |
| 2023/0147013 | A1 | 5/2023 | Nuccio et al. |
| 2023/0200336 | A1 | 6/2023 | Nuccio et al. |
| 2023/0203514 | A1 | 6/2023 | Price et al. |
| 2023/0265445 | A1 | 8/2023 | Kock et al. |
| 2024/0011042 | A1 | 1/2024 | Kock et al. |

FOREIGN PATENT DOCUMENTS

| | | | |
|---|---|---|---|
| WO | 2022026390 | A1 | 2/2022 |
| WO | 2022026395 | A2 | 2/2022 |
| WO | 2022026403 | A2 | 2/2022 |

OTHER PUBLICATIONS

Young et al., "CRISPR-Cas9 Editing in Maize: Systematic Evaluation of Off-target Activity and Its Relevance in Crop Improvement", Scientific Reports, vol. 9, 11 pages, Apr. 15, 2019.

Du et al., "Construction of Marker-Free Genetically Modified Maize Using a Heat-Inducible Auto-Excision Vector", Genes, vol. 10, No. 374, pp. 1-17, 2019.

Que et al., "Maize transformation technology development for commercial event generation", Frontiers in Plant Science, vol. 5, Article 379, pp. 1-19, 2014.

Ward et al., "Petition for Determination of Nonregulated Status for Insect-Resistant MIR162 Maize", Syngenta, pp. 1-271, 2007.

United States Patent and Trademark Office in connection with U.S. Appl. No. 17/248,936, filed Feb. 12, 2021, "Non-Final Office Action" 30 pages, mailed Mar. 25, 2021.

Baliga et al., "Investigation of direct repeats, spacers and proteins associated with clustered regularly interspaced short palindromic repeat (CRISPR) system of Vibrio parahaemolyticus", Molecular Genetics and Genomics, vol. 294, pp. 253-262, 2019.

Kim et al., "CRISPR/Cpf1-mediated DNA-free plant genome editing", Nature Communications, vol. 8, No. 14406, pp. 1-20, Feb. 16, 2017.

Li et al., "Expanding the Scope of CRISPR/Cpf1-Mediated Genome Editing in Rice", Molecular Plant, vol. 11, pp. 995-998, Jul. 2018.

United States Patent and Trademark Office in connection with U.S. Appl. No. 17/302,739, filed May 11, 2021, "Non-Final Office Action", 29 pages, mailed Aug. 3, 2021.

United States Patent and Trademark Office in connection with U.S. Appl. No. 17/302,110, filed Apr. 23, 2021, "Non-Final Office Action", 22 pages, Jun. 29, 2021.

United States Patent and Trademark Office in connection with U.S. Appl. No. 17/302,121, filed Apr. 23, 2021, "Non-Final Office Action", 10 pages, mailed Jul. 8, 2021.

Ward, Dennis P., "Petition for Determination of Nonregulated Status for Insect-Resistant MIR162 Maize", Syngenta, pp. 1-268, Aug. 31, 2007.

Srivastava, et al., "Dual-targeting by CRISPR/Cas9 for precise excision of transgenes from rice genome", Plant Cell Tissue and Organ Culture, vol. 129, pp. 153-160, 2017.

Malzahn et al., "Application of CRISPR-Cas12a temperature sensitivity for improved genome editing in rice, maize, and *Arabidopsis*", BMC Biology, vol. 17, No. 9, https://doi.org/10.1186/s12915-019-0629-5, pp. 1-14, 2019.

International Searching Authority in connection with PCT/US21/43945 filed Jul. 20, 2021, "Invitation to Pay Additional Fees and, Where Applicable, Protest Fee", 4 pages, mailed Oct. 27, 2021.

International Searching Authority in connection with PCT/US21/43935 filed Jul. 30, 2021, "Invitation to Pay Additional Fees and, Where Applicable, Protest Fee", 3 pages, mailed Oct. 26, 2021.

Finnigan et al., "mCAL: A New Approach for Versatile Multiplex Action of Cas9 Using One sgRNA and Loci Flanked by a Programmed Target Sequence", G3, vol. 6, pp. 2147-2156, Jul. 2016.

International Searching Authority in connection with PCT/US21/43897 filed Jul. 30, 2021, "Invitation to Pay Additional Fees and, Where Applicable, Protest Fee", 3 pages, mailed Oct. 27, 2021.

GenBank Accession No. CP0049894, "Arachis ipaensis cultivar K30076 chromosome 03," Jun. 3, 2020, https://www.ncbi.nlm.nih.gov/nuccore/CP049894, 2 pages.

International Search Report and Written Opinion in PCT/US2021/043897, mailed Feb. 10, 2022, 12 pages.

International Search Report and Written Opinion in PCT/US2021/043935, mailed Jan. 6, 2022, 13 pages.

International Search Report and Written Opinion in PCT/US2021/043945, mailed Jan. 21, 2022, 15 pages.

Final Office Action in U.S. Appl. No. 17/302,110, mailed Sep. 28, 2022, 27 pages.

Final Office Action in U.S. Appl. No. 17/302,739, mailed Dec. 8, 2021, 26 pages.

International Search Report in PCT/US2021/043161, mailed Jan. 5, 2022, 6 pages.

International Search Report in PCT/US2021/043170, mailed Jan. 5, 2022, 6 pages.

International Search Report in PCT/US2021/043187, mailed Jan. 6, 2022, 6 pages.

International Search Report in PCT/US2021/043192, mailed Jan. 27, 2022, 7 pages.

International Search Report in PCT/US2021/043207, mailed Jan. 27, 2022, 6 pages.

International Search Report in PCT/US2021/043440, mailed Dec. 2, 2021, 3 pages.

International Search Report in PCT/US2021/043468, mailed Nov. 26, 2021, 4 pages.

International Search Report in PCT/US2021/043479, mailed Nov. 23, 2021, 3 pages.

International Search Report in PCT/US2021/043483, mailed Dec. 16, 2021, 3 pages.

International Search Report in PCT/US2021/043496, mailed Dec. 1, 2021, 4 pages.

International Search Report in PCT/US2021/043851, mailed Dec. 30, 2021, 6 pages.

International Search Report in PCT/US2021/043919, mailed Jan. 20, 2022, 8 pages.

International Search Report in PCT/US2021/043933, mailed Dec. 30, 2021, 6 pages.

Non-Final Office Action in U.S. Appl. No. 17/302,110, mailed Jun. 29, 2021, 22 pages.

Non-Final Office Action in U.S. Appl. No. 17/302,110, mailed Mar. 15, 2022, 23 pages.

Non-Final Office Action in U.S. Appl. No. 17/302,110, mailed May 24, 2023, 27 pages.

Non-Final Office Action in U.S. Appl. No. 17/303,116, mailed Nov. 3, 2021, 42 pages.

Non-Final Office Action in U.S. Appl. No. 17/650,031, mailed May 26, 2023, 11 pages.

Non-Final Office Action in U.S. Appl. No. 18/057,860, mailed Jun. 1, 2023, 49 pages.

Non-Final Office Action in U.S. Appl. No. 18/057,867, mailed Jun. 7, 2023, 17 pages.

Non-Final Office Action in U.S. Appl. No. 18/058,081, mailed Apr. 11, 2023, 19 pages.

Non-Final Office Action in U.S. Appl. No. 18/058,144, mailed Jun. 7, 2023, 49 pages.

Non-Final Office Action in U.S. Appl. No. 18/058,156, mailed May 19, 2023, 24 pages.

Non-Final Office Action in U.S. Appl. No. 18/058,161, mailed Apr. 11, 2023, 15 pages.

Non-Final Office Action in U.S. Appl. No. 18/162,134, mailed Jun. 21, 2023, 28 pages.

Notice of Allowance in U.S. Appl. No. 17/248,936, mailed Mar. 10, 2022, 7 pages.

Notice of Allowance in U.S. Appl. No. 17/302,121, mailed Nov. 15, 2021, 7 pages.

Notice of Allowance in U.S. Appl. No. 17/302,739, mailed Mar. 30, 2022, 7 pages.

(56) References Cited

OTHER PUBLICATIONS

International Searching Authority in connection with PCT/US21/44198 filed Aug. 2, 2021, "The International Search Report and the Written Opinion of the International Searching Authority, or the Declaration", 20 pages, mailed Jan. 19, 2022.
Ali et al., "Fusion of the Cas9 endonuclease and the VirD2 relaxase facilitates homology-directed repair for precise genome engineering in rice," Communications Biology, vol. 3, Jan. 2020, 13 pages.
Bernabe-Orts et al., "Assessment of Cas12a-mediated gene editing efficiency in plants," Plant Biotechnology Journal, vol. 17, No. 10, 2019, pp. 1971-1984.
Cai et al., "Broadening the targetable space: engineering and discovery of PAM-flexible Cas proteins," Trends in Microbiology, May 2024, 4 pages.
Non-Final Office Action in U.S. Appl. No. 17/302,110, mailed Oct. 16, 2024, 24 pages.
Extended European Search Report in EP21849192.6, mailed Aug. 30, 2024, 17 pages.
Lee et al., "Activities and specificities of CRISPR/Cas9 and Cas12a nucleases for targeted mutagenesis in maize," Plant Biotechnology Journal, vol. 17, No. 2, 2019, pp. 362-372.
Non-Final Office Action in U.S. Appl. No. 18/162,134, mailed Sep. 26, 2024, 27 pages.
Wang et al., "Generation of marker-free transgenic rice using CRISPR/Cas9 system controlled by floral specific promoters," Journal of Genetics and Genomics, vol. 46, 2019, pp. 61-64.
Begemann MB, Gray BN, January E, Gordon GC, He Y, Liu H, Wu X, Brutnell TP, Mockler TC, Oufattole M. Precise insertion and guided editing of higher plant genomes using Cpf1 CRISPR nucleases. Scientific reports. Sep. 14, 2017;71:11606.
Non-Final Office Action in U.S. Appl. No. 18/057,860, mailed Apr. 26, 2024, 54 pages.
Non-Final Office Action in U.S. Appl. No. 18/058,144, mailed Apr. 12, 2024, 52 pages.
Specht DA, Xu Y, Lambert G. Massively parallel CRISPRi assays reveal concealed thermodynamic determinants of dCas12a binding. Proceedings of the National Academy of Sciences. May 26, 2020;11721:11274-82.
Toth E, Varga E, Kulcsár PI, Kocsis-Jutka V, Krausz SL, Nyeste A, Welker Z, Huszár K, Ligeti Z, Tálas A, Welker E. Improved LbCas12a variants with altered PAM specificities further broaden the genome targeting range of Cas 12a nucleases. Nucleic acids research. Apr. 17, 2020;48(7):3722-33.
Zhong Z, Zhang Y, You Q, Tang X, Ren Q, Liu S, Yang L, Wang Y, Liu X, Liu B, Zhang T. Plant genome editing using FnCpf1 and LbCpf1 nucleases at redefined and altered PAM sites. Molecular Plant. Jul. 2, 2018;11(7):999-1002.

\* cited by examiner

DP-4114_(DP-004114-3) (16752 bp)

```
                                              Baer
                                               |
gagcatatccagcaccagctggtaccaaggtcgggtctctgtgctagtgctattagctagtgtaaggagcgagtaggtcagttaaggctggtgcgtcgtgagggctg
ctcgtataggtcgtggtcgaccatggttccagcccagagacacgatcacgataatcgatcacattcctcgctcatccagtcaattccgaccacgcagcactcccgac
          5' flanking genomic sequence Chr1:15194376..15196773
         20         40         60         80        100 tcttgtgtgtagctacagcagacggttcatcagaaggattattcgtgcagtatatacagtacaactagacaatgatgttgatgattggtctagagctagaggcctat
agaacacacatcgatgtcgtctgccaagtagtcttcctaataagcacgtcatatatgtcatgttgatctgttactacaactactaaccagatctcgatctccggata
          5' flanking genomic sequence Chr1:15194376..15196773
        120        140        160        180        200 agccctatactactgtgtattgtccgccgttttagttttttggtcccatcccatcaatgcaaccgccttgttttgctccaattgtcccgttcctgcgcctcgctttt
tcgggatatgatgacacataacaggcggcaaaatcaaaaaaccagggtagggtagttacgttggcggaacaaaacgaggttaacagggcaaggacgcggagcgaaaa
          5' flanking genomic sequence Chr1:15194376..15196773
        220        240        260        280        300        320

Nrur
                                                                                                     |
gctctgtcgcatcgcatacaaaaaaaaaaacgccgcgccggctttgaatcgcgcccccaactgctccaaccaggcaacggacacggccaccgtccgtgtcgcgagc
cgagacagcgtagcgtatgtttttttttttgcggcgcggccgaaacttagcgcggggggttgacgaggttggtccgttgcctgtgccggtggcaggcacagcgctcg
          5' flanking genomic sequence Chr1:15194376..15196773
        340        360        380        400        420 aaaaaaacaaaaagaggaacgcgtccaggacgaagcagtccactgccgctgtggccggcaaaagatctggttgagcacatggagattggagaaggttggttggttct
ttttttttgttttctccttgcgcaggtcctgcttcgtcaggtgacggcgacaccggccgttttctagaccaactcgtgtacctctaacctcttccaaccaaccaaga
          5' flanking genomic sequence Chr1:15194376..15196773
        440        460        480        500        520 tctggaaacgccaatgaatgggggcactgacatgtactcttaacatgtagtgcaatccagagatcggatatccagacactggcagcacgatcgcctcgcgccgtaga
agacctttgcggttacttaccccgtgactgtacatgagaattgtacatcacgttaggtctctagcctataggtctgtgaccgtcgtgctagcggagcgcggcatct
          5' flanking genomic sequence Chr1:15194376..15196773
        540        560        580        600        620        640 tcacgcacgcaaattactgaagaccattcacaaaaaaaaaaaaacacacaggggctagcgtgcccacaccaaacccaagtgctgcgttgcacgcaggggagcgaaa
agtgcgtgcgtttaatgacttctggtaagtgttttttttttttttgtgtgtccccgatcgcacggggtgtggtttgggttcacgacgcaacgtgcgtcccctcgcttt
          5' flanking genomic sequence Chr1:15194376..15196773
        660        680        700        720        740
```

FIG. 1A

```
                                                                                               BstAPI
aaaaacaataatgctcactgtcacgtcgcgtatccaaccccgcggacgtctcggctctcagcagcagcacacggggcacctcacgatgccgttctcgttgcactccg
ttttgttattacgagtgacagtgcagcgcataggttggggcgcctgcagagccgagagtcgtcgtcgtgtgccccgtggagtgctacggcaagagcaacgtgaggc
≶»       5' flanking genomic sequence Chr1:15194376..15196773                              »≷
         |              |              |              |              |
        760            780            800            820            840 tgcaccgccggaacccgccgccgcattcgtcgccctcctcctcctcctccgcctcgtcttcgtcacccacgtacaccttgcagctgcccgagcagacatcgcagagc
acgtggcggccttgggcggcggcgtaagcagcggggaggaggaggaggaggcggagcagaagcagtgggtgcatgtggaacgtcgacggctcgtctgtagcgtctcg
≶»       5' flanking genomic sequence Chr1:15194376..15196773                              »≷
  |              |              |              |              |              |
 860            880            900            920            940            960

SgrAI
                            |MreI                         FseI
acgaaccgcatgtccccgcaggcctcgcacgcgccggcgtcgccgccgtgtgggccggccgtcgacgcagcgctctcgcacccggccagcctcggcgcgagctcccc
tgcttggcgtacaggggcgtccggagcgtgcgcggccgcagcggcggcacacccggccggcagctgcgtcgcgagagcgtgggccggtcggagccgcgctcgagggg
≶»       5' flanking genomic sequence Chr1:15194376..15196773                              »≷
              |              |              |              |              |
             980          1,000          1,020          1,040          1,060 ggcctcgtgcagccgcttcagctcctcggcgttgcccacgagctccccgtccacgaagaggctggggagggcggcgggcgtgccgccggcttggccgagcccgaggc
ccggagcacgtcggcgaagtcgaggagccgcaacgggtgctcgaggggcaggtgcttctccgaccctcccgccgcccgcacggcggccgaaccggctcgggctccg
≶»       5' flanking genomic sequence Chr1:15194376..15196773                              »≷
     |              |              |              |              |
   1,080          1,100          1,120          1,140          1,160 cgagaaggccgcggagctcgtcccggaacccgcggtgcatggacacgtcgcgctcgtcgaggcgcacgccgtagcccttgaggatggcgcgcgccaggcagcagtcc
gctcttccggcgcctcgagcagggccttgggcgccacgtacctgtgcagcgcgagcagctccgcgtgcggcatcgggaactcctaccgcgcgcggtccgtcgtcagg
≶»       5' flanking genomic sequence Chr1:15194376..15196773                              »≷
|              |              |              |              |              |
1,180         1,200          1,220          1,240          1,260          1,280 tcgtgcgtggcgcgcacgccgcgcagcgacgtgaagtagagcaccgccctccgcggcggcagcgcctttcccctccccgccgctcgtcggggcggcgtcgggccgagg
agcacgcaccgcgcgtgcggcgcgtcgctgcacttcatctcgtggcgggaggcgccgccgtcgcggaaggggaggggcggcgagcagccccgccgcagcccggctcc
≶»       5' flanking genomic sequence Chr1:15194376..15196773                              »≷
       |              |              |              |              |
     1,300          1,320          1,340          1,360          1,380

AscI
                                                                                               |
catcggcatcggcagcggcgtcaccttggcggacgccgcgaggtcctgcgcaggcgccgtggcgaccgggaacgagaaggagtggcgcccgaacgcgcgcgcccagca
gtagccgtagccgtcgccgcagtggaaccgcctgcggcgctccaggacgcgtccgcggcaccgctggcccttgctcttcctcaccgcgggcttgccgcgcgggtcgt
≶»       5' flanking genomic sequence Chr1:15194376..15196773                              »≷
   |              |              |              |              |
 1,400          1,420          1,440          1,460          1,480
```

FIG. 1B

```
                       FseI
                         |
gcggggagcggtcctcgaggccggccatgagcgcccacgcgtcgatgtcctcgggctcgttgggcggcgtcatggtgggcgtgcgcggcgccagcctcgtgggcgcg
cgcccctcgccaggagctccggccggtactcgcgggtgcgcagctacaggagcccgagcaacccgccgcagtaccacccgcacgcgccgcggtcggagcacccgcgc
```
»— 5' flanking genomic sequence Chr1:15194376..15196773 —«

| 1,500 | 1,520 | 1,540 | 1,560 | 1,580 | 1,600 |

```
                        KflI
                          |
ggctccggcgcccgcggcagggccttgtccagctccagggacccgagcgtggacgacgtgagccgcaccacgtggacgccgacgtcgctggggcaccgagccgggaa
ccgaggccgcgggcgccgtcccggaacaggtcgaggtccctgggctcgcacctgctgcactcggcgtggtgcacctgcggctgcagcgaccccgtggctcggcccctt
```
»— 5' flanking genomic sequence Chr1:15194376..15196773 —«

| 1,620 | 1,640 | 1,660 | 1,680 | 1,700 |

```
cgactggctgcgcggcagcggtgacgggcagtaccggaggtcgtgacgggcctgccttgaggtggtgcaccccatggcaccaatgtacacacacggccaaagcgcca
gctgaccgacgcgccgtcgccactgcccgtcatggcctccagcactgcccggacggaactccaccacgtggggtaccgtggttacatgtgtgtgccggtttcgcggt
```
»— 5' flanking genomic sequence Chr1:15194376..15196773 —«

| 1,720 | 1,740 | 1,760 | 1,780 | 1,800 |

```
agtgggctgcagactgcctgccaatgtgatcaagcagccaggagcagagacggatctctggggatcggggtttctggggtttaggatctttatactactctgtcatt
tcacccgacgtctgacggacggttacactagttcgtcggtcctcgtctctgcctagagacccctagccccaaagaccccaaatcctagaaatatgatgagacagtaa
```
»— 5' flanking genomic sequence Chr1:15194376..15196773 —«

| 1,820 | 1,840 | 1,860 | 1,880 | 1,900 | 1,920 |

```
ggggatataaaactaggagtgtggttaattaggactcgatagataagtttaccacaagcgcgtgaaatggtctacccgatgatgtgattggcctaaaaagaacaaga
cccctatattttgatcctcacaccaattaatcctgagctatctattcaaatggtgttcgcgcactttaccagatgggctactacactaaccggattttcttgttct
```
»— 5' flanking genomic sequence Chr1:15194376..15196773 —«

| 1,940 | 1,960 | 1,980 | 2,000 | 2,020 |

```
agagtatttggagctactgaacattctcttttcctgaagataactaattttggaacattcagacttgggagtctggacttttggagggaagttcaaattgtggtct
tctcataaacctcgatgacttgtaagagaaaaggacttctattgattaaaaaccttgtaagtctgaaccctcagacctgaaaacctcccttcaagtttaacaccaga
```
»— 5' flanking genomic sequence Chr1:15194376..15196773 —«

| 2,040 | 2,060 | 2,080 | 2,100 | 2,120 | 2,140 |

```
gcctctgccatgtgttgttttttagtcggagagtggccctcattttttttgtcctgtttagctttatagtcgtagcagctagtagcgaaatttaaccttggattatg
cggagacggtacacaacaaaaaatcagcctctcaccgggagtaaaaaaaacaggacaaatcgaaatatcagcatcgtcgatcatcgctttaaattggaacctaatac
```
»— 5' flanking genomic sequence Chr1:15194376..15196773 —«

| 2,160 | 2,180 | 2,200 | 2,220 | 2,240 |

```
gccgtgttagtcaaacaatcattgatttatttcctcccttcgcgctgcttttcctgtacgcatctccgctgcccttgattcgaggaccctgttcacaacacagggc
cggcacaatcagtttgttagtaactaaataaggagggaaagcgcgacgaaaaggacatgcgtagaggcgacgggaactaagctcctgggacaagtgttgtgtcccg
```
»— 5' flanking genomic sequence Chr1:15194376..15196773 —«

| 2,260 | 2,280 | 2,300 | 2,320 | 2,340 |

FIG. 1C ttccgctccaccgttggacttgctccgctgtcggcatccagaaattgcgtggcggagcggcagacgtgagccggcacggcaggcggcctcctcctcctctcacggca
aaggcgaggtggcaacctgaacgaggcgacagccgtaggtctttaacgcaccgcctcgccgtctgcactcggccgtgccgtccgccggaggaggaggagagtgccgt ccggcagctacggggggattcctttcccaccgctccttcgctttccttcctcgcccgccgtaataaatagacacccctccacaccctctttccccaacctcgtgtt
ggccgtcgatgccccctaaggaaagggtggcgaggaagcgaaagggaaggagcgggcggcattatttatctgtgggggaggtgtgggagaaagggggttggagcacaa gttcggagcgcacacacacacaaccagatctcccccaaatccacccgtcggcacctccgcttcaaggtacgccgctcgtcctcccccccccccctctctaccttct
caagcctcgcgtgtgtgtgtgttggtctagagggggtttaggtgggcagccgtggaggcgaagttccatgcggcgagcaggaggggggggggggagagatggaaga ctagatcggcgttccggtccatggttagggcccggtagttctacttctgttcatgtttgtgttagatccgtgtttgtgttagatccgtgctgctagcgttcgtacac
gatctagccgcaaggccaggtaccaatcccgggccatcaagatgaagacaagtacaaacacaatctaggcacaaacacaatctaggcacgacgatcgcaagcatgtg ggatgcgacctgtacgtcagacacgttctgattgctaacttgccagtgtttctctttggggaatcctgggatggctctagccgttccgcagacgggatcgatttcat
cctacgctggacatgcagtctgtgcaagactaacgattgaacggtcacaaagagaaaccccttaggaccctaccgagatcggcaaggcgtctgccctagctaaagta gatttttttgtttcgttgcatagggtttggtttgcccttttcctttatttcaatatatgccgtgcacttgtttgtcgggtcatcttttcatgcttttttttgtctt
ctaaaaaaaacaaagcaacgtatcccaaaccaaacgggaaaaggaaataaagttatatacggcacgtgaacaaacagcccagtagaaaagtacgaaaaaaaacagaa

FIG. 1E ggttgtgatgatgtggtctggttgggcggtcgttctagatcggagtagaattctgtttcaaactacctggtggatttattaattttggatctgtatgtgtgtgccat
ccaacactactacaccagaccaacccgccagcaagatctagcctcatcttaagacaaagtttgatggaccacctaaataattaaaacctagacatacacacacggta

```
                                    ubi1; maize ubiquitin intron
                                         Ubi1 5'UTR
                                 maize ubiquitin promoter regulatory
                                         Maize Ubi intron
                                         Maize Ubi gene
```

3,860          3,880          3,900          3,920          3,940 acatattcatagttacgaattgaagatgatggatggaaatatcgatctaggataggtatacatgttgatgcgggttttactgatgcatatacagagatgcttttgt
tgtataagtatcaatgcttaacttctactacctacctttatagctagatcctatccatatgtacaactacgcccaaaatgactacgtatatgtctctacgaaaaaca

```
                                    ubi1; maize ubiquitin intron
                                         Ubi1 5'UTR
                                 maize ubiquitin promoter regulatory
                                         Maize Ubi intron
                                         Maize Ubi gene
```

3,960          3,980          4,000          4,020          4,040          4,060 tcgcttggttgtgatgatgtggtgtggttgggcggtcgttcattcgttctagatcggagtagaatactgtttcaaactacctggtgtatttattaattttggaactg
agcgaaccaacactactacaccacaccaacccgccagcaagtaagcaagatctagcctcatcttatgacaaagtttgatggaccacataaataattaaaaccttgac

```
                                    ubi1; maize ubiquitin intron
                                         Ubi1 5'UTR
                                 maize ubiquitin promoter regulatory
                                         Maize Ubi intron
                                         Maize Ubi gene
```

4,080          4,100          4,120          4,140          4,160 tatgtgtgtgtcatacatcttcatagttacgagtttaagatggatggaaatatcgatctaggataggtatacatgttgatgtgggttttactgatgcatatacatga
atacacacacagtatgtagaagtatcaatgctcaaattctacctacctttatagctagatcctatccatatgtacaactacacccaaaatgactacgtatatgtact

```
                                    ubi1; maize ubiquitin intron
                                         Ubi1 5'UTR
                                 maize ubiquitin promoter regulatory
                                         Maize Ubi intron
                                         Maize Ubi gene
```

4,180          4,200          4,220          4,240          4,260          4,280 tggcatatgcagcatctattcatatgctctaaccttgagtacctatctattataataaacaagtatgttttataattattttgatcttgatatacttggatgatggc
accgtatacgtcgtagataagtatacgagattggaactcatggatagataatatattatttgttcatacaaaatattaataaaactagaactatatgaacctactaccg

```
                                    ubi1; maize ubiquitin intron
                                         Ubi1 5'UTR
                                 maize ubiquitin promoter regulatory
                                         Maize Ubi intron
                                         Maize Ubi gene
```

4,500          4,520          4,540          4,560          4,580

FIG. 1F atatgcagcagctatatgtggattttttagccctgccttcatacgctatttatttgcttggtactgtttcttttgtcgatgctcaccctgttgtttggtgttactt
tatacgtcgtcgatatacacctaaaaaaatcgggacggaagtatgcgataaataaacgaaccatgacaaagaaaacagctacgagtgggacaacaaaccacaatgaa > ubi1; maize ubiquitin intron
> Ubi1 5' UTR
> maize ubiquitin promoter regulatory
> Maize Ubi intron
> Maize Ubi gene 4,400   4,420   4,440   4,460   4,480 ctgcaggtcgactctagaggatccaacaatggagaacaacatacagaatcagtgcgtccctacaactgcctcaacaatcctgaagtagagattctcaacgaagaga
gacgtccagctgagatctcctaggttgttacctcttgttgtatgtcttagtcacgcaggggatgttgacggagttgttaggacttcatctctaagagttgcttctct > Omega...tory
> cryIF protein 4,500   4,520   4,540   4,560   4,580   4,600 ggtcgactggcagattgccgttagacatctccctgtcccttac tttggataccentacaatcagggattggagaacctgagaggtactaacactcgccaatgggccaggttcaatcagttcaggagagaccttacacttactgtgttagaca
aaacctatggatgttagtccctaacctcttggactctccatgattgtgagcggttacccggtccaagttagtcaagtcctctctggaatgtgaatgacacaatctgt

| » | crylF protein | »< |
|---|---|---|

5,140  5,160  5,180  5,200  5,220  5,240 tagttgctctctcttccgaactacgatgttcgtacctatcc

```
gacattcttcgacgcactagtggaggaccattcgcgtacaccattgtcaacatcaatgggcaacttccccaaaggtatcgtgccaggatacgctatgcctctactac
ctgtaagaagctgcgtgatcacctcctggtaagcgcatgtggtaacagttgtagttacccgttgaaggggttttccatagcacggtcctatgcgatacggagatgatg
```

>> cry F protein >>
6,000    6,020    6,040    6,060    6,080

Age I

```
caatctaagaatctacgttacggttgcaggtgaacggatctttgctggtcagttcaacaagacaatggataccggtgatccacttacattccaatctttctcctacg
gttagattcttagatgcaatgccaacgtccacttgcctagaaacgaccagtcaagttgttctgttacctatggccactaggtgaatgtaaggttagaaagaggatgc
```

>> cry F protein >>
6,100    6,120    6,140    6,160    6,180    6,200

```
ccactatcaacaccgcgttcacctttccaatgagccagagcagtttcacagtaggtgctgataccttcagttcaggcaacgaagtgtacattgacaggtttgagttg
ggtgatagttgtggcgcaagtggaaaggttactcggtctcgtcaaagtgtcatccacgactatggaagtcaagtccgttgcttcacatgtaactgtccaaactcaac
```

>> cry F protein >>
6,220

```
                BbvCI
                  |
tagatgccgggctcgacgctgaggacattgcctaccttgagcatggtctcagcgccggctttaagctcaatcccatcccaatctgaatatcctatcccgcgcccagt
atctacggcccgagctgcgactcctgtaacggatggaactcgtaccagagtcgcggccgaaattcgagttagggtagggttagacttataggataggggcgcgggtca
    |              |              |              |              |              |
  6,960          6,980          7,000          7,020          7,040          7,060 ccggtgtaagaacgggtctgtccatccacctctgttgggaattccggtccgggtcacctttgtccaccaagatggaactgcggccagcttgcatgcctgcagtgcag
ggccacattcttgcccagacaggtaggtggagacaacccttaaggccaggcccagtggaaacaggtggttctaccttgacgccggtcgaacgtacggacgtcacgtc
                                                                                              ma..y
    |              |              |              |              |              |
  7,080          7,100          7,120          7,140          7,160 cgtgacccggtcgtgcccctctctagagataatgagcattgcatgtctaagttataaaaaattaccacatatttttttttgtcacacttgtttgaagtgcagtttatc
gcactgggccagcacggggagagatctctattactcgtaacgtacagattcaatatttttttaatggtgtataaaaaaaacagtgtgaacaaacttcacgtcaaatag
                                    maize ubiquitin promoter regulatory
    |              |              |              |              |
  7,180          7,200          7,220          7,240          7,260 tatctttatacatatatttaaactttactctacgaataatataatctatagtactacaataatatcagtgttttagagaatcatataaatgaacagttagacatggt
atagaaatatgtatataaatttgaaatgagatgcttattatattagatatcatgatgttattatagtcacaaaatctcttagtatatttacttgtcaatctgtacca
                                    maize ubiquitin promoter regulatory
    |              |              |              |              |              |
  7,280          7,300          7,320          7,340          7,360          7,380 ctaaaggacaattgagtattttgacaacaggactctacagttttatcttttagtgtgcatgtgttctccttttttttgcaaatagcttcacctatataatacttc
gatttcctgttaactcataaaactgttgtcctgagatgtcaaaatagaaaatcacacgtacacaagaggaaaaaaaacgtttatcgaagtggatatattatgaag
                                    maize ubiquitin promoter regulatory
    |              |              |              |              |
  7,400          7,420          7,440          7,460          7,480 atccattttattagtacatccatttagggtttagggttaatggttttttatagactaattttttttagtacatctatttttattctattttagcctctaaattaagaaaa
taggtaaaataatcatgtaggtaaatcccaaatcccaattaccaaaaatatctgattaaaaaaatcatgtagataaaataagataaatcggagatttaattcttttt
                                    maize ubiquitin promoter regulatory
    |              |              |              |              |
  7,500          7,520          7,540          7,560          7,580 ctaaaactctatttttagttttttttatttaataatttagatataaaatagaataaaataaagtgactaaaaattaaacaaatacccttttaagaaattaaaaaactaa
gattttgagataaaatcaaaaaaataaattattaaatctatattttatcttatttttattttcactgattttttaatttgtttatgggaaattctttaatttttttgatt
                                    maize ubiquitin promoter regulatory
    |              |              |              |              |              |
  7,600          7,620          7,640          7,660          7,680          7,700 ggaaacattttttcttgtttcgagtagataatgccagcctgttaaacgccgtcgacgagtctaacggacaccaaccagcgaaccagcagcgtcgcgtcgggccaagcg
cctttgtaaaagaacaaagctcatctattacggtcggacaatttgcggcagctgctcagattgcctgtggttggtcgcttggtcgtcgcagcgcagcccggttcgc
                                    maize ubiquitin promoter regulatory
    |              |              |              |              |
  7,720          7,740          7,760          7,780          7,800
```

FIG. 1J

```
atgccgtgcacttgtttgtcgggtcatcttttcatgctttttttgtcttggttgtgatgatgtggtctggttgggcggtcgttctagatcggagtagaattctgtt
tacggcacgtgaacaaacagcccagtagaaaagtacgaaaaaaaacagaaccaacactactacaccagaccaacccgccagcaagatctagcctcatcttaagacaa
```

```
ubi1; maize ubiquitin intron
Ubi1 5'UTR
Maize Ubi intron
maize ubiquitin promoter regulatory
Maize Ubi gene
```

8,460   8,480   8,500   8,520   8,540   8,560

```
tcaaactacctggtggatttattaattttggatctgtatgtgtgtgccatacatattcatagttacgaattgaagatgatggatggaaatatcgatctaggataggt
agtttgatggaccacctaaataattaaaacctagacatacacacacggtatgtataagtatcaatgcttaacttctactacctaccttatagctagatcctatcca
```

```
ubi1; maize ubiquitin intron
Ubi1 5'UTR
Maize Ubi intron
maize ubiquitin promoter regulatory
Maize Ubi gene
```

8,580   8,600   8,620   8,640   8,660

```
atacatgttgatgcgggttttactgatgcatatacagagatgctttttgttcgcttggttgtgatgatgtggtgtggttgggcggtcgttcattcgttctagatcgg
tatgtacaactacgcccaaaatgactacgtatatgtctctacgaaaaacaagcgaaccaacactactacaccacaccaacccgccagcaagtaagcaagatctagcc
```

```
ubi1; maize ubiquitin intron
Ubi1 5'UTR
Maize Ubi intron
maize ubiquitin promoter regulatory
Maize Ubi gene
```

8,680   8,700   8,720   8,740   8,760

```
agtagaatactgtttcaaactacctggtgtatttattaattttggaactgtatgtgtgtgtcatacatcttcatagttacgagtttaagatggatggaaatatcgat
tcatcttatgacaaagtttgatggaccacataaataattaaaaccttgacatacacacacagtatgtagaagtatcaatgctcaaattctacctacctttatagcta
```

```
ubi1; maize ubiquitin intron
Ubi1 5'UTR
Maize Ubi intron
maize ubiquitin promoter regulatory
Maize Ubi gene
```

8,780   8,800   8,820   8,840   8,860   8,880

```
ctaggataggtatacatgttgatgtgggttttactgatgcatatacatgatggcatatgcagcatctattcatatgctctaaccttgagtacctatctattataata
gatcctatccatatgtacaactacacccaaaatgactacgtatatgtactaccgtatacgtcgtagataagtatacgagattggaactcatggatagataatattat
```

```
ubi1; maize ubiquitin intron
Ubi1 5'UTR
Maize Ubi intron
maize ubiquitin promoter regulatory
Maize Ubi gene
```

8,900   8,920   8,940   8,960   8,980

FIG. 1L ttatcctaaatgaatgtcacgtgtctttataattctttgatgaaccagatgcatttcattaaccaaatccatatacatataaatattaatcatatataattaatatc
aataggatttacttacagtgcacagaaatattaagaaactacttggtctacgtaaagtaattggtttaggtatatgtatatttataattagtatatattaattatag pinII Terminator 9,740       9,760       9,780       9,800       9,820       9,840

NotI aattgggttagcaaaacaaatctagtctaggtgtgttttgcgaatgcggccgcggaccgaattggggatctgcatgaaagaaactgtcgcactgctgaaccgcacct
ttaacccaatcgttttgtttagatcagatccacacaaaacgcttacgccggcgcctggcttaaccccctagacgtactttctttgacagcgtgacgacttggcgtgga pinII Terminator    polylinker    TA Peroxidase Promoter 9,860       9,880       9,900       9,920       9,940 tgtcactttcatcgaacacgacctgtgcccaagatgacggtgctgcggtctaagtgaggctgaattgccttggacagaagcggactccctacaattagttaggccaa
acagtgaaagtagcttgtgctggacacgggttctactgccacgacgccagattcactccgacttaacggaacctgtcttcgcctgagggatgttaatcaatccggtt TA Peroxidase Promoter 9,960       9,980       10,000      10,020      10,040 acggtgcatccatgtgtagctccgggctcggggctgtatcgccatctgcaatagcatccatggagctcgttccatgtagttggagatgaaccaatgatcgggcgtgtg
tgccacgtaggtacacatcgaggcccgagcccgacatagcggtagacgttatcgtaggtacctcgagcaaggtacatcaacctctacttggttactagcccgcacac TA Peroxidase Promoter 10,060      10,080      10,100      10,120      10,140      10,160 gacgtatgttcctgtgtactccgatagtagagtacgtgttagctctttcatggtgcaagtgaaatttgtgttggtttaattacccctacgttagttgcgggacagga
ctgcatacaaggacacatgaggctatcatctcatgcacaatcgagaaagtaccacgttcactttaaacacaaccaaattaatggggatgcaatcaacgcccgtcct TA Peroxidase Promoter 10,180      10,200      10,220      10,240      10,260 gacacatcatgaatttaaaggcgatgatgtcctctcctgtaatgttattcttttgatgtgatgaatcaaaatgtcatataaaacatttgttgctctttagttaggcc
ctgtgtagtacttaaatttccgctactacaggagaggacattacaataagaaaactacactacttagttttacagtatattttgtaaacaacgagaaatcaatccgg TA Peroxidase Promoter 10,280      10,300      10,320      10,340      10,360 tgatcgtagaacgaaatgctcgtgtagcggggctacgagcctatgacgcaataacactggtttgccggcccggagtcgcttgacaaaaaaaagcatgttaagtttat
actagcatcttgctttacgagcacatcgccccgatgctcggatactgcgttattgtgaccaaacggccgggcctcagcgaactgttttttttcgtacaattcaaata TA Peroxidase Promoter 10,400      10,420      10,440      10,460      10,480

BaeI ttacaattcaaaacctaacatatatattccctcaaagcaggttcacgatcacacctgtacctaaaaaaaacatgaagaatatattactccattattatgagatgaa
aatgttaagttttggattgtataatataagggagtttcgtccaagtgctagtgtggacatggatttttttttgtacttcttatataatgaggtaataatactctactt TA Peroxidase Promoter 10,500      10,520      10,540      10,560      10,580

FIG. 1N

BstBI ccacttggcaagagtggtaagctatataaaaaaatgaacattattacgagatgttatatgccattatattgattcgaagatatatgtttctttctcccacgggcacc
ggtgaaccgttctcaccattcgatatatttttttacttgtaataatgctctacaatatacggtaatataactaagcttctatatacaaagaaagagggtgcccgtgg TA Peroxidase Promoter 10,600 10,620 10,640 10,660 10,680 10,700

BstBI taacggatacatgataaggccaaggcagatcacgggaaattattcgaatacatgttacgccctattgccggaaaaaaaatgcagggcaggtgttggccgtagcgatt
attgcctatgtactattccggttccgtctagtgccctttaataagcttatgtacaatgcgggataacggcctttttttttacgtcccgtccacaaccggcatcgctaa TA Peroxidase Promoter 10,720 10,740 10,760 10,780 10,800

AflII taagcacttaagctggaggttgccacacttggatgcaagcgtctgacccttctaaaaaatcggcggctttgtccgtatccgtatcccctatccaacatctagctggc
attcgtgaattcgacctccaacggtgtgaacctacgttcgcagactgggaagatttttttagccgccgaaacaggcataggcataggggataggttgtagatcgaccg TA Peroxidase Promoter 10,820 10,840 10,860 10,880 10,900 cacacgacggggctgggcagatcgtggatgccgggtcgacgtcgatcgtcagccatcatagaccaatcgaccatctgttatggatgcttgctagctagactagtcag
gtgtgctgccccgacccgtctagcacctacggcccagctgcagctagcagtcggtagtatctggttagctggtagacaatacctacgaacgatcgatctgatcagtc TA Peroxidase Promoter 10,920 10,940 10,960 10,980 11,000 11,020 acataaaatttggatactttctcccaactgggagacggggactgatgtgcagctgcacgtgagctaaatttttccctataaatatgcatgaaatactgcattatctt
tgtattttaaacctatgaaagagggttgaccctctgcccctgactacacgtcgacgtgcactcgatttaaaaagggatatttatacgtactttatgacgtaatagaa TA Peroxidase Promoter 11,040 11,060 11,080 11,100 11,120 gccacagccactgccacagccagataacaagtgcagctggtagcacgcaacgcatagctctggacttgtagctaggtagccaaccggatccacacgacaccatgctc
cggtgtcggtgacggtgtcggtctattgttcacgtcgaccatcgtgcgttgcgtatcgagacctgaacatcgatccatcggttggcctaggtgtgctgtggtacgag TA Peroxidase Promoter 11,140 11,160 11,180 11,200 11,220 gacaccaacaaggtgtacgagatcagcaaccacgccaacggcctctacgccgccacctacctctccctcgacgactccggcgtgtccctcatgaacaagaacgacga
ctgtggttgttccacatgctctagtcgttggtgcggttgccggagatgcggcggtggatggagagggagctgctgaggccgcacagggagtacttgttcttgctgct cry35Ab1 protein 11,240 11,260 11,280 11,300 11,320 11,340 cgacatcgacgactacaacctcaagtggttcctcttcccgatcgacgacgaccagtacatcatcacctcctacgccgccaacaactgcaaggtgtggaacgtgaaca
gctgtagctgctgatgttggagttcaccaaggagaagggctagctgctgctggtcatgtagtagtggaggatgcggcggttgttgacgttccacaccttgcacttgt cry35Ab1 protein 11,360 11,380 11,400 11,420 11,440

FIG. 10 acgacaagattaatgtgtcaacctactcctccaccaactccatccagaagtggcagatcaaggccaacggctcctcctacgtgatccagtccgacaacggcaaggtg
tgctgttctaattacacagttggatgaggaggtggttgaggtaggtcttcaccgtctagttccggttgccgaggaggatgcactaggtcaggctgttgccgttccac cry35Ab1 protein 11,460    11,480    11,500    11,520    11,540 ctcaccgccggcaccggccaggccctcggcctcatccgcctcaccgacgagtcctccaacaacccgaaccagcaatggaacctgacgtccgtcagaccatccagct
gagtggcggccgtggccggtccgggagccggagtaggcggagtggctgctcaggaggttgttgggcttggtcgttaccttggactgcaggcacgtctggtaggtcga cry35Ab1 protein 11,560    11,580    11,600    11,620    11,640    11,660 cccgcagaagccgatcatcgacaccaagctcaaggactacccgaagtactccccgaccggcaacatcgacaacggcacctccccgcagctcatgggctggaccctcg
gggcgtcttcggctagtagctgtggttcgagttcctgatgggcttcatgagggggctggccgttgtagctgttgccgtggaggggcgtcgagtacccgacctgggagc cry35Ab1 protein 11,680    11,700    11,720    11,740    11,760 tgccgtgcatcatggtgaacgacccgaacatcgacaagaacacccagatcaagaccaccccgtactacatcctcaagaagtaccagtactggcagagggccgtgggc
acggcacgtagtaccacttgctgggcttgtagctgttcttgtgggtctagttctggtggggcatgatgtaggagttcttcatggtcatgaccgtctcccggcacccg cry35Ab1 protein 11,780    11,800    11,820    11,840    11,860 tccaacgtcgcgctccgcccgcacgagaagaagtcctacacctacgagtggggcaccgagatcgaccagaagaccaccatcatcaacaccctcggcttccagatcaa
aggttgcagcgcgaggcgggcgtgctcttcttcaggatgtggatgctcacccgtggctctagctggtcttctggtggtagtagttgtgggagccgaaggtctagtt cry35Ab1 protein 11,880    11,900    11,920    11,940    11,960    11,980 catcgacagcggcatgaagttcgacatcccggaggtgggcgcggtaccgacgagatcaagacccagctcaacgaggagctcaagatcgagtattcacatgagacga
gtagctgtcgccgtacttcaagctgtagggcctccacccgccgccatggctgctctagttctgggtcgagttgctcctcgagttctagctcataagtgtactctgct cry35Ab1 protein 12,000    12,020    12,040    12,060    12,080 agatcatggagaagtaccaggagcagtccgagatcgacaacccgaccgaccagtccatgaactccatcggcttcctcaccatcacctccctggagctctaccgctac
tctagtacctcttcatggtcctcgtcaggctctagctgtttgggctggctggtcaggtacttgaggtagccgaaggagtggtagtggagggacctcgagatggcgatg cry35Ab1 protein 12,100    12,120    12,140    12,160    12,180

BstAPI aacggctccgagatccgcatcatgcagatccagacctccgacaacgacacctacaacgtgacctcctacccgaaccaccagcaggccdtgctgctgctgaccaacca
ttgccgaggctctaggcgtagtacgtctaggtctggaggctgttgctgtggatgttgcactggaggatgggcttggtggtcgtccgggacgacgacgactggttggt cry35Ab1 protein 12,200    12,220    12,240    12,260    12,280    12,300

FIG. 1P

```
ctcctacgaggaggtggaggagatcaccaacatcccgaagtccaccctcaagaagctcaagaagtactacttctgagtcatgagtcatgagtcagttaacctagact
gaggatgctcctccacctcctctagtggttgtagggcttcaggtgggagttcttcgagttcttcatgatgaagactcagtactcagtactcagtcaattggatctga
```
`cry35Ab1 protein` | `polylinker`

12,320　　12,340　　12,360　　12,380　　12,400

PacI

```
tgtccatcttctggattggccaacttaattaatgtatgaaataaaaggatgcacacatagtgacatgctaatcactataatgtgggcatcaaagttgtgtgttatgt
acaggtagaagacctaaccggttgaattaattacatactttattttcctacgtgtgtatcactgtacgattagtgatattacacccgtagtttcaacacacaataca
```
`pinII ter`

12,420　　12,440　　12,460　　12,480　　12,500

```
gtaattactagttatctgaataaaagagaaagagatcatccatatttcttatcctaaatgaatgtcacgtgtctttataattctttgatgaaccagatgcatttcat
cattaatgatcaatagacttattttctctttctctagtaggtataaagaataggatttacttacagtgcacagaaatattaagaaactacttggtctacgtaaagta
```
`pinII ter`

12,540　　12,560　　12,580　　12,600　　12,620

```
taaccaaatccatatacatataaatattaatcatatataattaatatcaattgggttagcaaaacaaatctagtctaggtgtgttttgcgaattatcgatgggcccc
attggtttaggtatatgtatatttataattagtatatattaattatagttaacccaatcgttttgtttagatcagatccacacaaaacgcttaatagctacccgggg
```
`pinII ter` | `poly...ker`

12,640　　12,660　　12,680　　12,700　　12,720

PsrI

```
ggccgaagctggccgcggaccgaattcccatggagtcaaagattcaaatagaggacctaacagaactcgccgtaaagactggcgaacagttcatacagagtctctta
ccggcttcgaccggcgcctggcttaagggtacctcagtttctaagttatctcctggattgtcttgagcggcatttctgaccgcttgtcaagtatgtctcagagaat
```
`polylinker` | `35s pro`

12,740　　12,760　　12,780　　12,800　　12,820　　12,840

```
cgactcaatgacaagaagaaaatcttcgtcaacatggtggagcacgacacgcttgtctactccaaaaatatcaaagatacagtctcagaagaccaaagggcaattga
gctgagttactgttcttcttttagaagcagttgtaccacctcgtgctgtgcgaacagatgaggttttttatagtttctatgtcagagtcttctggttttcccgttaact
```
`35s pro`

12,860　　12,880　　12,900　　12,920　　12,940

```
gacttttcaacaaagggtaatatccggaaacctcctcggattccattgcccagctatctgtcactttattgtgaagatagtggaaaaggaaggtggctcctacaaat
ctgaaaagttgtttcccattataggcctttggaggagcctaaggtaacgggtcgatagacagtgaaataacacttctatcaccttttccttccaccgaggatgttta
```
`35s pro`

12,960　　12,980　　13,000　　13,020　　13,040

PshAI

```
gccatcattgcgataaaggaaaggccatcgttgaagatgcctctgccgacagtggtcccaaagatggaccccacccacgaggagcatcgtggaaaaagaagacgtt
cggtagtaacgctatttcctttccggtagcaacttctacggagacggctgtcaccagggtttctacctgggggtgggtgctcctcgtagcaccttttcttctgcaa
```
`35s pro`

```
ctatctctctctataataatgtgtgagtagttcccagataagggaattagggttcttataggggtttcgctcatgtgttgagcatataagaaacccttagtatgtatt
gatagagagagatattattacacactcatcaagggtctattcccttaatcccaagaatatcccaaagcgagtacacaactcgtatattctttgggaatcatacataa
```
35sTer
13,920    13,940    13,960    13,980    14,000

```
tgtatttgtaaaatacttctatcaataaaatttctaattcctaaaaccaaaatccagggcgagctcgaattcgagctcgagcccgggtggatcctctagagtcgacc
acataaacattttatgaagatagttatttttaaagattaaggattttggttttaggtcccgctcgagcttaagctcgagctcgggcccacctaggagatctcagctgg
```
35sTer                                          polylinker
14,020    14,040    14,060    14,080    14,100    14,120

AscI
```
tgcagaagcttcggtccggcgcgcctctagttgaagacacgttcatgtcttcatcgtaagaagacactcagtagtcttcggccagaatggcctaactcaaggccatc
acgtcttcgaagccaggccgcgcggagatcaacttctgtgcaagtacagaagtagcattcttctgtgagtcatcagaagccggtcttaccggattgagttccggtag
```
polylinker
14,140    14,160    14,180    14,200    14,220

BspQI
SapI         PmeI
```
gtggcctcttgctcttcaggatgaagagctatgtttaaacgtgcaagcgctactagacaattcagtacattaaaaacgtccgcaatgtgttattaagttgtctaagc
caccggagaacgagaagtcctacttctcgatacaaatttgcacgttcgcgatgatctgttaagtcatgtaattttgcaggcgttacacaataattcaacagattcg
```
polylinker                    Ti plasmid region
14,240    14,260    14,280    14,300    14,320

BlpI
```
gtcaatttggaacaagtggctatcgccagatataagaacttcgatccgaaatatcgtttcaaaactagaaaacagcgcggctttggctaagccgcgcactatatagg
cagttaaaccttgttcaccgatagcggtctatattcttgaagctaggctttatagcaaagttttgatcttttgtcgcgccgaaaccgattcggcgcgtgatatatcc
```
Junction
LB T-DNA border          3' flanking region:Chr1:15191929..15194301
14,340    14,360    14,380    14,400    14,420    14,440

```
attttgggcacctttttgatggaacgtgaaagcgtactgcgcactagttatttaggttgaaccttggatatacggttctcactgcgccaatgcaaggcttgaaacttg
taaaacccgtggaaaactaccttgcactttcgcatgacgcgtgatcaataaatccaacttggaacctatatgccaagagtgacgcggttacgttccgaactttgaac
```
3' flanking region:Chr1:15191929..15194301
14,460    14,480    14,500    14,520    14,540

SnaBI
```
gttagtaatacgtactccctccgtttcttttttatttgtcgctggatagtgcaattttgcactatcgagcgacaaataaaaagaaacggagggagtatatgattgtca
caatcattatgcatgagggaggcaaagaaaaataaacagcgacctatcacgttaaaacgtgatagctcgctgtttattttttctttgcctccctcatatactaacagt
```
3' flanking region:Chr1:15191929..15194301
14,560    14,580    14,600    14,620    14,640

FIG. 1S

```
gatgtagatatgtttattttatatatcacatacagatatataaaacagatcacttttcagatatacagttccaatgtcagccctgatcaccctgtcataaattgcac
ctacatctatacaaataaatatatagtgtatgtctatatattttgtctagtgaaaaagtctatatgtcaaggttacagtcgggactagtgggacagtatttaacgtg
```
3' flanking region:Chr1:15191929..15194301

14,680  14,700  14,720  14,740  14,760

```
gtttctaattgatgttgcttcatggtcgtcatgagaaccttctgaagaaatcgatgaaggttgccaacctttcaaagtttcagaaaccactttgcatgtacactaag
caaagattaactacaacgaagtaccagcagtactcttggaagacttctttagctacttccaacggttggaaagtttcaaagtctttggtgaaacgtacatgtgattc
```
3' flanking region:Chr1:15191929..15194301

14,780  14,800  14,820  14,840  14,860

```
ggctggtttggcagcccaaaaccagccagcgttttcctggtctttctcccgggagaaagcccatgcatagattgtccctggattatttatctgtgtcctttggcta
ccgaccaaaccgtcgggttttggtcggtcgcaaaaggaccagaaaagagggccctctttcgggtacgtatctaacagggacctaataaatagacacaggaaaccgat
```
3' flanking region:Chr1:15191929..15194301

14,880  14,900  14,920  14,940  14,960  14,980

```
aaaattcgtcccaatttcctgtaggaaactacctcggccttggggaggccaggcgattctccaccgcctcgtcgtccatccttcgatgctcacgcgtgcctcctcg
ttttaagcagggttaaaggacatcctttgatggagccggaaccctccggtccgctaagaggtggcggagcagagcaggtaggaagctacgagtgcgcacggaggagc
```
3' flanking region:Chr1:15191929..15194301

15,000  15,020  15,040  15,060  15,080

```
gatgctatcctcaggcgattctccgtcgtctcgtctcatccatcctcacgcgcgcctcctccgacgctatccccaggcgattctccaccgtctcgtctcatccatcc
ctacgataggagtccgctaagaggcagcagagcagagtaggtaggagtgcgcgcggaggaggctgcgatagggtccgctaagaggtggcagagcagagtaggtagg
```
3' flanking region:Chr1:15191929..15194301

15,100  15,120  15,140  15,160  15,180

MauBI
```
tcatgtacgcctcgtccgatgctatccccagacgattttccgtcgtctcatctccttcatgctcgcgcgcgcctcctccgacgctatccccaggcgattttttctgcc
agtacatgcggagcaggctacgataggggtctgctaaaaggcagcagagtagaggaagtacgagcgcgcgcggaggaggctgcgataggggtccgctaaaaagacgg
```
3' flanking region:Chr1:15191929..15194301

15,200  15,220  15,240  15,260  15,280  15,300

MauBI
```
gtctcgtctccttcatgcccgcgcgcgcctcctccgacgctatccccaggcgattttccgccgtctcgtctccttcatgcccgcgcgtgcctcctccgacgctattc
cagagcagaggaagtacgggcgcgcgcggaggaggctgcgataggggtccgctaaaaggcggcagagcagaggaagtacgggcgcgcacggaggaggctgcgataag
```
3' flanking region:Chr1:15191929..15194301

15,320  15,340  15,360  15,380  15,400

```
ccacgagcgcctccgccgccgctatccccagacgattttccgctgtctcgtctccttcatgcccgcgcgccctcctccgacgctatccccacgagcgcctccgccg
ggtgctcgcggaggcggcggcgataggggtctgctaaaaggcgacagagcagaggaagtacgggcgcgcgggaggaggctgcgataggggtgctcgcggaggcggc
```
3' flanking region:Chr1:15191929..15194301

15,420  15,440  15,460  15,480  15,500

FIG. 1T

```
ccgctccaccgtcttccccgccgccatcccct taattcctatagatctggaccccgctctactttcgttggcatacttttgcttggtgtgcgcgggctggagtggaa
ggcgaggtggcagaaggggcggcggtaggggaattaaggatatctagacctggggcgagatgaaagcaaccgtatgaaaacgaaccacacgcgcccgacctcacctt
```

3' flanking region:Chr1:15191929..15194301

15,520    15,540    15,560    15,580    15,600    15,620

```
ggttgcgcattcgatcacgggggagaagtggatcttgggtcttggcaggctagggcggttgccaggacgccgtggtgtgcattcatgggtcctataaatctttatca
ccaacgcgtaagctagtgccccctcttcacctagaacccagaaccgtccgatcccgccaacggtcctgcggcaccacacgtaagtacccaggatatttagaaatagt
```

3' flanking region:Chr1:15191929..15194301

15,640    15,660    15,680    15,700    15,720

AvrII
```
ttaccgccttaggagctagttgtagttcacacatcatatcctttctgctcgacatcgtctggggatgccctaggtgccctaccgaccctacggcattgtcttgacc
aatggcggaatcctcgatcaacatcaagtgtgtagtataggaaaagacgagctgtagcagaccccctacggatccacgggatggctgggatgccgtaacagaactgg
```

3' flanking region:Chr1:15191929..15194301

15,740    15,760    15,780    15,800    15,820

```
tctattagactctatgtcatctagagccttcttgggtggccttttgaccccaaagcgaccctatgatcttaccctaacgaggtctcccttggtggggcaagatccac
agataatctgagatacagtagatctcggaagaacccaccggaaaactggggtttcgctgggatactagaatgggattgctccagagggaaccacccgttctaggtg
```

3' flanking region:Chr1:15191929..15194301

15,840    15,860    15,880    15,900    15,920    15,940

```
tttgtccacttaactgaagatctgatcctcatcttgaaatctttaatcccaaggtgactctacgtcgtatgtggatgctccgggtaacctgccaacccggatcaccc
aaacaggtgaattgacttctagactaggagtagaactttagaaattagggttccactgagatgcagcatacacctacgaggcccattggacggttgggcctagtggg
```

3' flanking region:Chr1:15191929..15194301

15,960    15,980    16,000    16,020    16,040

```
taagatctctttcctaaggggcgagatctaggttcctacgagaaagaagacgaccctgcaccattgcggtccgtccggtccagagtgcgaacgtccggatgcgacac
attctagagaaaggattccccgctctagatccaaggatgctctttcttctgctgggacgtggtaacgccaggcaggccaggtctcacgcttgcaggcctacgctgtg
```

3' flanking region:Chr1:15191929..15194301

16,060    16,080    16,100    16,120    16,140

```
agggaaggagtcgctcctgcagcgaggtcgcagactgtccacacagcctcagaaggcaccgccagacaatacatgtaatacccactctgtaagaaaaacctaaaagg
tcccttcctcagcgaggacgtcgctccagcgtctgacaggtgtgtcggagtcttccgtggcggtctgttatgtacattatgggtgagacattcttttttggattttcc
```

3' flanking region:Chr1:15191929..15194301

16,160    16,180    16,200    16,220    16,240    16,260

```
agaaagtatattcctttatctatatgtgtgttatatttctactcaccatcacatgtgaacatctcacttacacaaataaataattaacaaaagacactcaaataaat
tctttcatataaggaaatagatatacacacaatataaagatgagtggtagtgtacacttgtagagtgaatgtgtttatttattaattgttttctgtgagtttattta
```

3' flanking region:Chr1:15191929..15194301

16,280    16,300    16,320    16,340    16,360

FIG. 1U

```
tatgcatcatgctcgaccttattttgtgtgcattctgttacaatataaaaataatataaaaaacatatattaatatcaaaatttggagatttaaccctaatatgcaa
atacgtagtacgagctggaataaaacacacgtaagacaatgttatattttttattatattttttgtatataattatagttttaaacctctaaattgggattatacgtt
```
⟫━━━━━━━━━━━━━━━━━━━━━━3' flanking region:Chr1:15191929..15194301━━━━━━━━━━━━━━━━━━━━━━⟫
┬──────────────┬──────────────┬──────────────┬──────────────┬──────────────
16,380        16,400         16,420         16,440         16,460

```
atcggagtttagaggaaagaaagaaaaatgctatacaaaataaaggaataaatatataaataaaggtaaaactattaatactggtatattaatttgaacagttgacc
tagcctcaaatctcctttctttctttttacgatatgttttatttccttatttatatatttatttccattttgataattatgaccatataattaaacttgtcaactgg
```
⟫━━━━━━━━━━━━━━━━━━━━━━3' flanking region:Chr1:15191929..15194301━━━━━━━━━━━━━━━━━━━━━━⟫
┬──────────────┬──────────────┬──────────────┬──────────────┬──────────────┬──────────────
16,480        16,500         16,520         16,540         16,560         16,580

```
taattatgaatatcacaactggtttgaattcaaatatgaaatccaagaatttggaaataggaaaaatggagataagaataaaggaaaagaattcttaactcggatgg
attaatacttatagtgttgaccaaacttaagtttatactttaggttcttaaacctttatccttttttacctctattcttatttccttttcttaagaattgagcctacc
```
⟫━━━━━━━━━━━━━━━━━━━━━━3' flanking region:Chr1:15191929..15194301━━━━━━━━━━━━━━━━━━━━━━⟫
┬──────────────┬──────────────┬──────────────┬──────────────┬──────────────
16,600        16,620         16,640         16,660         16,680

```
gcctgggaaacgaatttcggcccacttcctgtgtccttagctgtgcggctcagtccagtg
cggaccctttgcttaaagccgggtgaaggacacaggaatcgacacgccgagtcaggtcac
```
⟫━━━━━━━━3' flanking region:Chr1:15191929..15194301━━━━━━━━⟩
┬──────┬──────┬──────┬──────┬──────┬──────
16,700  16,710  16,720  16,730  16,740  16,750

FIG. 1V

INIR6 TRANSGENIC MAIZE

REFERENCE TO SEQUENCE LISTING SUBMITTED ELECTRONICALLY

The sequence listing contained in the file named "10086US2_ST25.txt", which was electronically filed on Dec. 14, 2021, is incorporated herein by reference in its entirety.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An examples of a selected transgenic corn event which confers lepidopteran and coleopteran insect pest tolerance is the DP-4114 transgenic maize event disclosed in U.S. Pat. No. 8,575,434. DP-4114 transgenic maize plants express a Cry1F protein which can confer resistance to European corn borer (ECB, *Ostrinia nubilalis*) infestations as well as cry34Ab1 and cry35Ab1 proteins which can confer resistance to corn rootworm (CRW; *Diabrotica* sp. Including *Diabrotica virgifera virgifera*) infestations. DP-4114 transgenic maize plants also express a phosphinotricin acetyl transferase (PAT) protein which confers tolerance to the herbicide glufosinate.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic maize plant cells comprising an INIR6 transgenic locus comprising an originator guide RNA recognition site (OgRRS) in a first DNA junction polynucleotide of a DP-4114 transgenic locus and a cognate guide RNA recognition site (CgRRS) in a second DNA junction polynucleotide of the DP-4114 transgenic locus are provided. Transgenic maize plant cells comprising an INIR6 transgenic locus comprising an insertion and/or substitution in a DNA junction polynucleotide of a DP-4114 transgenic locus of DNA comprising a cognate guide RNA recognition site (CgRRS) are provided. In certain embodiments, the DP-4114 transgenic locus is set forth in SEQ ID NO:1, is present in seed deposited at the ATCC under accession No. PTA-11506 is present in progeny thereof, is present in allelic variants thereof, or is present in other variants thereof. INIR6 transgenic maize plant cells, transgenic maize plant seeds, and transgenic maize plants all comprising a transgenic locus set forth in SEQ ID NO: 20 are provided. Transgenic maize plant parts including seeds and transgenic maize plants comprising the maize plant cells are also provided.

Methods for obtaining a bulked population of inbred seed comprising selfing the aforementioned transgenic maize plants and harvesting seed comprising the INIR6 transgenic locus from the selfed maize plant are also provided.

Methods of obtaining hybrid maize seed comprising crossing the aforementioned transgenic maize plants to a second maize plant which is genetically distinct from the first maize plant and harvesting seed comprising the INIR6 transgenic locus from the cross are provided. Methods for obtaining a bulked population of seed comprising selfing a transgenic maize plant of comprising SEQ ID NO: 20 and harvesting transgenic seed comprising the transgenic locus set forth in SEQ ID NO: 20 are provided.

A DNA molecule comprising SEQ ID NO: 2, 3, 8, 9, 10, 19, or 20 is provided. Processed transgenic maize plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a maize plant cell comprising the INIR6 transgenic locus of any one of claims 1 to 3, comprising the step of detecting a DNA molecule comprising SEQ ID NO: 2, 3, 8, 9, 10, 19, or 20 are provided.

Methods of excising the INIR6 transgenic locus from the genome of the aforementioned maize plant cells comprising the steps of: (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR6 transgenic locus flanked by the OgRRS and the CgRRS has been excised.

BRIEF DESCRIPTION OF THE DRAWINGS/FIGURES

FIG. 1A-W shows a sequence (SEQ ID NO: 1) of the DP-4114 event transgenic locus including the genomic DNA and 5' and 3' junction sequences flanking the inserted transgenic DNA as well as a diagram of transgene expression cassettes and selectable markers in the transgenic locus.

Figure 2:
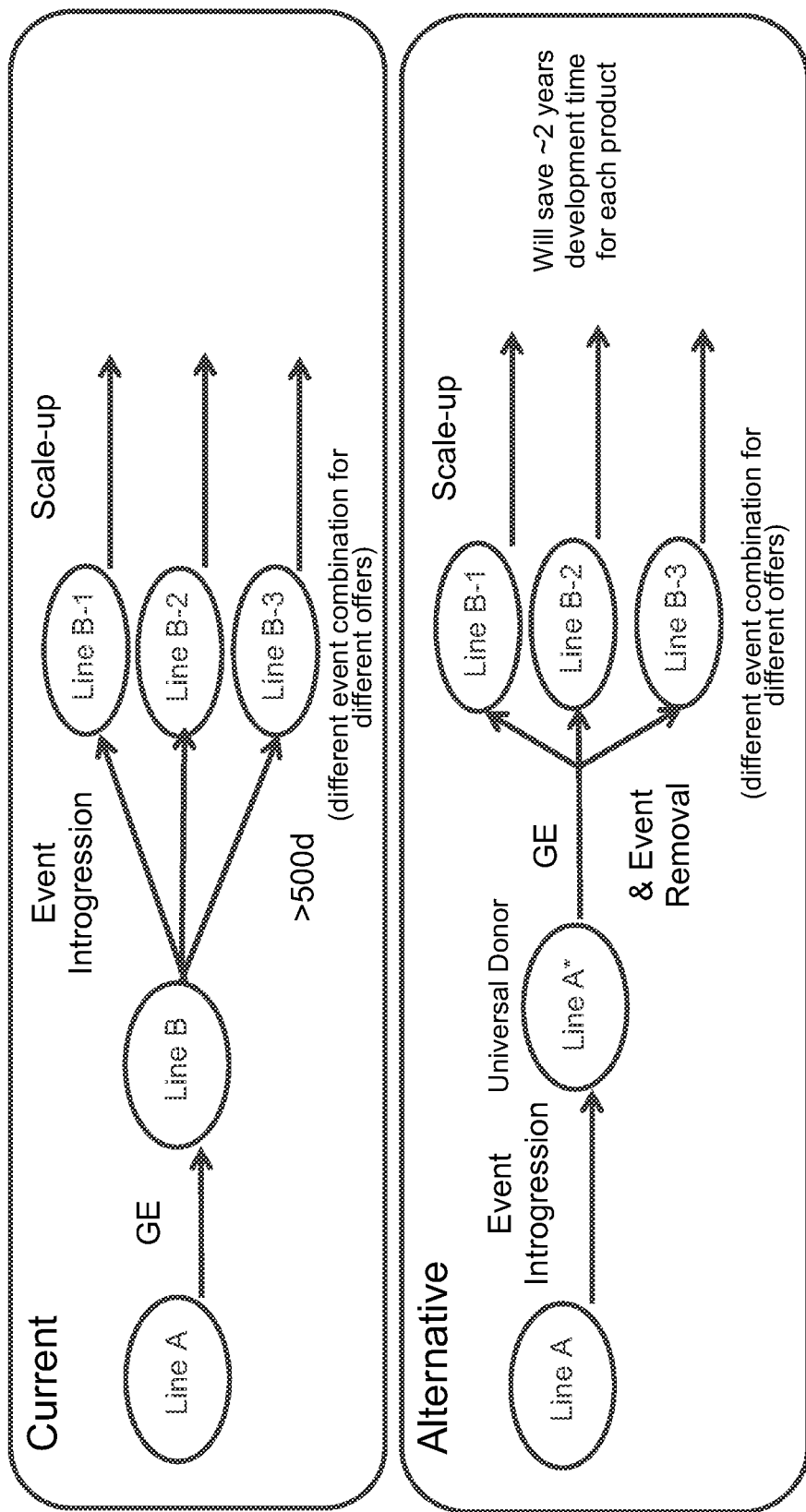

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules and "Event Removal" refers to excision of a transgenic locus (i.e., an "Event") with genome editing molecules.

Figure 3A:
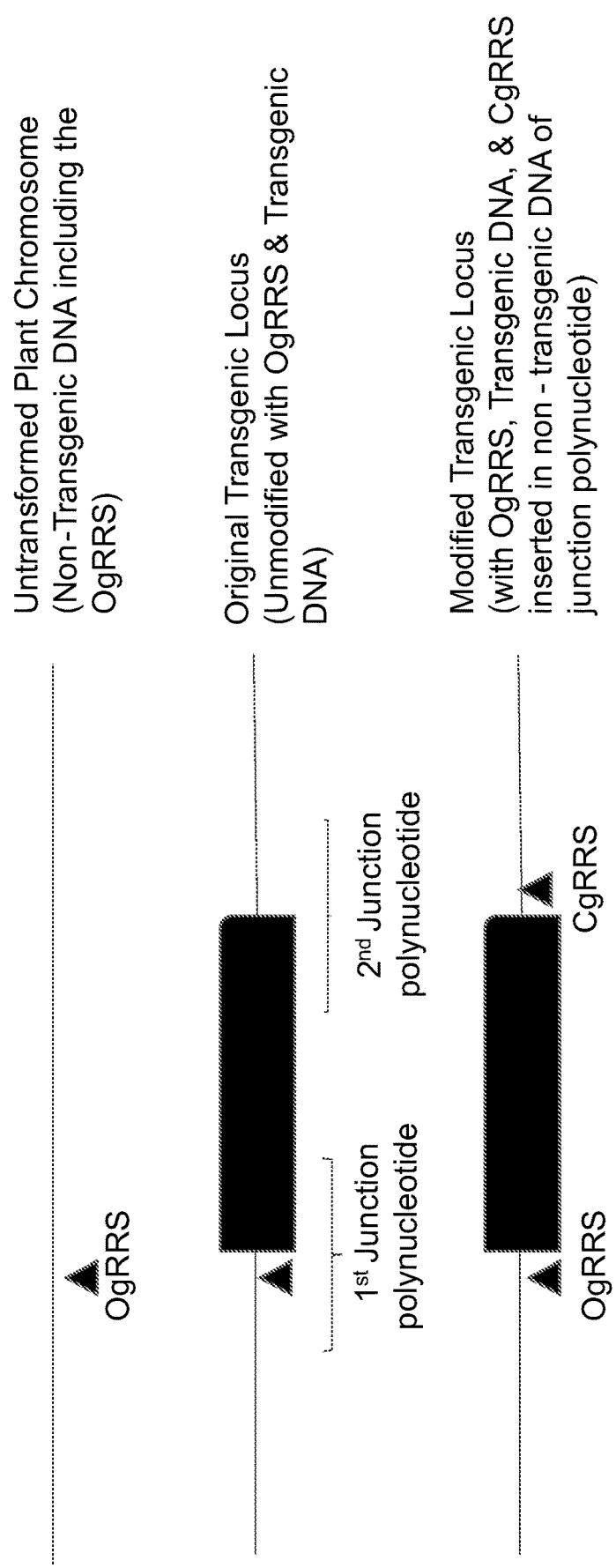
Figure 38:
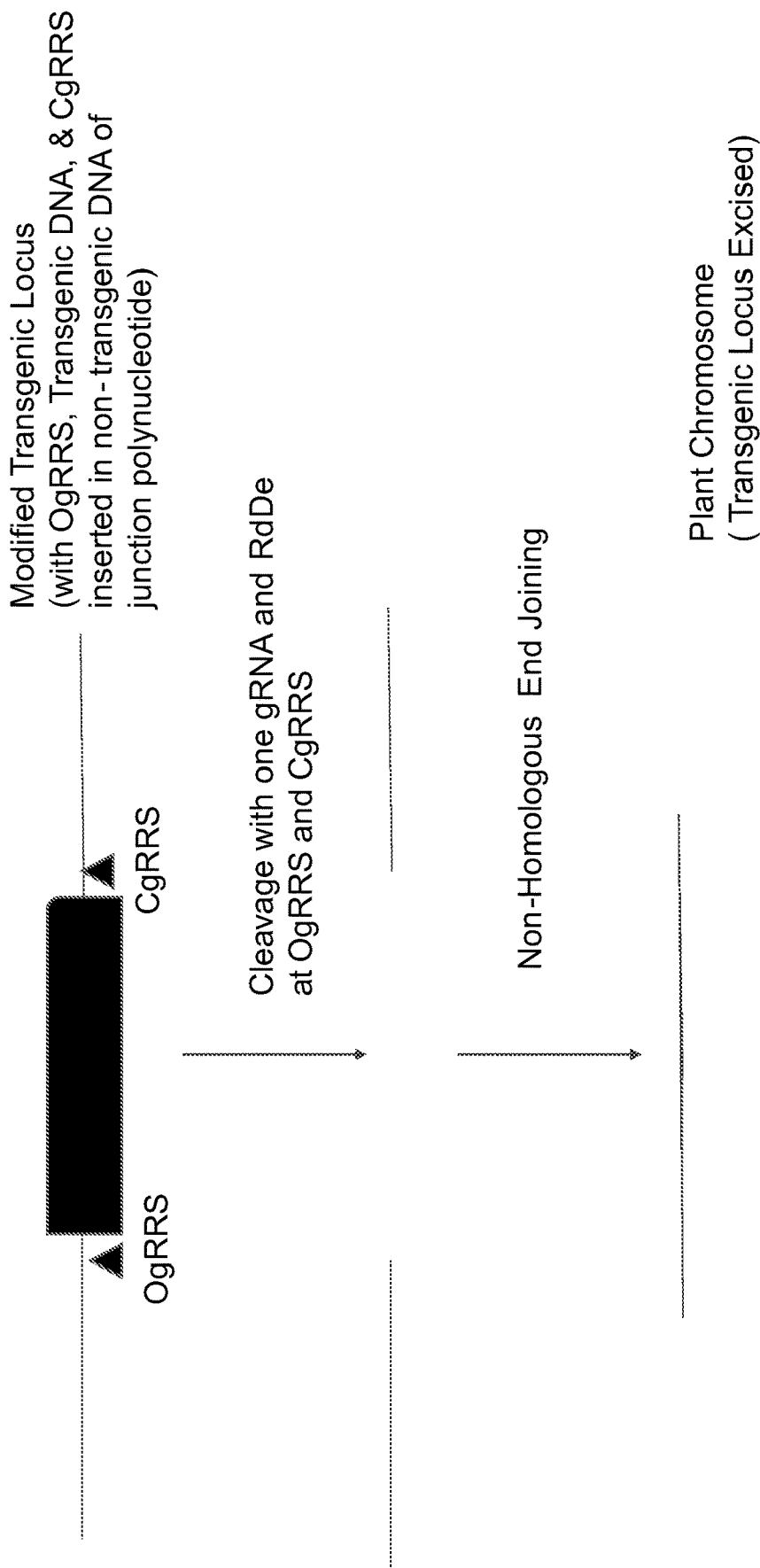

FIG. 3A, B. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the st junction polynucleotide (middle); and (iii) the modified transgenic locus with a cognate guide RNA inserted into the non-transgenic DNA of the $2^{nd}$ junction polynucleotide (bottom). FIG. 3B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 21.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "DP-4114" is used to refer to any of a transgenic maize locus, transgenic maize plants and parts thereof including seed set forth in U.S. Pat. No. 8,575,434, which is incorporated herein by reference in its entirety. Representative DP-4114 transgenic maize seed have been deposited with American Type Culture Collection (ATCC, Manassas, Va. 20110-2209 USA) under Accession No. PTA-11506. DP-4114 transgenic loci include loci having the sequence of SEQ ID NO:1, the sequence of the DP-4114 locus in the deposited seed of Accession No. PTA-11506 and any progeny thereof, as well as allelic variants and other variants of SEQ ID NO:1

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR6" is used to refer either individually collectively to items that include any or all of the DP-4114 transgenic maize loci which have been modified as disclosed herein, modified DP-4114 transgenic maize plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as maize and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INIR6 transgenic loci provided here are characterized by polynucleotide sequences that can facilitate as necessary the removal of the INIR6 transgenic loci from the genome. Useful applications of such INIR6 transgenic loci and related methods of making include targeted excision of a INIR6 transgenic locus or portion thereof in certain breeding lines to facilitate recovery of germplasm with subsets of transgenic traits tailored for specific geographic locations and/or grower preferences. Other useful applications of such INIR6 transgenic loci and related methods of making include removal of transgenic traits from certain breeding lines when it is desirable to replace the trait in the breeding line without disrupting other transgenic loci and/or non-transgenic loci. In certain embodiments, maize genomes containing INIR6 transgenic loci or portions thereof which can be selectively excised with one or more gRNA molecules and RdDe (RNA dependent DNA endonucleases) which form gRNA/target DNA complexes. Such selectively excisable INIR6 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present injunction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found injunction sequences of transgenic plants containing an unmodified transgenic locus. Examples of OgRRS polynucleotide sequences in or near a 5' junction polynucleotide in an DP-4114 transgenic locus include SEQ ID NO: 7. OgRRS polynucleotide sequences located in a first junction polynucleotide can be introduced into the second junction polynucleotide using donor DNA templates as illustrated in FIG. 3C and as elsewhere described herein. A donor DNA template for introducing the SEQ ID NO: 7 OgRRS into the 3' junction polynucleotide of an DP-4114 locus includes the donor DNA template formed by annealing SEQ ID NO: 11 and 12 or by annealing SEQ ID NO: 11 and 13. Double stranded breaks in a 3' junction polynucleotide of SEQ ID NO: 1 can be introduced with gRNAs encoded by SEQ ID NO: 4, 5, and/or 6 and a Cas12a nuclease. Integration of the SEQ ID NO: 11/12 or 11/13 donor DNA template into the 3' junction polynucleotide of an DP-4114 locus at the double stranded breaks introduced by the gRNAs encoded by SEQ ID NO: 4, 5, and/or 6 and a Cas12a nuclease can provide an INIR6 locus comprising the CgRRS sequence set forth in SEQ ID NO: 8, 9, or 10. Double stranded breaks in a 3' junction polynucleotide of SEQ ID NO: 1 can be introduced with gRNAs encoded by SEQ ID NO: 4, 5, and/or 6. Another donor DNA template adapted for insertion of the OgRRS of SEQ ID NO: 7 in a 3' junction polynucleotide of a DP-4114 transgenic locus can comprise SEQ ID NO: 14. Double stranded breaks in a 3' junction polynucleotide of SEQ ID NO: 1 can be introduced with gRNAs encoded by SEQ ID NO: 5 and a Cas12a nuclease. A donor DNA template of SEQ ID NO: 14 or the equivalent thereof having longer or shorter homology arms can be used to obtain the CgRRS insertion in the 3' junction polynucleotide that is set forth in SEQ ID NO: 19. An INIR6 transgenic locus containing this CgRRS insertion is set forth in SEQ ID NO: 20.

Also provided are unique transgenic locus excision sites created by excision of INIR6 transgenic loci or selectively excisable INIR6 transgenic loci, DNA molecules comprising the INIR6 transgenic loci or unique fragments thereof (i.e., fragments of an INIR6 locus which are not found in an DP-4114 transgenic locus), INIR6 plants comprising the same, biological samples containing the DNA, nucleic acid markers adapted for detecting the DNA molecules, and related methods of identifying maize plants comprising unique INIR6 transgenic locus excision sites and unique fragments of a INIR6 transgenic locus. DNA molecules comprising unique fragments of an INIR6 transgenic locus are diagnostic for the presence of an INIR6 transgenic locus or fragments thereof in a maize plant, maize cell, maize seed, products obtained therefrom (e.g., seed meal or stover), and biological samples.

Figure 1K:
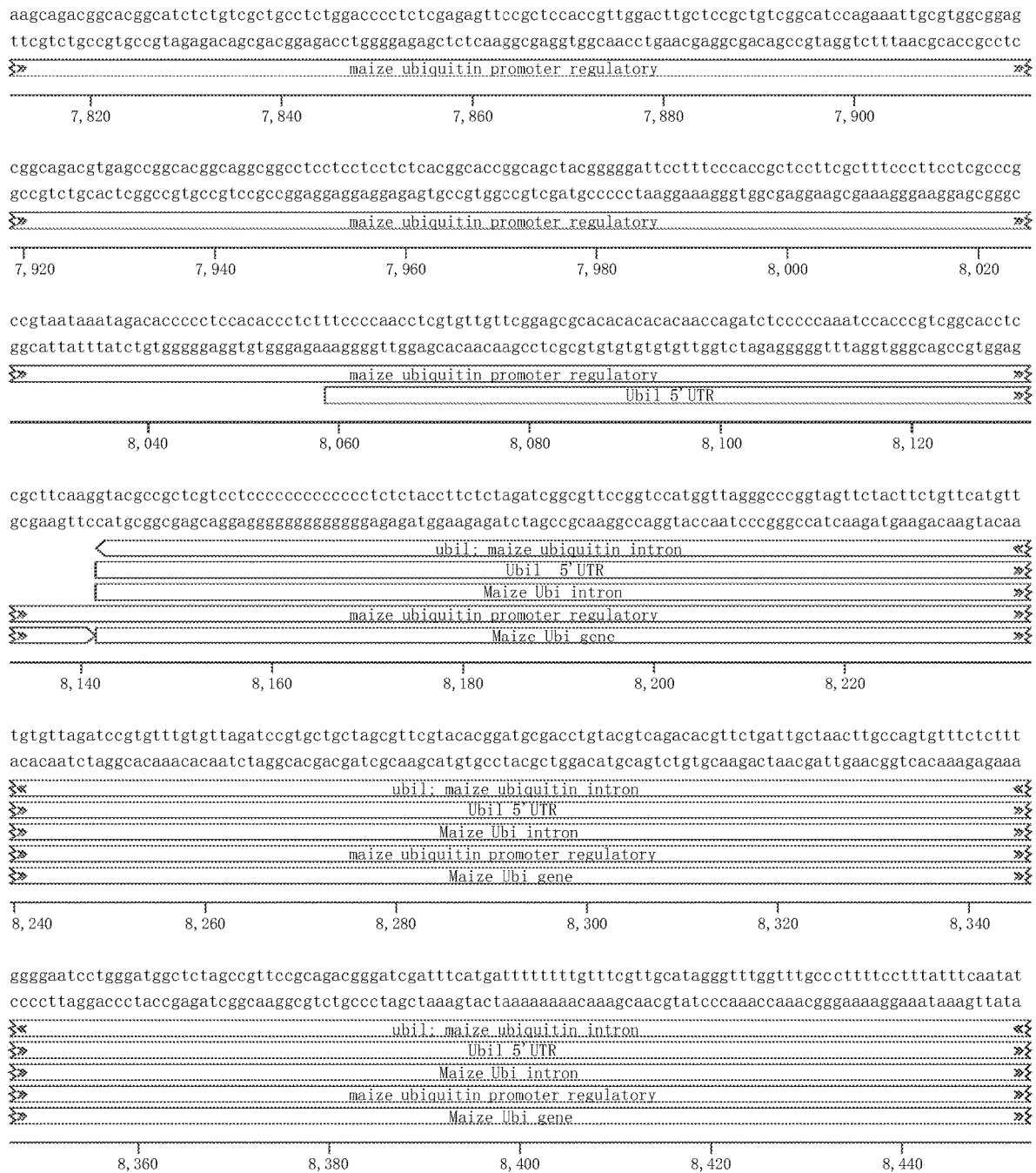
Figure 1M:
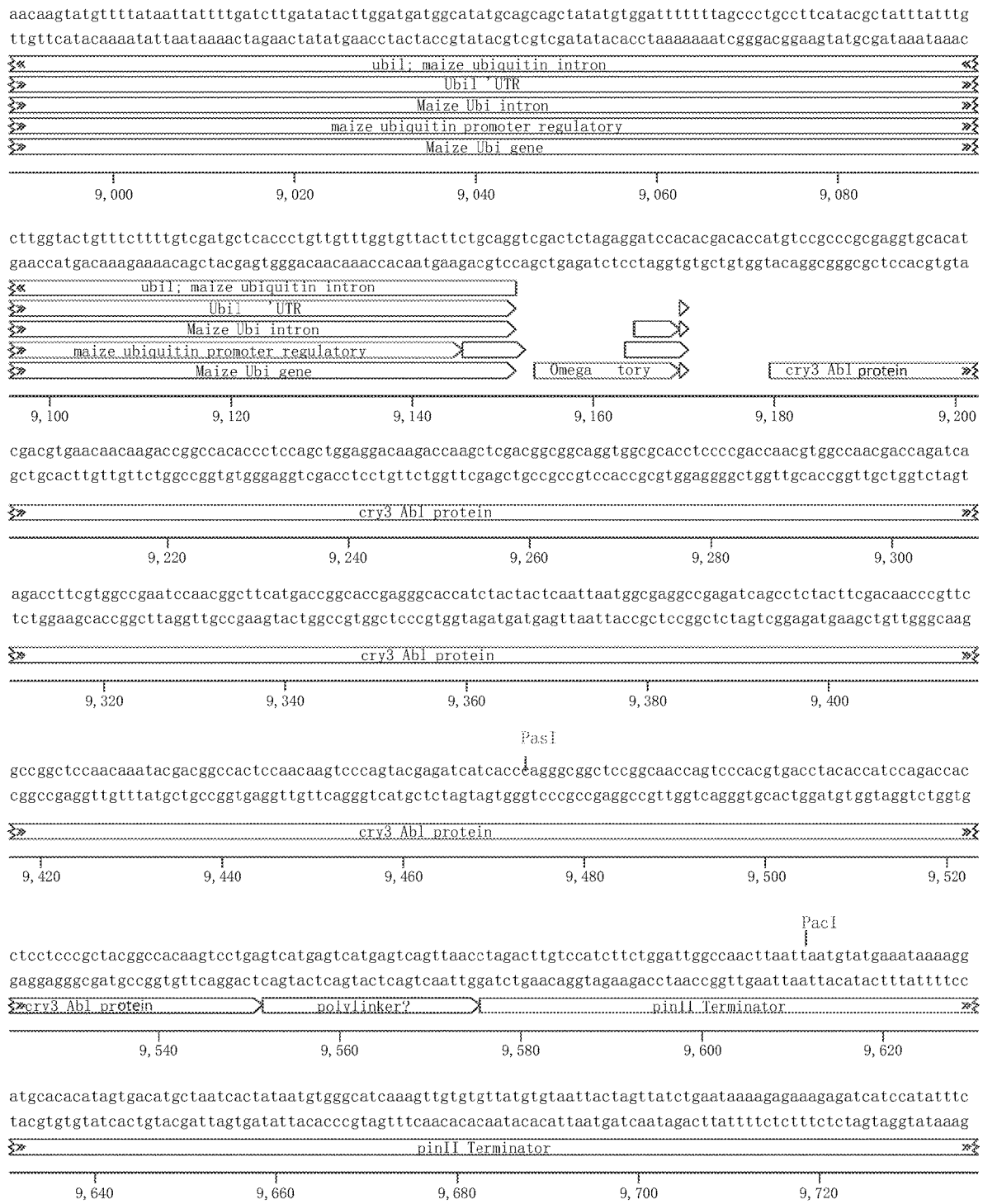
Figure 1R:
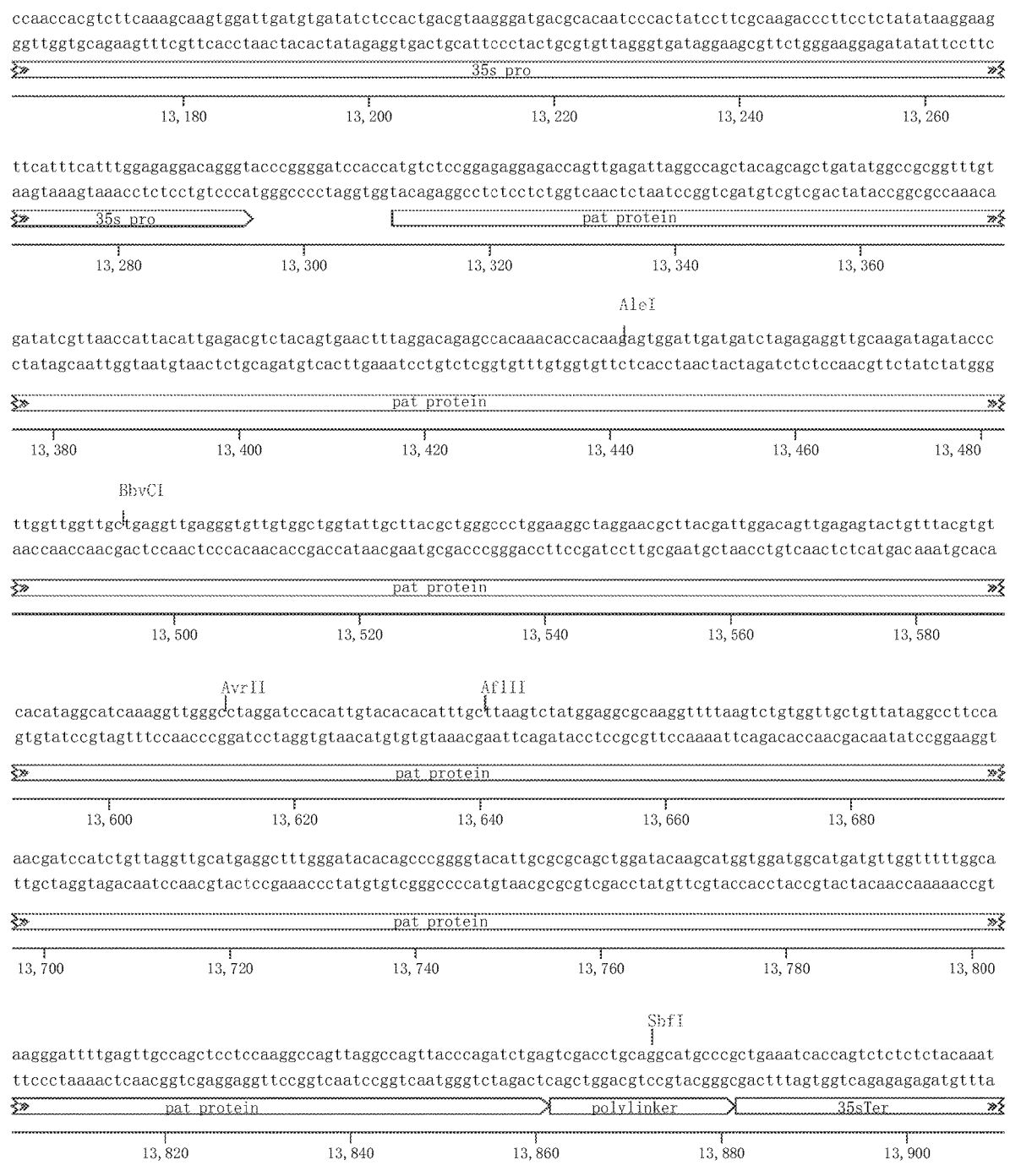
Figure 11B:
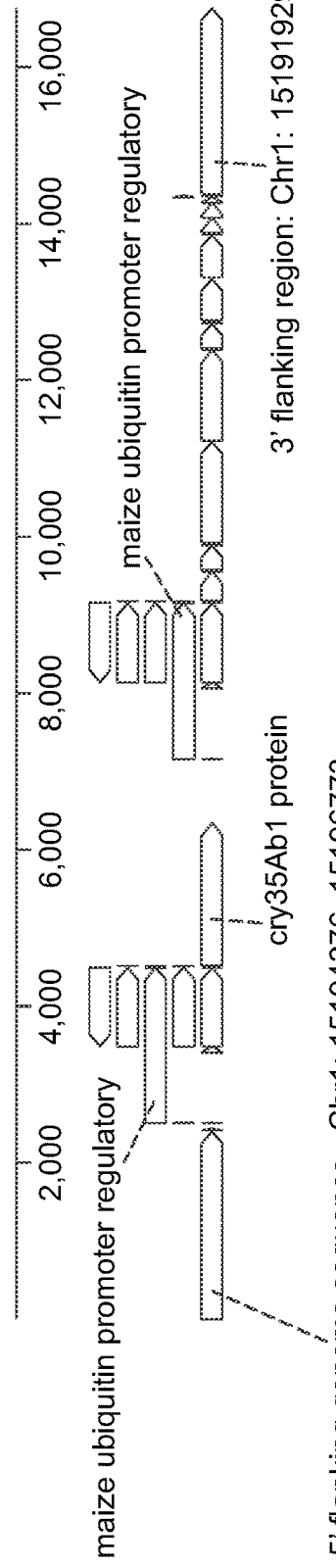

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the maize DP-4114 transgenic locus. The maize DP-4114 transgenic locus and its transgenic junction sequences are also depicted in FIG. 1. Maize plants comprising the DP-4114 transgenic locus and seed thereof have been cultivated, been placed in commerce, and have been described in a variety of publications by various governmental bodies. Databases which have compiled descriptions of the DP-4114 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the DP-4114 transgenic locus which can be improved by the methods provided herein are set forth or otherwise provided in SEQ ID NO: 1, U.S. Pat. No. 8,575,434, the sequence of the DP-4114 locus in the deposited seed of ATCC accession No. PTA-11506, and elsewhere in this disclosure. In certain embodiments provided herein, the DP-4114 transgenic locus set forth in SEQ ID NO: 1 or present in the deposited seed of ATCC accession No. PTA-11506 is referred to as an "original DP-4114 transgenic locus." Allelic or other variants of the sequence set forth SEQ ID NO: 1, the patent references set forth therein and incorporated herein by reference in their entireties, and elsewhere in this disclosure which may be present in certain variant DP-4114 transgenic plant loci (e.g., progeny of deposited seed of accession No. PTA-11506 which contain allelic variants of SEQ ID NO:1 or progeny originating from transgenic plant cells comprising the original MIR162 transgenic set forth in U.S. Pat. No. 8,575,434) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, or 10,579 nucleotides of SEQ ID NO: 1. Also provided are plants, plant parts including seeds, genomic DNA, and/or DNA obtained from INIR6 plants which comprise one or more modifications (e.g., via insertion of a CgRRS in a junction polynucleotide sequence) which provide for selective excision of the INIR6 transgenic locus or a portion thereof. Also provided herein are methods of detecting plants, genomic DNA, and/or DNA obtained from plants comprising a INIR6 transgenic locus which contains one or more of a CgRRS, deletions of selectable marker genes, deletions of non-essential DNA, and/or a transgenic locus excision site. A first junction polynucleotide of a DP-4114 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INIR6 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the DP-4114 transgenic locus of SEQ ID NO: 1, allelic variants thereof, or other variants thereof to obtain an INIR6 transgenic locus. In other embodiments, the OgRRS is found in non-transgenic DNA or transgenic DNA of the 3' junction polynucleotide of the DP-4114 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INIR6 transgenic locus.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR6 transgenic locus, in transgenic DNA of a DNA junction polynucleotide of an INIR6 transgenic locus, or can span the junction of the transgenic and non-transgenic DNA of a DNA junction polynucleotide of an INIR6 transgenic locus. An OgRRS can likewise be located in non-transgenic plant genomic DNA of a DNA junction polynucleotide of an INIR6 transgenic locus, in transgenic DNA of a DNA junction polynucleotide of an INIR6 transgenic locus, or can span the junction of the transgenic and non-transgenic DNA of a DNA junction polynucleotide of an INIR6 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR6 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 2) comprising two or more of the modified transgenic loci. This elite germplasm containing the modified transgenic loci (e.g., "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed maize plants comprising the INIR6 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. Techniques for effecting genome editing in crop plants (e.g., maize,) include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in elite crop plant and other germplasm, are set forth in US 20030082813, US 20080134353, US 20090328252, US 20100100981, US 20110165679, US 20140157453, US 20140173775, and US 20170240911, which are each incorporated by reference in their entireties. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR6 transgenic locus comprising an OgRRS in non-transgenic DNA of a 1st junction polynucleotide sequence and a CgRRS in a 2nd junction polynucleotide sequence is deleted with a gRNA and RdDe that recognize the OgRRS and the CgRRS to produce an INIR6 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR6 transgenic loci excision sites are provided herein.

In other embodiments, a segment comprising a INIR6 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a DP-4114 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INIR6 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the maize plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

In certain embodiments, edited transgenic plant genomes provided herein can lack one or more selectable and/or scoreable markers found in an original event (transgenic locus). Original DP-4114 transgenic loci (events), including those set forth in SEQ ID NO: 1), U.S. Pat. No. 8,575,434, the sequence of the DP-4114 locus in the deposited seed of accession No. PTA-11506 and progeny thereof, contain a selectable marker gene encoding a phosphinotricin acetyl transferase (PAT) protein which confers tolerance to the herbicide glufosinate. In certain embodiments provided herein, the DNA element comprising, consisting essentially of, or consisting of the PAT selectable marker gene of an DP-4114 transgenic locus is absent from an INIR6 transgenic locus. The PAT selectable marker cassette can be excised from an original DP-4114 transgenic locus by contacting the transgenic locus with one or more gene editing molecules which introduce double stranded breaks in the transgenic locus at the 5' and 3' end of the expression cassette comprising the PAT selectable marker transgene (e.g., an RdDe and guide RNAs directed to PAM sites located at the 5' and 3' end of the expression cassette comprising the PAT selectable marker transgene) and selecting for plant cells, plant parts, or plants wherein the selectable marker has been excised. In certain embodiments, the selectable or scoreable marker transgene can be inactivated. Inactivation can be achieved by modifications including insertion, deletion, and/or substitution of one or more nucleotides in a promoter element, 5' or 3' untranslated region (UTRs), intron, coding region, and/or 3' terminator and/or polyadenylation site of the selectable marker transgene. Such modifications can inactivate the selectable marker transgene by eliminating or reducing promoter activity, introducing a missense mutation, and/or introducing a pre-mature stop codon. In certain embodiments, the selectable PAT marker transgene can be replaced by an introduced transgene. In certain embodiments, an original transgenic locus that was contacted with gene editing molecules which introduce double stranded breaks in the transgenic locus at the 5' and 3' end of the expression cassette comprising the PAT selectable marker transgene can also be contacted with a suitable donor DNA template comprising an expression cassette flanked by DNA homologous to remaining DNA in the transgenic locus located 5' and 3' to the selectable marker excision site. In certain embodiments, a coding region of the PAT selectable marker transgene can be replaced with another coding region such that the replacement coding region is operably linked to the promoter and 3' terminator or polyadenylation site of the PAT selectable marker transgene.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 3C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 8,575,434, 6,040,497, 8,759,618, 7,157,281, 6,852,915, 7,705,216, 10,316,330, 8,618,358, 8,450,561, 8,212,113, 9,428,765, 7,897,748, 8,273,959, 8,093,453, 8,901,378, 9,994,863, 7,928,296, and 8,466,346, each of which are incorporated herein by reference in their entireties.

In certain embodiments, INIR6 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by example, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif, (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof, (o) a transcription factor binding sequence; and (p) a polycomb response element (see Xiao et al. (2017)

Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wxl (high amylopectin content; US 20190032070; incorporated herein by reference in its entirety); (e) TMS5 (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including maize which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abbl400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) *Science*, 339:819-823; Ran et al. (2013) *Nature Protocols*, 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell*, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science*, 339:819-823; Xing et al. (2014) *BMC Plant Biol.*, 14:327-340. Chemically modified sgRNAs have been demonstrated to be effective in genome editing; see, for example, Hendel et al. (2015) *Nature Biotechnol.*, 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) *Nature*, 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., *Sci Adv.* 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) *Nature* 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) *Nature Rev. Genet.*, 11:636-646; Mohanta et al. (2017) *Genes* vol. 8, 12: 399; Ramirez et al. Nucleic Acids Res. (2012); 40(12): 5560-5568; Liu et al. (2013) *Nature Communications*, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010) *J. Mol. Biol.*, 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes* vol. 8, 12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 14 and equivalents thereof with longer or shorter homology arms. In certain embodiments, a donor DNA template can comprise an adapter molecule (e.g., a donor DNA template formed by annealing SEQ ID NO: 11 and 12 or by annealing SEQ ID NO: 11 and 13) with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an E. coli SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide.

Various treatments are useful in delivery of gene editing molecules and/or other molecules to a DP-4114 or INIR6 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature,* 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a DP-4114 or INIR6 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferre-D'Amare and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from maize, tomato, or soybean such as those disclosed U.S. Patent Application Publication 2017/0166912, or a homologue thereof, in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA, and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the DP-4114 or INIR6 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol [dot]pdf; (Ravi et al. (2014) *Nature Communications,* 5:5334, doi: 10.1038/ncomms6334). Haploids can also be obtained in a wide variety of monocot plants (e.g., maize, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the DP-4114 or INIR6 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the DP-4114 or INIR6 plant cells in used in the methods provided herein can include dividing cells. Dividing cells can include those cells found in various plant tissues including leaves, meristems, and embryos. These tissues include dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR6 plant from a INIR6 plant cell that had been subjected to the gene editing or from a regenerable plant structure obtained from that INIR6 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR6 plant or its seeds, including: (a) maize seed meal (defatted or non-defatted); (b) extracted proteins, oils, sugars, and starches; (c) fermentation products; (d) animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

EMBODIMENTS

Various embodiments of the plants, genomes, methods, biological samples, and other compositions described herein are set forth in the following sets of numbered embodiments.

1a. A transgenic maize plant cell comprising an INIR6 transgenic locus comprising an originator guide RNA recognition site (OgRRS) in a first DNA junction polynucleotide of a DP-4114 transgenic locus and a cognate guide RNA recognition site (CgRRS) in a second DNA junction polynucleotide of the DP-4114 transgenic locus.

1b. A transgenic maize plant cell comprising an INIR6 transgenic locus comprising an insertion and/or substitution of DNA in a DNA junction polynucleotide of a DP-4114 transgenic locus with DNA comprising a cognate guide RNA recognition site (CgRRS).

2. The transgenic maize plant cell of embodiment 1a or 1b, wherein said CgRRS comprises the DNA molecule set forth in SEQ ID NO: 8, 9, 10, or 19; and/or wherein said DP-4114 transgenic locus is set forth in SEQ ID NO:1, is present in seed deposited at the ATCC under accession No. PTA-11506. is present in progeny thereof, is present in allelic variants thereof, or is present in other variants thereof.

3. The transgenic maize plant cell of embodiments 1a, 1b, or 2, wherein said INIR6 transgenic locus comprises the DNA molecule set forth in SEQ ID NO: 2, 3, or 20.

4. A transgenic maize plant part comprising the maize plant cell of any one of embodiments 1a, 1b, 2, or 3, wherein said maize plant part is optionally a seed.

5. A transgenic maize plant comprising the maize plant cell of any one of embodiments 1a, 1b, 2, or 3.

6. A method for obtaining a bulked population of inbred seed comprising selfing the transgenic maize plant of embodiment 5 and harvesting seed comprising the INIR6 transgenic locus from the selfed maize plant.

7. A method of obtaining hybrid maize seed comprising crossing the transgenic maize plant of embodiment 5 to a second maize plant which is genetically distinct from the first maize plant and harvesting seed comprising the INIR6 transgenic locus from the cross.

8. A DNA molecule comprising SEQ ID NO: 2, 3, 8, 9, 10, 19, or 20.

9. A processed transgenic maize plant product comprising the DNA molecule of embodiment 8.

10. A biological sample containing the DNA molecule of embodiment 8.

11. A nucleic acid molecule adapted for detection of genomic DNA comprising the DNA molecule of embodiment 8, wherein said nucleic acid molecule optionally comprises a detectable label.

12. A method of detecting a maize plant cell comprising the INIR6 transgenic locus of any one of embodiments 1a, 1b, 2, or 3, comprising the step of detecting DNA molecule comprising SEQ ID NO: 2, 3, 8, 9, 10, 19, or 20.

13. A method of excising the INIR6 transgenic locus from the genome of the maize plant cell of any one of embodiments 1a, 1b, 2, or 3, comprising the steps of:

(a) contacting the edited transgenic plant genome of the plant cell of embodiment 5 with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR6 transgenic locus flanked by the OgRRS and the CgRRS has been excised.

EXAMPLES

Example 1. Introduction of a CgRRS in a 3' Junction Polynucleotides of a DP-4114 Transgenic Locus Transgenic plant genomes containing one or more of the following transgenic loci (events) are contacted with:
(i) an ABE or CBE and guide RNAs which recognize the indicated target DNA sites (protospacer (guide RNA coding) plus PAM site) in the 5' or 3' junction polynucleotides of the event to introduce a CgRRS in the junction polynucleotide;
(ii) an RdDe and guide RNAs which recognize the indicated target DNA site (guide RNA coding plus PAM site) in the 5' or 3' junction polynucleotides of the event as well as a donor DNA template spanning the double stranded DNA break site in the junction polynucleotide to introduce a CgRRS in a junction polynucleotide.

Plant cells, callus, parts, or whole plants comprising the introduced CgRRS in the transgenic plant genome are selected.

TABLE 1

Examples of OgRRS and CgRRS in DP-4114

| CORN EVENT NAME | OgRRS | CgRRS |
|---|---|---|
| DP-4114 | tttgtagcacttgcacgtagttacccg (SEQ ID NO: 7; located in 5' junction polynucleotide of SEQ ID NO: 1) | cgcttttgtagcacttgcacgtagttacccggata (SEQ ID NO: 8; inserted into 3' junction polynucleotide) |
| | | aacgtgcaagcgcttttgtagcacttgcacgtagttaccc ggatataagaacttcgatccgaaa (SEQ ID NO: 9; inserted into 3' junction polynucleotide) |
| | | aacgtgcaagcgcttttgtagcacttgcacgtagttaccc ggccagatataagaacttcgatccgaaa (SEQ ID NO: 10; inserted into 3' junction polynucleotide) |

Example 2. Insertion of a CgRRS Element in the 3'-Junction of the DP-4114 Event

Two plant gene expression vectors are prepared. Plant expression cassettes for expressing a bacteriophage lambda exonuclease, a bacteriophage lambda beta SSAP protein, and an E. coli SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the E. coli SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by example. DNA sequences encoding the c2 NLS-Exo, c2 NLS lambda beta SSAP, and c2NLS-SSB fusion proteins are operably linked to a OsUB1I, ZmUBI1, OsACT promoter and a OsUbi1, ZmUBI1, OsACT polyadenylation site respectively, to provide the exonuclease, SSAP, and SSB plant expression cassettes.

A DNA donor template sequence (SEQ ID NO: 14) that targets the 3'-T-DNA junction polynucleotide of the DP-4114 event (SEQ ID NO:1; FIG. 1) for HDR-mediated insertion of a 27 base pair OgRRS sequence (SEQ ID NO: 7) that is identical to a Cas12a recognition site at the 5'-junction polynucleotide of the DP-4114 T-DNA insert is constructed. The DNA donor sequence includes a replacement template with desired insertion region (27 base pairs long) flanked on both sides by homology arms about 500-635 bp in length. The homology arms match (i.e., are homologous to) gDNA (genomic DNA) regions flanking the target gDNA insertion site (SEQ ID NO: 15). The replacement template region comprising the donor DNA is flanked at each end by DNA sequences identical to the DP-4114 3'-T-DNA junction polynucleotide sequence recognized by a Cas12a RNA-guided nuclease and a gRNA (e.g., encoded by SEQ ID NO: 5).

A plant expression cassette that provides for expression of the RNA-guided sequence-specific Cas12a endonuclease is constructed. A plant expression cassette that provides for expression of a guide RNA (e.g., encoded by SEQ ID NO: 5) complementary to sequences adjacent to the insertion site is constructed. An *Agrobacterium* superbinary plasmid transformation vector is constructed. Once the cassettes, donor sequence and *Agrobacterium* superbinary plasmid transformation vector are constructed, they are combined to generate two maize transformation plasmids.

A maize transformation plasmid is constructed with the RNA-guided sequence-specific endonuclease cassette, the guide RNA cassette, and the DP-4114 3'-T_DNA junction sequence DNA donor sequence into the *Agrobacterium* superbinary plasmid transformation vector (the control vector).

A maize transformation plasmid is constructed with the RNA-guided sequence-specific endonuclease cassette, the guide RNA cassette, the SSB cassette, the lambda beta SSAP cassette, the Exo cassette, and the DP-4114 3'-T_DNA junction sequence donor DNA template sequence (SEQ ID NO: 14) into the *Agrobacterium* superbinary plasmid transformation vector (the lambda red vector).

All constructs are transformed into *Agrobacterium* strain LBA4404.

Maize transformations are performed based on published methods.

When a sufficient amount of viable tissue is obtained, it can be screened for insertion at the DP-4114 junction sequence, using a PCR-based approach. The PCR primer on the 5'-end is 5'-tacgctgggccctggaaggctagga-3' (SEQ ID NO: 17). The PCR primer on the 3'-end is 5'-gatggacga-gacgaggcggtggaga-3' (SEQ ID NO: 18). The above primers that flank donor DNA homology arms are used to amplify the DP-4114 3'-junction polynucleotide sequence. The correct donor sequence insertion will produce a 1563 bp product. A unique DNA fragment comprising the CgRRS in the DP-4114 3' junction polynucleotide is set forth in SEQ ID NO: 19. Amplicons can be sequenced directly using an amplicon sequencing approach or ligated to a convenient plasmid vector for Sanger sequencing. Those plants in which the DP-4114 junction sequence now contains the intended Cas12a recognition sequence are selected and grown to maturity. The T-DNA encoding the Cas12a reagents can be segregated away from the modified junction sequence in a subsequent generation. The resultant INIR6 transgenic locus (SEQ ID NO: 20) comprising the CgRRS and OgRRS (e.g., which each comprise SEQ ID NO: 7) can be excised using Cas12a and a suitable gRNA which hybridizes to DNA comprising SEQ ID NO: 7 at both the OgRRS and the CgRRS.

The breadth and scope of the present disclosure should not be limited by any of the above-described embodiments.

What is claimed is:

1. A transgenic maize plant cell comprising a modified DP-4114 transgenic locus comprising the sequence of SEQ ID NO: 3.

2. A transgenic maize plant part comprising a modified DP-4114 transgenic locus comprising the transgenic maize plant cell of claim 1.

3. The transgenic maize plant part of claim 2, wherein the transgenic maize plant part is a seed.

4. A transgenic maize plant comprising the transgenic maize plant cell of claim 1.

5. A method for obtaining a bulked population of seed comprising selfing the transgenic maize plant of claim 4 and harvesting transgenic seed comprising the modified DP-4114 transgenic locus comprising the sequence of SEQ ID NO: 3.

6. A method of obtaining hybrid maize seed comprising crossing the transgenic maize plant of claim 4 to a second maize plant which is genetically distinct from the first maize plant and harvesting seed comprising the modified DP-4114 transgenic locus from the cross.

7. A biological sample comprising non-intact plant issue from of the maize plant of claim 4, wherein the non-intact plant tissue comprises milled or chopped plant tissue, and wherein the biological sample comprises the DNA molecule of SEQ ID NO: 10.

8. The biological sample comprising non-intact seed tissue from the seed of claim 3, wherein the non-intact seed tissue comprises milled seed and wherein the biological sample comprises the DNA molecule of SEQ ID NO: 10.

9. The biological sample of claim 8, wherein the biological sample comprises flour or meal.

* * * * *

SEQUENCE LISTING

```
<160> NUMBER OF SEQ ID NOS: 21

<210> SEQ ID NO 1
<211> LENGTH: 16752
<212> TYPE: DNA
<213> ORGANISM: Artificial
<220> FEATURE:
<223> OTHER INFORMATION: synthetic

<400> SEQUENCE: 1
gagcatatcc agcaccagct ggtaccaagg tcgggtctct gtgctagtgc tattagctag      60
tgtaaggagc gagtaggtca gttaaggctg gtgcgtcgtg agggctgtct tgtgtgtagc     120
tacagcagac ggttcatcag aaggattatt cgtgcagtat atacagtaca actagacaat     180
gatgttgatg attggtctag agctagaggc ctatagccct atactactgt gtattgtccg     240
ccgttttagt tttttggtcc catcccatca atgcaaccgc cttgttttgc tccaattgtc     300
ccgttcctgc gcctcgcttt tgctctgtcg catcgcatac aaaaaaaaaa acgccgcgcc     360
ggctttgaat cgcgccccc aactgctcca accaggcaac ggacacggcc accgtccgtg     420
tcgcgagcaa aaaacaaaa agaggaacgc gtccaggacg aagcagtcca ctgccgctgt     480
ggccggcaaa agatctggtt gagcacatgg agattggaga aggttggttg gttcttctgg     540
aaacgccaat gaatggggc actgacatgt actcttaaca tgtagtgcaa tccagagatc     600
ggatatccag acactggcag cacgatcgcc tcgcgccgta gatcacgcac gcaaattact     660
```

```
gaagaccatt cacaaaaaaa aaaaaacaca caggggctag cgtgccccac accaaaccca    720
agtgctgcgt tgcacgcagg ggagcgaaaa aaaacaataa tgctcactgt cacgtcgcgt    780
atccaacccc gcggacgtct cggctctcag cagcagcaca cggggcacct cacgatgccg    840
ttctcgttgc actccgtgca ccgcggaaac ccgccgccgc attcgtcgcc ctcctcctcc    900
tcctccgcct cgtcttcgtc acccacgtac accttgcagc tgcccgagca gacatcgcag    960
agcacgaacc gcatgtcccc gcaggcctcg cacgcgccgg cgtcgccgcc gtgtgggccg   1020
gccgtcgacg cagcgctctc gcacccggcc agcctcggcg cgagctcccc ggcctcgtgc   1080
agccgcttca gctcctcggc gttgcccacg agctccccgt ccacgaagag ctggggagg    1140
gcggcgggcg tgccgccggc ttggccgagc ccgaggccga aaggccgcg gagctcgtcc    1200
cggaacccgc ggtgcatgga cacgtcgcgc tcgtcgaggc gcacgccgta gcccttgagg   1260
atggcgcgcg ccaggcagca gtcctcgtgc gtggcgcgca cgccgcgcag cgacgtgaag   1320
tagagcaccg ccctccgcgg cggcagcgcc ttcccctccc cgccgctcgt cggggcggcg   1380
tcgggccgag gcatcggcat cggcagcggc gtcaccttgg cggacgccgc gaggtcctgc   1440
gcaggcgccg tggcgaccgg gaacgagaag gagtggcgcc cgaacggcgc gcccagcagc   1500
ggggagcggt cctcgaggcc ggccatgagc gcccacgcgt cgatgtcctc gggctcgttg   1560
ggcggcgtca tggtgggcgt gcgcggcgcc agcctcgtgg gcgcgggctc cggcgcccgc   1620
ggcagggcct tgtccagctc cagggacccg agcgtgacg acgtgagccg caccacgtgg   1680
acgccgacgt cgctggggca ccgagccggg aacgactggc tgcgcggcag cggtgacggg   1740
cagtaccgga ggtcgtgacg ggcctgcctt gaggtggtgc accccatggc accaatgtac   1800
acacacggcc aaagcgccaa gtgggctgca gactgcctgc caatgtgatc aagcagccag   1860
gagcagagac ggatctctgg ggatcggggt ttctggggtt taggatcttt atactactct   1920
gtcattgggg atataaaact aggagtgtgg ttaattagga ctcgatagat aagtttacca   1980
caagcgcgtg aaatggtcta cccgatgatg tgattggcct aaaaagaaca agaagagtat   2040
ttggagctac tgaacattct cttttcctga agataactaa ttttggaac attcagactt    2100
gggagtctgg acttttggag ggaagttcaa attgtggtct gcctctgcca tgtgttgttt   2160
tttagtcgga gagtggccct cattttttt gtcctgttta gctttatagt cgtagcagct    2220
agtagcgaaa tttaaccttg gattatggcc gtgttagtca aacaatcatt gatttatttc   2280
ctcccttcg cgctgctttt cctgtacgca tctccgctgc ccttgattcg aggaccctgt    2340
tcacaacaca gggctctggc tttggagcct tcgtttgta gcacttgcac gtagttaccc    2400
ggaccgaagc ttcaacacag atctgatagt ttaaacgctc ttcaactgga agagcggtta   2460
cccgaccga agcttcggcc ggggcccatc gatatccgcg gcatgcctg cagtgcagcg     2520
tgacccggtc gtgcccctct ctagagataa tgagcattgc atgtctaagt tataaaaaat   2580
taccacatat tttttttgtc acacttgttt gaagtgcagt ttatctatct ttatacatat   2640
atttaaactt tactctacga ataatataat ctatagtact acaataatat cagtgttta    2700
gagaatcata taaatgaaca gttagacatg gtctaaagga caattgagta ttttgacaac   2760
aggactctac agttatct tttagtgtg catgtgttct ccttttttt tgcaaatagc       2820
ttcacctata taatacttca tccatttat tagtacatcc atttagggtt tagggttaat   2880
ggtttttata gactaatttt tttagtacat ctattttat ctattttagc ctctaaatta    2940
agaaaactaa aactctattt tagtttttt attaataat ttagatataa aatagaataa    3000
aataaagtga ctaaaaatta aacaaatacc ctttaagaaa ttaaaaaaac taaggaaaca   3060
```

```
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca ccccctccac accctctttc cccaacctcg    3420
tgttgttcgg agcgcacaca cacacaacca gatctccccc aaatccaccc gtcggcacct    3480
ccgcttcaag gtacgccgct cgtcctcccc ccccccccct ctctaccttc tctagatcgg    3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt ttttgtttc gttgcatagg gtttggtttg    3780
cccttttcct ttatttcaat atatgccgtg cacttgtttg tcgggtcatc ttttcatgct    3840 ttttttgtc ttggttgtga tgatgtggtc tggttgggcg gtcgttctag atcggagtag    3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat ttttttagcc ctgccttcat acgctattta    4440
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740 cttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
```

```
acccccatctc atggacttca tgaactctttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
tacccccaca acaccattg atccagagag aatcactcag attcccttgg tgaaggcaca    5940
cacacttcag tcaggaacta cagttgtaag agggccgggg ttcacgggag agacattct    6000 tcgacgcact agtggaggac cattcgcgta caccattgtc aacatcaatg ggcaacttcc    6060
ccaaaggtat cgtgccagga tacgctatgc ctctactacc aatctaagaa tctacgttac    6120
ggttgcaggt gaacggatct tgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgcccggt tcgttgcga ctaacatgag    6420 ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtatttg taatctcata tagatttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttacataaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatcctat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc tttttagtgt    7440
gcatgtgttc tccttttttt ttgcaaatag cttcacctat ataatacttc atccatttta    7500
ttagtacatc catttagggt ttaggttaa tggttttat agactaattt ttttagtaca    7560 tctatttat tctatttag cctctaaatt aagaaaacta aaactctatt ttagtttttt    7620
tatttaataa tttagatata aaatagaata aaataaagtg actaaaaatt aaacaaatac    7680
cctttaagaa attaaaaaaa ctaaggaaac attttttcttg tttcgagtag ataatgccag    7740
cctgttaaac gccgtcgacg agtctaacgg acaccaacca gcgaaccagc agcgtcgcgt    7800
```

```
cgggccaagc gaagcagacg gcacggcatc tctgtcgctg cctctggacc cctctcgaga   7860
gttccgctcc accgttggac ttgctccgct gtcggcatcc agaaattgcg tggcggagcg   7920
gcagacgtga gccggcacgg caggcggcct cctcctcctc tcacggcacc ggcagctacg   7980
ggggattcct ttcccaccgc tccttcgctt tcccttcctc gcccgccgta ataaatagac   8040
accccctcca caccctcttt ccccaacctc gtgttgttcg gagcgcacac acacacaacc   8100
agatctcccc caaatccacc cgtcggcacc tccgcttcaa ggtacgccgc tcgtcctccc   8160
cccccccccc tctctacctt ctctagatcg gcgttccggt ccatggttag ggcccggtag   8220
ttctacttct gttcatgttt gtgttagatc cgtgtttgtg ttagatccgt gctgctagcg   8280
ttcgtacacg gatgcgacct gtacgtcaga cacgttctga ttgctaactt gccagtgttt   8340
ctctttgggg aatcctggga tggctctagc cgttccgcag acgggatcga tttcatgatt   8400 tttttttgttt cgttgcatag ggtttggttt gccctttttcc tttatttcaa tatatgccgt   8460
gcacttgttt gtcgggtcat cttttcatgc ttttttttgt cttggttgtg atgatgtggt   8520
ctggttgggc ggtcgttcta gatcggagta gaattctgtt tcaaactacc tggtggattt   8580
attaattttg gatctgtatg tgtgtgccat acatattcat agttacgaat tgaagatgat   8640
ggatggaaat atcgatctag gataggtata catgttgatg cgggttttac tgatgcatat   8700
acagagatgc ttttgttcg cttggttgtg atgatgtggt gtggttgggc ggtcgttcat   8760
tcgttctaga tcggagtaga atactgtttc aaactacctg gtgtatttat taattttgga   8820
actgtatgtg tgtgtcatac atcttcatag ttacgagttt aagatggatg gaaatatcga   8880
tctaggatag gtatacatgt tgatgtgggt tttactgatg catatacatg atggcatatg   8940
cagcatctat tcatatgctc taaccttgag tacctatcta ttataataaa caagtatgtt   9000
ttataattat tttgatcttg atatacttgg atgatggcat atgcagcagc tatatgtgga   9060
tttttttagc cctgccttca tacgctattt atttgcttgg tactgtttct tttgtcgatg   9120
ctcaccctgt tgtttggtgt tacttctgca ggtcgactct agaggatcca cacgacacca   9180
tgtccgcccg cgaggtgcac atcgacgtga acaacaagac cggccacacc ctccagctgg   9240
aggacaagac caagctcgac ggcggcaggt ggcgcacctc cccgaccaac gtggccaacg   9300
accagatcaa gaccttcgtg gccgaatcca acggcttcat gaccggcacc gagggcacca   9360
tctactactc aattaatggc gaggccgaga tcagcctcta cttcgacaac ccgttcgccg   9420
gctccaacaa atacgacggc cactccaaca gtcccagta cgagatcatc acccagggcg   9480
gctccggcaa ccagtcccac gtgacctaca ccatccagac cacctcctcc cgctacggcc   9540
acaagtcctg agtcatgagt catgagtcag ttaacctaga cttgtccatc ttctggattg   9600
gccaacttaa ttaatgtatg aaataaaagg atgcacacat agtgacatgc taatcactat   9660
aatgtgggca tcaaagttgt gtgttatgtg taattactag ttatctgaat aaaagagaaa   9720
gagatcatcc atatttctta tcctaaatga atgtcacgtg tctttataat tctttgatga   9780
accagatgca tttcattaac caaatccata tacatataaa tattaatcat atataattaa   9840
tatcaattgg gttagcaaaa caaatctagt ctaggtgtgt tttgcgaatg cggccgcgga   9900
ccgaattggg gatctgcatg aaagaaactg tcgcactgct gaaccgcacc ttgtcacttt   9960
catcgaacac gacctgtgcc caagatgacg gtgctgcggt ctaagtgagg ctgaattgcc  10020
ttggacagaa gcggactccc tacaattagt taggccaaac ggtgcatcca tgtgtagctc  10080
cgggctcggg ctgtatcgcc atctgcaata gcatccatgg agctcgttcc atgtagttgg  10140
```

```
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tcccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actcccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca acccgaccga ccagtccatg aactccatcg gcttcctcac catcacctcc   12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg gccaacttaa ttaatgtatg aaataaaagg atgcacacat agtgacatgc   12480
taatcactat aatgtgggca tcaaagttgt gtgttatgtg taattactag ttatctgaat   12540
```

```
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccggccgaa gctggccgcg gaccgaattc ccatggagtc aaagattcaa    12780
atagaggacc taacagaact cgccgtaaag actggcgaac agttcataca gagtctctta    12840
cgactcaatg acaagaagaa aatcttcgtc aacatggtgg agcacgacac gcttgtctac    12900
tccaaaaata tcaaagatac agtctcagaa gaccaaaggg caattgagac ttttcaacaa    12960
agggtaatat ccgaaaacct cctcggattc cattgcccag ctatctgtca ctttattgtg    13020
aagatagtgg aaaaggaagg tggctcctac aaatgccatc attgcgataa aggaaaggcc    13080
atcgttgaag atgcctctgc cgacagtggt cccaaagatg accccccacc cacgaggagc    13140
atcgtggaaa aagaagacgt tccaaccacg tcttcaaagc aagtggattg atgtgatatc    13200
tccactgacg taagggatga cgcacaatcc cactatcctt cgcaagaccc ttcctctata    13260
taaggaagtt catttcattt ggagaggaca gggtacccgg ggatccacca tgtctccgga    13320
gaggagacca gttgagatta ggccagctac agcagctgat atggccgcgg tttgtgtatat   13380 cgttaaccat tacattgaga cgtctacagt gaactttagg acagagccac aaacaccaca    13440
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaaccaaaat ccagggcgag ctcgaattcg agctcgagcc    14100
cgggtggatc ctctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
ctactagaca attcagtaca ttaaaaacgt ccgcaatgtg ttattaagtt gtctaagcgt    14340
caatttggaa caagtggcta tcgccagata taagaacttc gatccgaaat atcgtttcaa    14400
aactagaaaa cagcgcggct ttggctaagc cgcgcactat ataggatttt gggcacccttt   14460 tgatggaacg tgaaagcgta ctgcgcacta gttatttagg ttgaaccttg gatatacggt    14520
tctcactgcg ccaatgcaag gcttgaaact tggttagtaa tacgtactcc ctccgtttct    14580
ttttatttgt cgctggatag tgcaattttg cactatcgag cgacaaataa aaagaaacgg    14640
agggagtata tgattgtcag atgtagatat gtttatttat atatcacata cagatatata    14700
aaacagatca cttttttcaga tatacagttc caatgtcagc cctgatcacc ctgtcataaa    14760
ttgcacgttt ctaattgatg ttgcttcatg gtcgtcatga gaaccttctg aagaaatcga    14820
tgaaggttgc caacctttca aagtttcaga aaccactttg catgtacact aagggctggt    14880
```

```
ttggcagccc aaaaccagcc agcgttttcc tggtcttttc tcccgggaga agcccatgc    14940 atagattgtc cctggattat ttatctgtgt cctttggcta aaaattcgtc ccaatttcct   15000
gtaggaaact acctcggcct tgggaggcca ggcgattctc caccgcctcg tctcgtccat   15060
ccttcgatgc tcacgcgtgc ctcctcggat gctatcctca ggcgattctc cgtcgtctcg   15120
tctcatccat cctcacgcgc gcctcctccg acgctatccc caggcgattc tccaccgtct   15180
cgtctcatcc atcctcatgt acgcctcgtc cgatgctatc cccagacgat tttccgtcgt   15240
ctcatctcct tcatgctcgc gcgcgcctcc tccgacgcta tccccaggcg attttttctgc  15300 cgtctcgtct ccttcatgcc cgcgcgcgcc tcctccgacg ctatccccag gcgattttcc   15360
gccgtctcgt ctccttcatg cccgcgcgtg cctcctccga cgctattccc acgagcgcct   15420
ccgccgccgc tatccccaga cgattttccg ctgtctcgtc tccttcatgc ccgcgcgccc   15480
ctcctccgac gctatcccca cgagcgcctc cgccgccgct ccaccgtctt cccgccgcc    15540 atcccttaa ttcctataga tctgaccccc gctctacttt cgttggcata cttttgcttg   15600
gtgtgcgcgg gctggagtgg aaggttgcgc attcgatcac gggggagaag tggatcttgg   15660
gtcttggcag gctagggcgg ttgccaggac gccgtggtgt gcattcatgg gtcctataaa   15720
tctttatcat taccgcctta ggagctagtt gtagttcaca catcatatcc ttttctgctc   15780
gacatcgtct ggggatgccc taggtgccct accgacccta cggcattgtc ttgacctcta   15840
ttagactcta tgtcatctag agccttcttg ggtggccttt tgaccccaaa gcgacccctat  15900 gatcttaccc taacgaggtc tcccttggtg gggcaagatc cactttgtcc acttaactga   15960
agatctgatc ctcatcttga aatctttaat cccaaggtga ctctacgtcg tatgtggatg   16020
ctccgggtaa cctgccaacc cggatcaccc taagatctct ttcctaaggg gcgagatcta   16080
ggttcctacg agaaagaaga cgaccctgca ccattgcggt ccgtccggtc cagagtgcga   16140
acgtccggat gcgacacagg gaaggagtcg ctcctgcagc gaggtcgcag actgtccaca   16200
cagcctcaga aggcaccgcc agacaataca tgtaatacccc actctgtaag aaaaacctaa   16260
aaggagaaag tatattcctt tatctatatg tgtgttatat ttctactcac catcacatgt   16320
gaacatctca cttacacaaa taaataatta acaaaagaca ctcaaataaa ttatgcatca   16380
tgctcgacct tattttgtgt gcattctgtt acaatataaa aataatataa aaaacatata   16440
ttaatatcaa aatttggaga tttaacccta atatgcaaat cggagtttag aggaaagaaa   16500
gaaaaatgct atacaaaata aaggaataaa tatataaata aaggtaaaac tattaatact   16560
ggtatattaa tttgaacagt tgacctaatt atgaatatca caactggttt gaattcaaat   16620
atgaaatcca agaatttgga aataggaaaa atggagataa gaataaagga aaagaattct   16680
taactcggat gggcctggga aacgaatttc ggcccacttc ctgtgtcctt agctgtgcgg   16740
ctcagtccag tg                                                      16752
```

<210> SEQ ID NO 2
<211> LENGTH: 16695
<212> TYPE: DNA
<213> ORGANISM: Artificial
<220> FEATURE:
<223> OTHER INFORMATION: synthetic

<400> SEQUENCE: 2

```
gagcatatcc agcaccagct ggtaccaagg tcgggtctct gtgctagtgc tattagctag    60
tgtaaggagc gagtaggtca gttaaggctg gtgcgtcgtg agggctgtct tgtgtgtagc   120
tacagcagac ggttcatcag aaggattatt cgtgcagtat atacagtaca actagacaat   180
```

-continued

```
gatgttgatg attggtctag agctagaggc ctatagccct atactactgt gtattgtccg      240
ccgttttagt ttttggtcc catcccatca atgcaaccgc cttgttttgc tccaattgtc       300
ccgttcctgc gcctcgcttt tgctctgtcg catcgcatac aaaaaaaaaa acgccgcgcc      360
ggctttgaat cgcgcccccc aactgctcca accaggcaac ggacacgcc accgtccgtg       420 tcgcgagcaa aaaacaaaa agaggaacgc gtccaggacg aagcagtcca ctgccgctgt      480
ggccggcaaa agatctggtt gagcacatgg agattggaga aggttggttg gttcttctgg      540
aaacgccaat gaatgggggc actgacatgt actcttaaca tgtagtgcaa tccagagatc    600
ggatatccag acactggcag cacgatcgcc tcgcgccgta gatcacgcac gcaaattact    660
gaagaccatt cacaaaaaaa aaaaacaca caggggctag cgtgccccac accaaaccca     720
agtgctgcgt tgcacgcagg ggagcgaaaa aaaacaataa tgctcactgt cacgtcgcgt   780
atccaacccc gcggacgtct cggctctcag cagcagcaca cggggcacct cacgatgccg   840
ttctcgttgc actccgtgca ccgccggaac ccgccgccgc attcgtcgcc ctcctcctcc    900
tcctccgcct cgtcttcgtc acccacgtac accttgcagc tgcccgagca gacatcgcag   960
agcacgaacc gcatgtcccc gcaggcctcg cacgcgccgg cgtcgccgcc gtgtgggccg   1020
gccgtcgacg cagcgctctc gcacccggcc agcctcggcg cgagctcccc ggcctcgtgc   1080
agccgcttca gctcctcggc gttgcccacg agctccccgt ccacgaagag gctggggagg   1140
gcggcgggcg tgccgccggc ttggccgagc ccgaggccga aaggccgcg gagctcgtcc    1200 cggaacccgc ggtgcatgga cacgtcgcgc tcgtcgaggc gcacgccgta gcccttgagg   1260
atggcgcgcg ccaggcagca gtcctcgtgc gtggcgcgca cgccgcgcag cgacgtgaag   1320
tagagcaccg ccctccgcgg cggcagcgcc ttcccctccc cgccgctcgt cggggcggcg   1380
tcgggccgag gcatcggcat cggcagcggc gtcaccttgg cggacgccgc gaggtcctgc   1440
gcaggcgccg tggcgaccgg gaacgagaag gagtggcgcc cgaacggcgc gcccagcagc   1500
ggggagcggt cctcgaggcc ggccatgagc gcccacgcgt cgatgtcctc gggctcgttg   1560
ggcggcgtca tggtgggcgt gcgcggcgcc agcctcgtgg gcgcgggctc cggcgcccgc   1620
ggcagggcct tgtccagctc cagggacccg agcgtggacg acgtgagccg caccacgtgg   1680
acgccgacgt cgctggggca ccgagccggg aacgactggc tgcgcggcag cggtgacggg   1740
cagtaccgga ggtcgtgacg ggcctgcctt gaggtggtgc accccatggc accaatgtac   1800
acacacggcc aaagcgccaa gtgggctgca gactgcctgc caatgtgatc aagcagccag   1860
gagcagagac ggatctctgg ggatcggggt ttctggggtt taggatcttt atactactct    1920
gtcattgggg atataaaact aggagtgtgg ttaattagga ctcgatagat aagtttacca   1980
caagcgcgtg aaatggtcta cccgatgatg tgattggcct aaaaagaaca agaagagtat  2040
ttggagctac tgaacattct ctttcctga agataactaa tttttggaac attcagactt   2100
gggagtctgg acttttggag ggaagttcaa attgtggtct gcctctgcca tgtgttgttt   2160
tttagtcgga gagtggccct cattttttt gtcctgttta gctttatagt cgtagcagct  2220
agtagcgaaa tttaaccttg gattatggcc gtgttagtca aacaatcatt gatttatttc  2280 ctcccttttcg cgctgctttt cctgtacgca tctccgctgc ccttgattcg aggaccctgt 2340
tcacaacaca gggctctggc tttggagcct ctcgtttgta gcacttgcac gtagttaccc   2400
ggaccgaagc ttcaacacag atctgatagt ttaaacgctc ttcaactgga agagcggtta  2460
cccggaccga agcttcggcc ggggcccatc gatatccgcg gcatgcctg cagtgcagcg   2520
```

```
tgacccggtc gtgcccctct ctagagataa tgagcattgc atgtctaagt tataaaaaat    2580
taccacatat ttttttttgtc acacttgttt gaagtgcagt ttatctatct ttatacatat   2640
atttaaactt tactctacga ataatataat ctatagtact acaataatat cagtgtttta    2700
gagaatcata taaatgaaca gttagacatg gtctaaagga caattgagta ttttgacaac    2760
aggactctac agtttatct ttttagtgtg catgtgttct cctttttttt tgcaaatagc     2820
ttcacctata taatacttca tccatttat tagtacatcc atttagggtt tagggttaat     2880
ggtttttata gactaatttt tttagtacat ctattttatt ctattttagc ctctaaatta    2940
agaaaactaa aactctattt tagtttttt atttaataat ttagatataa aatagaataa     3000
aataaagtga ctaaaaatta aacaaatacc ctttaagaaa ttaaaaaaac taaggaaaca    3060
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca ccccctccac accctctttc cccaacctcg    3420
tgttgttcgg agcgcacaca cacacaacca gatctccccc aaatccaccc gtcggcacct    3480
ccgcttcaag gtacgccgct cgtcctcccc cccccccct ctctaccttc tctagatcgg     3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt ttttgtttc gttgcatagg gtttggtttg     3780 ccctttcct ttatttcaat atatgccgtg cacttgtttg tcgggtcatc ttttcatgct     3840 ttttttgtc ttggttgtga tgatgtggtc tggttgggcg gtcgttctag atcggagtag     3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat tttttagcc ctgccttcat acgctattta    4440
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740
ctttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
```

```
taacacagat gatgctttga tcacagccat caacaacttc acccttacca gcttcgagat   4980
ccctcttctc tcggtctatg ttcaagctgc taacctgcac ttgtcactac tgcgcgacgc   5040
tgtgtcgttt gggcaaggtt ggggactgga catagctact gtcaacaatc actacaacag   5100
actcatcaat ctgattcatc gatacacgaa acattgtttg gatacctaca atcagggatt   5160
ggagaacctg agaggtacta acactcgcca atgggccagg ttcaatcagt tcaggagaga   5220
ccttacactt actgtgttag acatagttgc tctctttccg aactacgatg ttcgtaccta   5280
tccgattcaa acgtcatccc aacttacaag ggagatctac accagttcag tcattgaaga   5340
ctctccagtt tctgcgaaca tacccaatgg tttcaacagg gctgagtttg gagtcagacc   5400
accccatctc atggacttca tgaactcttt gtttgtgact gcagagactg ttagatccca   5460
aactgtgtgg ggaggacact tagttagctc acgcaacacg gctggcaatc gtatcaactt   5520
tcctagttac ggggtcttca atcccggggg cgccatctgg attgcagatg aagatccacg   5580
tcctttctat cggaccttgt cagatcctgt cttcgtccga ggaggctttg gcaatcctca   5640
ctatgtactc ggtcttaggg gagtggcctt tcaacaaact ggtacgaatc acacccgcac   5700
attcaggaac tccgggacca ttgactctct agatgagata ccacctcaag acaacagcgg   5760
cgcaccttgg aatgactact cccatgtgct gaatcatgtt acctttgtgc gctggccagg   5820
tgagatctca ggttccgact catggagagc accaatgttc tcttggacgc atcgtagcgc   5880
taccccacac aacaccattg atccagagag aatcactcag attcccttgg tgaaggcaca   5940
cacacttcag tcaggaacta cagttgtaag agggccgggg ttcacgggag agacattct    6000
tcgacgcact agtggaggac cattcgcgta caccattgtc aacatcaatg gcaacttcc    6060
ccaaaggtat cgtgccagga tacgctatgc ctctactacc aatctaagaa tctacgttac   6120
ggttgcaggt gaacggatct ttgctggtca gttcaacaag acaatggata ccggtgatcc   6180
acttacattc caatctttct cctacgccac tatcaacacc gcgttcacct ttccaatgag   6240
ccagagcagt ttcacagtag gtgctgatac cttcagttca ggcaacgaag tgtacattga   6300
caggtttgag ttgattccag ttactgccac actcgagtaa ggatccgtcg acctgcagcc   6360
aagctttcgc gagctcgaga tccccgacat atgccccggt ttcgttgcga ctaacatgag   6420
ttcttggaca aatttgattg gacctgatga gatgatccaa cccgaggata tagcaaagct   6480
cgttcgtgca gcaatggaac ggccaaaccg tgcttttgtc cccaagaatg aggtgctatg   6540
catgaaggaa tctacccgtt gatgtccaac agtctcaggg ttaatgtcta tgtatcttaa   6600
ataatgttgt cggtattttg taatctcata tagattttca ctgtgcgacg caaaaatatt   6660
aaataaatat tattattatc tacgttttga ttgagatatc atcaatatta taataaaaat   6720
atccattaaa cacgatttga tacaaatgac agtcaataat ctgatttgaa tatttattaa   6780
ttgtaacgaa ttacataaag atcgaataga aaatactgca ctgcaaatga aaattaacac   6840
atactaataa atgcgtcaaa tatctttgcc aagatcaagc ggagtgaggg cctcatatcc   6900
ggtctcagtt acaagcacgg tatccccgaa gcgcgctcca ccaatgccct cgacatagat   6960
gccgggctcg acgctgagga cattgcctac cttgagcatg gtctcagcgc cggctttaag   7020
ctcaatccca tcccaatctg aatatccatc ccgcgcccca gtccggtgta agaacgggtc   7080
tgtccatcca cctctgttgg gaattccggt ccgggtcacc tttgtccacc aagatggaac   7140
tgcggccagc ttgcatgcct gcagtgcagc gtgacccgt cgtgccctc tctagagata   7200
atgagcattg catgtctaag ttataaaaaa ttaccacata ttttttttgt cacacttgtt   7260
```

-continued

```
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttagtgt    7440
gcatgtgttc tccttttttt ttgcaaatag cttcacctat ataatacttc atccatttta    7500
ttagtacatc catttagggt ttagggttaa tggttttat agactaattt ttttagtaca     7560
tctatttttat tctatttag cctctaaatt aagaaaacta aaactctatt ttagttttt     7620
tatttaataa tttagatata aaatagaata aaataaagtg actaaaaatt aaacaaatac    7680
cctttaagaa attaaaaaaa ctaaggaaac attttcttg tttcgagtag ataatgccag     7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tcccttcctc gcccgccgta ataaatagac    8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160
ccccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400
ttttttgttt cgttgcatag ggtttggttt gcccttttcc tttatttcaa tatatgccgt    8460
gcacttgttt gtcgggtcat cttttcatgc ttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag gataggtata catgttgatg cgggttttac tgatgcatat    8700
acagagatgc ttttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060
tttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcaccctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca gtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
```

```
aatgtgggca tcaaagttgt gtgttatgtg taattactag ttatctgaat aaaagagaaa   9720
gagatcatcc atatttctta tcctaaatga atgtcacgtg tctttataat tctttgatga   9780
accagatgca tttcattaac caaatccata tacatataaa tattaatcat atataattaa   9840
tatcaattgg gttagcaaaa caaatctagt ctaggtgtgt tttgcgaatg cggccgcgga   9900
ccgaattggg gatctgcatg aaagaaactg tcgcactgct gaaccgcacc ttgtcacttt   9960
catcgaacac gacctgtgcc caagatgacg gtgctgcggt ctaagtgagg ctgaattgcc  10020
ttggacagaa gcggactccc tacaattagt taggccaaac ggtgcatcca tgtgtagctc  10080
cgggctcggc ctgtatcgcc atctgcaata gcatccatgg agctcgttcc atgtagttgg  10140
agatgaacca atgatcgggc gtgtggacgt atgttcctgt gtactccgat agtagagtac  10200
gtgttagctc tttcatggtg caagtgaaat ttgtgttggt ttaattaccc ctacgttagt  10260
tgcgggacag gagacacatc atgaatttaa aggcgatgat gtcctctcct gtaatgttat  10320
tcttttgatg tgatgaatca aaatgtcata taaaacattt gttgctcttt agttaggcct  10380
gatcgtagaa cgaaatgctc gtgtagcggg gctacgagcc tatgacgcaa taacactggt  10440
ttgccggccc ggagtcgctt gacaaaaaaa agcatgttaa gtttatttac aattcaaaac  10500
ctaacatatt atattccctc aaagcaggtt cacgatcaca cctgtaccta aaaaaaacat  10560
gaagaatata ttactccatt attatgagat gaaccacttg gcaagagtgg taagctatat  10620
aaaaaaatga acattattac gagatgttat atgccattat attgattcga agatatatgt  10680
ttctttctcc cacgggcacc taacggatac atgataaggc caaggcagat tacgggaaat  10740
tattcgaata catgttacgc cctattgccg gaaaaaaaat gcagggcagg tgttggccgt  10800
agcgatttaa gcacttaagc tggaggttgc cacacttgga tgcaagcgtc tgacccttct  10860
aaaaaatcgg cggctttgtc cgtatccgta tcccctatcc aacatctagc tggccacacg  10920
acggggctgg gcagatcgtg gatgccgggt cgacgtcgat cgtcagccat catagaccaa  10980
tcgaccatct gttatggatg cttgctagct agactagtca gacataaaat ttggatactt  11040
tctcccaact gggagacggg gactgatgtg cagctgcacg tgagctaaat ttttccctat  11100
aaatatgcat gaaatactgc attatcttgc cacagccact gccacagcca gataacaagt  11160
gcagctggta gcacgcaacg catagctctg gacttgtagc taggtagcca accggatcca  11220
cacgacacca tgctcgacac caacaaggtg tacgagatca gcaaccacgc caacggcctc  11280
tacgccgcca cctacctctc cctcgacgac tccggcgtgt ccctcatgaa caagaacgac  11340
gacgacatcg acgactacaa cctcaagtgg ttcctcttcc cgatcgacga cgaccagtac  11400
atcatcacct cctacgccgc caacaactgc aaggtgtgga acgtgaacaa cgacaagatt  11460
aatgtgtcaa cctactcctc caccaactcc atccagaagt ggcagatcaa ggccaacggc  11520
tcctcctacg tgatccagtc cgacaacggc aaggtgctca ccgccggcac cggccaggcc  11580
ctcggcctca tccgcctcac cgacgagtcc tccaacaacc cgaaccagca atggaacctg  11640
acgtccgtgc agaccatcca gctcccgcag aagccgatca tcgacaccaa gctcaaggac  11700
tacccgaagt actccccgac cggcaacatc gacaacggca cctccccgca gctcatgggc  11760
tggaccctcg tgccgtgcat catggtgaac gacccgaaca tcgacaagaa cacccagatc  11820
aagaccaccc cgtactacat cctcaagaag taccagtact ggcagagggc cgtgggctcc  11880
aacgtcgcgc tccgcccgca cgagaagaag tcctacacct acgagtgggg caccgagatc  11940
gaccagaaga ccaccatcat caacaccctc ggcttccaga tcaacatcga cagcggcatg  12000
```

-continued

```
aagttcgaca tcccggaggt gggcggcggt accgacgaga tcaagaccca gctcaacgag    12060
gagctcaaga tcgagtattc acatgagacg aagatcatgg agaagtacca ggagcagtcc    12120
gagatcgaca acccgaccga ccagtccatg aactccatcg gcttcctcac catcacctcc    12180
ctggagctct accgctacaa cggctccgag atccgcatca tgcagatcca gacctccgac    12240
aacgacacct acaacgtgac ctcctacccg aaccaccagc aggccctgct gctgctgacc    12300
aaccactcct acgaggaggt ggaggagatc accaacatcc cgaagtccac cctcaagaag    12360
ctcaagaagt actacttctg agtcatgagt catgagtcag ttaacctaga cttgtccatc    12420
ttctggattg gccaacttaa ttaatgtatg aaataaaagg atgcacacat agtgacatgc    12480
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccggccgaa gctggccgcg gaccgaattc ccatggagtc aaagattcaa    12780
atagaggacc taacagaact cgccgtaaag actggcgaac agttcataca gagtctctta    12840
cgactcaatg acaagaagaa aatcttcgtc aacatggtgg agcacgacac gcttgtctac    12900
tccaaaaata tcaagataca gtctcagaa gaccaagggg caattgagac ttttcaacaa    12960
agggtaatat ccggaaacct cctcggattc cattgcccag ctatctgtca ctttattgtg    13020
aagatagtgg aaaggaagg tggctcctac aaatgccatc attgcgataa aggaaaggcc    13080
atcgttgaag atgcctctgc cgacagtggt cccaaagatg accccaccc acgaggagc    13140 atcgtggaaa aagaagacgt tccaaccacg tcttcaaagc aagtggattg atgtgatatc    13200
tccactgacg taagggatga cgcacaatcc cactatcctt cgcaagaccc ttcctctata    13260
taaggaagtt catttcattt ggagaggaca gggtacccgg ggatccacca tgtctccgga    13320
gaggagacca gttgagatta ggccagctac agcagctgat atggccgcgg tttgtgatat    13380
cgttaaccat tacattgaga cgtctacagt gaactttagg acagagccac aaacaccaca    13440
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaaccaaaat ccagggcgag ctcgaattcg agctcgagcc    14100
cgggtggatc tctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
cttttgtagc acttgcacgt agttaccggg atataagaac ttcgatccga aatatcgttt    14340
caaaactaga aaacagcgcg gctttggcta agccgcgcac tatataggat tttgggcacc    14400
```

```
ttttgatgga acgtgaaagc gtactgcgca ctagttattt aggttgaacc ttggatatac   14460
ggttctcact gcgccaatgc aaggcttgaa acttggttag taatacgtac tccctccgtt   14520 tcttttatt tgtcgctgga tagtgcaatt ttgcactatc gagcgacaaa taaaagaaa     14580 cggagggagt atatgattgt cagatgtaga tatgtttatt tatatatcac atacagatat   14640
ataaaacaga tcactttttc agatatacag ttccaatgtc agccctgatc accctgtcat   14700
aaattgcacg tttctaattg atgttgcttc atggtcgtca tgagaaccct ctgaagaaat   14760
cgatgaaggt tgccaacctt tcaaagtttc agaaaccact ttgcatgtac actaagggct   14820
ggtttggcag cccaaaacca gccagcgttt tcctggtctt ttctcccggg agaaagccca   14880
tgcatagatt gtccctggat tatttatctg tgtcctttgg ctaaaaattc gtcccaattt   14940
cctgtaggaa actacctcgg ccttgggagg ccaggcgatt ctccaccgcc tcgtctcgtc   15000
catccttcga tgctcacgcg tgcctcctcg gatgctatcc tcaggcgatt ctccgtcgtc   15060
tcgtctcatc catcctcacg cgcgcctcct ccgacgctat ccccaggcga ttctccaccg   15120
tctcgtctca tccatcctca tgtacgcctc gtccgatgct atccccagac gattttccgt   15180
cgtctcatct ccttcatgct cgcgcgcgcc tcctccgacg ctatccccag gcgattttc    15240 tgccgtctcg tctccttcat gcccgcgcgc gcctcctccg acgctatccc caggcgattt   15300
tccgccgtct cgtctccttc atgcccgcgc gtgcctcctc cgacgctatt ccacgagcg    15360 cctccgccgc cgctatcccc agacgatttt ccgctgtctc gtctccttca tgcccgcgcg   15420 ccctcctcc gacgctatcc ccacgagcgc ctccgccgcc gctccaccgt cttcccgcc     15480 gccatcccct taattcctat agatctggac cccgctctac tttcgttggc atacttttgc   15540
ttggtgtgcg cgggctggag tggaaggttg cgcattcgat cacggggag aagtggatct    15600 tgggtcttgg caggctaggg cggttgccag gacgccgtgg tgtgcattca tgggtcctat   15660
aaatctttat cattaccgcc ttaggagcta gttgtagttc acacatcata tccttttctg   15720
ctcgacatcg tctggggatg ccctaggtgc cctaccgacc ctacggcatt gtcttgacct   15780
ctattagact ctatgtcatc tagagccttc ttgggtggcc ttttgaccccc aaagcgaccc   15840 tatgatctta ccctaacgag gtctcccttg gtggggcaag atccactttg tccacttaac   15900
tgaagatctg atcctcatct tgaaatcttt aatcccaagg tgactctacg tcgtatgtgg   15960
atgctccggg taacctgcca acccggatca ccctaagatc tctttcctaa ggggcgagat   16020
ctaggttcct acgagaaaga agacgaccct gcaccattgc ggtccgtccg gtccagagtg   16080
cgaacgtccg gatgcgacac agggaaggag tcgtcctgc agcgaggtcg cagactgtcc    16140
acacagcctc agaaggcacc gccagacaat acatgtaata cccactctgt aagaaaaacc   16200
taaaaggaga aagtatattc ctttatctat atgtgtgtta tatttctact caccatcaca   16260
tgtgaacatc tcacttacac aaataaataa ttaacaaaag cactcaaat aaattatgca    16320 tcatgctcga ccttattttg tgtgcattct gttacaatat aaaaataata taaaaacat    16380 atattaatat caaaatttgg agatttaacc ctaatatgca aatcggagtt tagaggaaag   16440
aaagaaaaat gctatacaaa ataaaggaat aaatatataa ataaaggtaa aactattaat   16500
actggtatat taatttgaac agttgaccta attatgaata tcacaactgg tttgaattca   16560
aatatgaaat ccaagaattt ggaaatagga aaatggaga taagaataaa ggaaaagaat    16620
tcttaactcg gatgggcctg ggaaacgaat ttcggcccac ttcctgtgtc cttagctgtg   16680
cggctcagtc cagtg                                                   16695
```

<210> SEQ ID NO 3
<211> LENGTH: 16699
<212> TYPE: DNA
<213> ORGANISM: Artificial
<220> FEATURE:
<223> OTHER INFORMATION: synthetic

<400> SEQUENCE: 3

| | | | | | |
|---|---|---|---|---|---|
| gagcatatcc | agcaccagct | ggtaccaagg | tcgggtctct | gtgctagtgc | tattagctag | 60 |
| tgtaaggagc | gagtaggtca | gttaaggctg | gtgcgtcgtg | agggctgtct | tgtgtgtagc | 120 |
| tacagcagac | ggttcatcag | aaggattatt | cgtgcagtat | atacagtaca | actagacaat | 180 |
| gatgttgatg | attggtctag | agctagaggc | ctatagccct | atactactgt | gtattgtccg | 240 |
| ccgtttagt | ttttggtcc | catcccatca | atgcaaccgc | cttgttttgc | tccaattgtc | 300 |
| ccgttcctgc | gcctcgcttt | tgctctgtcg | catcgcatac | aaaaaaaaaa | acgccgcgcc | 360 |
| ggctttgaat | cgcgcccccc | aactgctcca | accaggcaac | ggacacggcc | accgtccgtg | 420 |
| tcgcgagcaa | aaaacaaaa | agaggaacgc | gtccaggacg | aagcagtcca | ctgccgctgt | 480 |
| ggccggcaaa | agatctggtt | gagcacatgg | agattggaga | aggttggttg | gttcttctgg | 540 |
| aaacgccaat | gaatggggc | actgacatgt | actcttaaca | tgtagtgcaa | tccagagatc | 600 |
| ggatatccag | acactggcag | cacgatcgcc | tcgcgccgta | gatcacgcac | gcaaattact | 660 |
| gaagaccatt | cacaaaaaaa | aaaaacaca | caggggctag | cgtgccccac | accaaaccca | 720 |
| agtgctgcgt | tgcacgcagg | ggagcgaaaa | aaaacaataa | tgctcactgt | cacgtcgcgt | 780 |
| atccaacccc | gcggacgtct | cggctctcag | cagcagcaca | cggggcacct | cacgatgccg | 840 |
| ttctcgttgc | actccgtgca | ccgccggaac | ccgccgccgc | attcgtcgcc | ctcctcctcc | 900 |
| tcctccgcct | cgtcttcgtc | acccacgtac | accttgcagc | tgcccgagca | gacatcgcag | 960 |
| agcacgaacc | gcatgtcccc | gcaggcctcg | cacgcgccgg | cgtcgccgcc | gtgtgggccg | 1020 |
| gccgtcgacg | cagcgctctc | gcacccggcc | agcctcggcg | cgagctcccc | ggcctcgtgc | 1080 |
| agccgcttca | gctcctcggc | gttgcccacg | agctccccgt | ccacgaagag | gctggggagg | 1140 |
| gcggcgggcg | tgccgccggc | ttggccgagc | ccgaggccga | aaggccgcg | gagctcgtcc | 1200 |
| cggaacccgc | ggtgcatgga | cacgtcgcgc | tcgtcgaggc | gcacgccgta | gcccttgagg | 1260 |
| atggcgcgcg | ccaggcagca | gtcctcgtgc | gtggcgcgca | cgccgcgcag | cgacgtgaag | 1320 |
| tagagcaccg | ccctccgcgg | cggcagcgcc | ttccctcc | cgccgctcgt | cggggcggcg | 1380 |
| tcgggccgag | gcatcggcat | cggcagcggc | gtcaccttgg | cggacgccgc | gaggtcctgc | 1440 |
| gcaggcgccg | tggcgaccgg | gaacgagaag | gagtggcgcc | cgaacggcgc | gcccagcagc | 1500 |
| ggggagcggt | cctcgaggcc | ggccatgagc | gcccacgcgt | cgatgtcctc | gggctcgttg | 1560 |
| ggcggcgtca | tggtgggcgt | gcgcggcgcc | agcctcgtgg | gcgcgggctc | cggcgcccgc | 1620 |
| ggcagggcct | tgtccagctc | cagggacccg | agcgtggacg | acgtgagccg | caccacgtgg | 1680 |
| acgccgacgt | cgctggggca | ccgagccggg | aacgactggc | tgcgcggcag | cggtgacggg | 1740 |
| cagtaccgga | ggtcgtgacg | ggcctgcctt | gaggtggtgc | accccatggc | accaatgtac | 1800 |
| acacacggcc | aaagcgccaa | gtgggctgca | gactgcctgc | caatgtgatc | aagcagccag | 1860 |
| gagcagagac | ggatctctgg | ggatcgggt | ttctggggtt | taggatcttt | atactactct | 1920 |
| gtcattgggg | atataaaact | aggagtgtgg | ttaattagga | ctcgatagat | aagtttacca | 1980 |
| caagcgcgtg | aaatggtcta | cccgatgatg | tgattggcct | aaaaagaaca | agaagagtat | 2040 |
| ttggagctac | tgaacattct | cttttcctga | agataactaa | ttttggaac | attcagactt | 2100 |

```
gggagtctgg acttttggag ggaagttcaa attgtggtct gcctctgcca tgtgttgttt    2160
tttagtcgga gagtggccct catttttttt gtcctgttta gctttatagt cgtagcagct    2220
agtagcgaaa tttaaccttg gattatggcc gtgttagtca aacaatcatt gatttatttc    2280 ctcccttcg cgctgctttt cctgtacgca tctccgctgc ccttgattcg aggaccctgt    2340
tcacaacaca gggctctggc tttggagcct ctcgtttgta gcacttgcac gtagttaccc    2400
ggaccgaagc ttcaacacag atctgatagt ttaaacgctc ttcaactgga agagcggtta    2460
cccggaccga agcttcggcc ggggcccatc gatatccgcg gcatgcctg cagtgcagcg    2520 tgacccggtc gtgcccctct ctagagataa tgagcattgc atgtctaagt tataaaaaat    2580
taccacatat ttttttttgtc acacttgttt gaagtgcagt ttatctatct ttatacatat    2640
atttaaactt tactctacga ataatataat ctatagtact acaataatat cagtgtttta    2700
gagaatcata taaatgaaca gttagacatg gtctaaagga caattgagta ttttgacaac    2760
aggactctac agttttatct ttttagtgtg catgtgttct cctttttttt tgcaaatagc    2820
ttcacctata taatacttca tccatttat tagtacatcc atttagggtt tagggttaat    2880 ggttttata gactaatttt tttagtacat ctattttatt ctattttagc ctctaaatta    2940
agaaaactaa aactctattt tagttttttt atttaataat ttagatataa aatagaataa    3000 aataagtga ctaaaaatta aacaaatacc ctttaagaaa ttaaaaaaac taaggaaaca    3060
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca cccctccac accctctttc cccaacctcg    3420
tgttgttcgg agcgcacaca cacacaacca gatctccccc aaatccaccc gtcggcacct    3480
ccgcttcaag gtacgccgct cgtcctcccc ccccccccct ctctaccttc tctagatcgg    3540
cgttccggtc catggttagg gcccggtagt tctacttctg ttcatgttg tgttagatcc    3600 gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt ttttgtttc gttgcatagg gtttggtttg    3780 ccccttttcct ttatttcaat atatgccgtg cacttgtttg tcgggtcatc ttttcatgct    3840 ttttttgtc ttggttgtga tgatgtggtc tggttgggcg gtcgttctag atcggagtag    3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat tttttagcc ctgccttcat acgctattta    4440
```

```
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740
ctttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta caatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
tacccccaca aacaccattg atccagagag aatcactcag attcccttgg tgaaggcaca    5940
cacacttcag tcaggaacta cagttgtaag agggccgggg ttcacgggag agacattct    6000 tcgacgcact agtggaggac cattcgcgta caccattgtc aacatcaatg gcaacttcc    6060 ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt ttcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttacataaag atcgaataga aaatactgca ctgcaaatga aaattaacac    6840
```

```
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatccatc ccgcgcccaa gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc tttttagtgt    7440
gcatgtgttc tcctttttt ttgcaaatag cttcacctat ataatacttc atccatttta    7500
ttagtacatc catttagggt ttaggggttaa tggttttat agactaattt ttttagtaca    7560
tctattttat tctatttag cctctaaatt aagaaaacta aaactctatt ttagttttt     7620 tatttaataa tttagatata aaatagaata aaataaagtg actaaaaatt aaacaaatac    7680
cctttaagaa attaaaaaaa ctaaggaaac attttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tccttcctc gcccgccgta ataaatagac     8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160 ccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400 tttttgttt cgttgcatag ggtttggttt gccctttcc tttatttcaa tatatgccgt     8460
gcacttgttt gtcgggtcat cttttcatgc tttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag gataggtata catgttgatc gggtttttac tgatgcatat    8700
acagagatgc tttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060 ttttttagc cctgccttca tacgctattt atttgcttgg tactgtttct tttgtcgatg    9120
ctcaccctgt tgtttggtgt tacttctgca ggtcgactct agaggatcca cacgacacca    9180
```

```
tgtccgcccg cgaggtgcac atcgacgtga acaacaagac cggccacacc ctccagctgg   9240
aggacaagac caagctcgac ggcggcaggt ggcgcacctc cccgaccaac gtggccaacg   9300
accagatcaa gaccttcgtg gccgaatcca acggcttcat gaccggcacc gagggcacca   9360
tctactactc aattaatggc gaggccgaga tcagcctcta cttcgacaac ccgttcgccg   9420
gctccaacaa atacgacggc cactccaaca agtcccagta cgagatcatc acccagggcg   9480
gctccggcaa ccagtcccac gtgacctaca ccatccagac cacctcctcc cgctacggcc   9540
acaagtcctg agtcatgagt catgagtcag ttaacctaga cttgtccatc ttctggattg   9600
gccaacttaa ttaatgtatg aaataaaagg atgcacacat agtgacatgc taatcactat   9660
aatgtgggca tcaaagttgt gtgttatgtg taattactag ttatctgaat aaaagagaaa   9720
gagatcatcc atatttctta tcctaaatga atgtcacgtg tctttataat tctttgatga   9780
accagatgca tttcattaac caaatccata tacatataaa tattaatcat ataattaa    9840 tatcaattgg gttagcaaaa caaatctagt ctaggtgtgt tttgcgaatg cggccgcgga   9900
ccgaattggg gatctgcatg aaagaaactg tcgcactgct gaaccgcacc ttgtcacttt   9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tcccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
```

```
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg cacccgagatc  11940 gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca acccgaccga ccagtccatg aactccatcg gcttcctcac catcacctcc   12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg ccaacttaa ttaatgtatg aaataaaagg atgcacacat agtgacatgc    12480
taatcactat aatgtgggca tcaaagttgt gtgttatgtg taattactag ttatctgaat   12540
aaaagagaaa gagatcatcc atatttctta tcctaaatga atgtcacgtg tctttataat   12600
tctttgatga accagatgca tttcattaac caaatccata tacatataaa tattaatcat   12660
atataattaa tatcaattgg gttagcaaaa caaatctagt ctaggtgtgt tttgcgaatt   12720
atcgatgggc cccggccgaa gctggccgcg gaccgaattc ccatggagtc aaagattcaa   12780
atagaggacc taacagaact cgccgtaaag actggcgaac agttcataca gagtctctta   12840
cgactcaatg acaagaagaa aatcttcgtc aacatggtgg agcacgacac gcttgtctac   12900
tccaaaaata tcaaagatac agtctcagaa gaccaaaggg caattgagac ttttcaacaa   12960
agggtaatat ccggaaacct cctcggattc cattgcccag ctatctgtca ctttattgtg   13020
aagatagtgg aaaaggaagg tggctcctac aaatgccatc attgcgataa aggaaaggcc   13080
atcgttgaag atgcctctgc cgacagtggt cccaaagatg acccccacc cacgaggagc    13140 atcgtggaaa agaagacgt tccaaccacg tcttcaaagc aagtggattg atgtgatatc    13200
tccactgacg taagggatga cgcacaatcc cactatcctt cgcaagaccc ttcctctata   13260
taaggaagtt catttcattt ggagaggaca gggtacccgg ggatccacca tgtctccgga   13320
gaggagacca gttgagatta ggccagctac agcagctgat atggccgcgg tttgtgatat   13380
cgttaaccat tacattgaga cgtctacagt gaactttagg acagagccac aaacaccaca   13440
agagtggatt gatgatctag agaggttgca agatagatac ccttggttgg ttgctgaggt   13500
tgagggtgtt gtgctggta ttgcttacgc tgggccctgg aaggctagga acgcttacga    13560
ttggacagtt gagagtactg tttacgtgtc acataggcat caaaggttgg gcctaggatc   13620
cacattgtac acacatttgc ttaagtctat ggaggcgcaa ggttttaagt ctgtggttgc   13680
tgttataggc cttccaaacg atccatctgt taggttgcat gaggctttgg gatacacagc   13740
ccggggtaca ttgcgcgcag ctggatacaa gcatggtgga tggcatgatg ttggttttg    13800 gcaaagggat tttgagttgc cagctcctcc aaggccagtt aggccagtta cccagatctg   13860
agtcgacctg caggcatgcc cgctgaaatc accagtctct ctctacaaat ctatctctct   13920
```

```
ctataataat gtgtgagtag ttcccagata agggaattag ggttcttata gggtttcgct    13980
catgtgttga gcatataaga aacccttagt atgtatttgt atttgtaaaa tacttctatc    14040
aataaatttt ctaattccta aaaccaaaat ccagggcgag ctcgaattcg agctcgagcc    14100
cgggtggatc tctagagtcg acctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
cttttgtagc acttgcacgt agttacccgg ccagatataa gaacttcgat ccgaaatatc    14340
gtttcaaaac tagaaaacag cgcggctttg gctaagccgc gcactatata ggattttggg    14400
ccccttttga tggaacgtga aagcgtactg cgcactagtt atttaggttg aaccttggat    14460
atacggttct cactgcgcca atgcaaggct tgaaacttgg ttagtaatac gtactccctc    14520
cgtttctttt tatttgtcgc tggatagtgc aattttgcac tatcgagcga caaataaaaa    14580
gaaacggagg gagtatatga ttgtcagatg tagatatgtt tatttatata tcacatacag    14640
atatataaaa cagatcactt tttcagatat acagttccaa tgtcagccct gatcaccctg    14700
tcataaattg cacgttttcta attgatgttg cttcatggtc gtcatgagaa ccttctgaag    14760
aaatcgatga aggttgccaa cctttcaaag tttcagaaac cactttgcat gtacactaag    14820
ggctggtttg gcagcccaaa accagccagc gttttcctgg tcttttctcc cgggagaaag    14880
cccatgcata gattgtccct ggattatta tctgtgtcct ttggctaaaa attcgtccca    14940
atttcctgta ggaaactacc tcggccttgg gaggccaggc gattctccac cgcctcgtct    15000
cgtccatcct tcgatgctca cgcgtgcctc ctcggatgct atcctcaggc gattctccgt    15060
cgtctcgtct catccatcct cacgcgcgcc tcctccgacg ctatcccag gcgattctcc    15120 accgtctcgt ctcatccatc ctcatgtacg cctcgtccga tgctatcccc agacgatttt    15180
ccgtcgtctc atctccttca tgctcgcgcg cgcctcctcc gacgctatcc ccaggcgatt    15240
tttctgccgt ctcgtctcct tcatgcccgc gcgcgcctcc tccgacgcta tccccaggcg    15300
attttccgcc gtctcgtctc cttcatgccc gcgcgtgcct cctccgacgc tattcccacg    15360
agcgcctccg ccgccgctat ccccagacga ttttccgctg tctcgtctcc ttcatgcccg    15420
cgcgcccctc ctccgacgct atcccacga gcgcctccgc cgccgctcca ccgtcttccc    15480
cgccgccatc cccttaattc ctatagatct ggaccccgct ctactttcgt tggcatactt    15540
ttgcttggtg tgcgcgggct ggagtggaag gttgcgcatt cgatcacggg ggagaagtgg    15600
atcttgggtc ttggcaggct agggcggttg ccaggacgcc gtggtgtgca ttcatgggtc    15660
ctataaatct ttatcattac cgccttagga gctagttgta gttcacacat catatccttt    15720
tctgctcgac atcgtctggg gatgccctag gtgccctacc gacccctacgg cattgtcttg    15780 acctctatta gactctatgt catctagagc cttcttgggt ggcttttga ccccaaagcg    15840 accctatgat cttacccta cgaggtctcc cttggtgggg caagatccac tttgtccact    15900
taactgaaga tctgatcctc atcttgaaat ctttaatccc aaggtgactc tacgtcgtat    15960
gtggatgctc cgggtaacct gccaacccgg atcacctaa gatctctttc ctaaggggcg    16020
agatctaggt tcctacgaga aagaagacga ccctgcacca ttgcggtccg tccggtccag    16080
agtgcgaacg tccggatgcg acacagggaa ggagtcgctc ctgcagcgag gtcgcagact    16140
gtccacacag cctcagaagg caccgccaga caatacatgt aatacccact ctgtaagaaa    16200
aacctaaaag gagaaagtat attccttat ctatatgtgt gttatatttc tactcaccat    16260
cacatgtgaa catctcactt acacaaataa ataattaaca aaagacactc aaataaatta    16320
```

```
tgcatcatgc tcgaccttat tttgtgtgca ttctgttaca atataaaaat aatataaaaa    16380
acatatatta atatcaaaat ttggagattt aaccctaata tgcaaatcgg agtttagagg    16440
aaagaaagaa aaatgctata caaaataaag gaataaatat ataaataaag gtaaaactat    16500
taatactggt atattaattt gaacagttga cctaattatg aatatcacaa ctggtttgaa    16560
ttcaaatatg aaatccaaga atttggaaat aggaaaaatg gagataagaa taaaggaaaa    16620
gaattcttaa ctcggatggg cctgggaaac gaatttcggc ccacttcctg tgtccttagc    16680
tgtgcggctc agtccagtg                                                 16699
```

<210> SEQ ID NO 4
<211> LENGTH: 23
<212> TYPE: DNA
<213> ORGANISM: Artificial
<220> FEATURE:
<223> OTHER INFORMATION: synthetic

<400> SEQUENCE: 4
gaacaagtgg ctatcgccag ata                                            23

<210> SEQ ID NO 5
<211> LENGTH: 23
<212> TYPE: DNA
<213> ORGANISM: Artificial
<220> FEATURE:
<223> OTHER INFORMATION: synthetic

<400> SEQUENCE: 5
atgtactgaa ttgtctagta gcg                                            23

<210> SEQ ID NO 6
<211> LENGTH: 23
<212> TYPE: DNA
<213> ORGANISM: Artificial
<220> FEATURE:
<223> OTHER INFORMATION: synthetic

<400> SEQUENCE: 6
ggatcgaagt tcttatatct ggc                                            23

<210> SEQ ID NO 7
<211> LENGTH: 27
<212> TYPE: DNA
<213> ORGANISM: Artificial
<220> FEATURE:
<223> OTHER INFORMATION: synthetic

<400> SEQUENCE: 7
tttgtagcac ttgcacgtag ttacccg                                        27

<210> SEQ ID NO 8
<211> LENGTH: 35
<212> TYPE: DNA
<213> ORGANISM: Artificial
<220> FEATURE:
<223> OTHER INFORMATION: synthetic

<400> SEQUENCE: 8
cgcttttgta gcacttgcac gtagttaccc ggata                               35

<210> SEQ ID NO 9
<211> LENGTH: 64
<212> TYPE: DNA

```
<213> ORGANISM: Artificial
<220> FEATURE:
<223> OTHER INFORMATION: synthetic

<400> SEQUENCE: 9
aacgtgcaag cgcttttgta gcacttgcac gtagttaccc ggatataaga acttcgatcc    60
gaaa                                                                 64

<210> SEQ ID NO 10
<211> LENGTH: 68
<212> TYPE: DNA
<213> ORGANISM: Artificial
<220> FEATURE:
<223> OTHER INFORMATION: synthetic

<400> SEQUENCE: 10
aacgtgcaag cgcttttgta gcacttgcac gtagttaccc ggccagatat aagaacttcg    60
atccgaaa                                                             68

<210> SEQ ID NO 11
<211> LENGTH: 31
<212> TYPE: DNA
<213> ORGANISM: Artificial
<220> FEATURE:
<223> OTHER INFORMATION: synthetic

<400> SEQUENCE: 11
cgcttttgta gcacttgcac gtagttaccc g                                   31

<210> SEQ ID NO 12
<211> LENGTH: 31
<212> TYPE: DNA
<213> ORGANISM: Artificial
<220> FEATURE:
<223> OTHER INFORMATION: synthetic

<400> SEQUENCE: 12
tatccgggta actacgtgca agtgctacaa a                                   31

<210> SEQ ID NO 13
<211> LENGTH: 31
<212> TYPE: DNA
<213> ORGANISM: Artificial
<220> FEATURE:
<223> OTHER INFORMATION: synthetic

<400> SEQUENCE: 13
tggccgggta actacgtgca agtgctacaa a                                   31

<210> SEQ ID NO 14
<211> LENGTH: 1227
<212> TYPE: DNA
<213> ORGANISM: Artificial
<220> FEATURE:
<223> OTHER INFORMATION: synthetic

<400> SEQUENCE: 14
ttataggcct tccaaacgat ccatctgtta ggttgcatga ggctttggga tacacagccc    60
ggggtacatt gcgcgcagct ggatacaagc atggtggatg catgatgtt ggttttttggc   120 aaagggattt tgagttgcca gctcctccaa ggccagttag gccagttacc cagatctgag   180
tcgacctgca ggcatgcccg ctgaaatcac cagtctctct ctacaaatct atctctctct   240
ataataatgt gtgagtagtt cccagataag ggaattaggg ttcttatagg gtttcgctca   300
```

```
tgtgttgagc atataagaaa cccttagtat gtatttgtat ttgtaaaata cttctatcaa    360
taaaatttct aattcctaaa accaaaatcc agggcgagct cgaattcgag ctcgagcccg    420
ggtggatcct ctagagtcga cctgcagaag cttcggtccg gcgcgcctct agttgaagac    480
acgttcatgt cttcatcgta agaagacact cagtagtctt cggccagaat ggcctaactc    540
aaggccatcg tggcctcttg ctcttcagga tgaagagcta tgtttaaacg tgcaagcgct    600
tttgtagcac ttgcacgtag ttacccgact agacaattca gtacattaaa aacgtccgca    660
atgtgttatt aagttgtcta agcgtcaatt tggaacaagt ggctatcgcc agatataaga    720
acttcgatcc gaaatatcgt ttcaaaacta gaaaacagcg cggctttggc taagccgcgc    780
actatatagg attttgggca ccttttgatg gaacgtgaaa gcgtactgcg cactagttat    840
ttaggttgaa ccttggatat acggttctca ctgcgccaat gcaaggcttg aaacttggtt    900
agtaatacgt actccctccg tttcttttta tttgtcgctg gatagtgcaa ttttgcacta    960
tcgagcgaca aataaaaaga aacggaggga gtatatgatt gtcagatgta gatatgttta    1020
tttatatatc acatacagat atataaaaca gatcactttt tcagatatac agttccaatg    1080
tcagccctga tcaccctgtc ataaattgca cgtttctaat tgatgttgct tcatggtcgt    1140
catgagaacc ttctgaagaa atcgatgaag gttgccaacc tttcaaagtt tcagaaacca    1200
ctttgcatgt acactaaggg ctggttt                                       1227
```

<210> SEQ ID NO 15
<211> LENGTH: 27
<212> TYPE: DNA
<213> ORGANISM: Artificial
<220> FEATURE:
<223> OTHER INFORMATION: synthetic

<400> SEQUENCE: 15
cgctactaga caattcagta cattaaa                                        27

<210> SEQ ID NO 16
<211> LENGTH: 24
<212> TYPE: DNA
<213> ORGANISM: Artificial
<220> FEATURE:
<223> OTHER INFORMATION: synthetic

<400> SEQUENCE: 16
atgtactgaa ttgtctagta gcgc                                           24

<210> SEQ ID NO 17
<211> LENGTH: 25
<212> TYPE: DNA
<213> ORGANISM: Artificial
<220> FEATURE:
<223> OTHER INFORMATION: synthetic

<400> SEQUENCE: 17
tacgctgggc cctggaaggc tagga                                          25

<210> SEQ ID NO 18
<211> LENGTH: 25
<212> TYPE: DNA
<213> ORGANISM: Artificial
<220> FEATURE:
<223> OTHER INFORMATION: synthetic

<400> SEQUENCE: 18
gatggacgag acgaggcggt ggaga                                         25

<210> SEQ ID NO 19
<211> LENGTH: 46
<212> TYPE: DNA
<213> ORGANISM: Artificial
<220> FEATURE:
<223> OTHER INFORMATION: synthetic

<400> SEQUENCE: 19
tgcaagcgct tttgtagcac ttgcacgtag ttacccgact agacaa                  46

<210> SEQ ID NO 20
<211> LENGTH: 16779
<212> TYPE: DNA
<213> ORGANISM: Artificial
<220> FEATURE:
<223> OTHER INFORMATION: synthetic

<400> SEQUENCE: 20

| | | | | | |
|---|---|---|---|---|---|
| gagcatatcc | agcaccagct | ggtaccaagg | tcgggtctct | gtgctagtgc | tattagctag | 60 |
| tgtaaggagc | gagtaggtca | gttaaggctg | gtgcgtcgtg | agggctgtct | tgtgtgtagc | 120 |
| tacagcagac | ggttcatcag | aaggattatt | cgtgcagtat | atacagtaca | actagacaat | 180 |
| gatgttgatg | attggtctag | agctagaggc | ctatagccct | atactactgt | gtattgtccg | 240 |
| ccgtttttagt | tttttggtcc | catcccatca | atgcaaccgc | cttgttttgc | tccaattgtc | 300 |
| ccgttcctgc | gcctcgcttt | tgctctgtcg | catcgcatac | aaaaaaaaaa | acgccgcgcc | 360 |
| ggctttgaat | cgcgcccccc | aactgctcca | accaggcaac | ggacacggcc | accgtccgtg | 420 |
| tcgcgagcaa | aaaacaaaa | agaggaacgc | gtccaggacg | aagcagtcca | ctgccgctgt | 480 |
| ggccggcaaa | agatctggtt | gagcacatgg | agattggaga | aggttggttg | gttcttctgg | 540 |
| aaacgccaat | gaatgggggc | actgacatgt | actcttaaca | tgtagtgcaa | tccagagatc | 600 |
| ggatatccag | acactggcag | cacgatcgcc | tcgcgccgta | gatcacgcac | gcaaattact | 660 |
| gaagaccatt | cacaaaaaaa | aaaaaacaca | caggggctag | cgtgccccac | accaaaccca | 720 |
| agtgctgcgt | tgcacgcagg | ggagcgaaaa | aaaacaataa | tgctcactgt | cacgtcgcgt | 780 |
| atccaacccc | gcggacgtct | cggctctcag | cagcagcaca | cggggcacct | cacgatgccg | 840 |
| ttctcgttgc | actccgtgca | ccgccggaac | ccgccgccgc | attcgtcgcc | ctcctcctcc | 900 |
| tcctccgcct | cgtcttcgtc | acccacgtac | accttgcagc | tgcccgagca | gacatcgcag | 960 |
| agcacgaacc | gcatgtcccc | gcaggcctcg | cacgcgccgg | cgtcgccgcc | gtgtgggccg | 1020 |
| gccgtcgacg | cagcgctctc | gcaccggccc | agcctcggcg | cgagctcccc | ggcctcgtgc | 1080 |
| agccgcttca | gctcctcggc | gttgccccacg | agctccccgt | ccacgaagag | gctggggagg | 1140 |
| gcggcgggcg | tgccgccggc | ttggccgagc | ccgaggccga | aaggccgcg | gagctcgtcc | 1200 |
| cggaacccgc | ggtgcatgga | cacgtcgcgc | tcgtcgaggc | gcacgccgta | gcccttgagg | 1260 |
| atggcgcgcg | ccaggcagca | gtcctcgtgc | gtggcgcgca | cgccgcgcag | cgacgtgaag | 1320 |
| tagagcaccg | ccctccgcgg | cggcagcgcc | ttccctccc | cgccgctcgt | cggggcggcg | 1380 |
| tcgggccgag | gcatcggcat | cggcagcggc | gtcaccttgg | cggacgccgc | gaggtcctgc | 1440 |
| gcaggcgccg | tggcgaccgg | gaacgagaag | gagtggcgcc | cgaacggcgc | gcccagcagc | 1500 |
| ggggagcggt | cctcgaggcc | ggccatgagc | gcccacgcgt | cgatgtcctc | gggctcgttg | 1560 |

```
ggcggcgtca tggtgggcgt gcgcggcgcc agcctcgtgg gcgcgggctc cggcgcccgc    1620
ggcagggcct tgtccagctc cagggacccg agcgtggacg acgtgagccg caccacgtgg    1680
acgccgacgt cgctggggca ccgagccggg aacgactggc tgcgcggcag cggtgacggg    1740
cagtaccgga ggtcgtgacg ggcctgcctt gaggtggtgc accccatggc accaatgtac    1800
acacacggcc aaagcgccaa gtgggctgca gactgcctgc caatgtgatc aagcagccag    1860
gagcagagac ggatctctgg ggatcggggt ttctggggtt taggatcttt atactactct    1920
gtcattgggg atataaaact aggagtgtgg ttaattagga ctcgatagat aagtttacca    1980
caagcgcgtg aaatggtcta cccgatgatg tgattggcct aaaaagaaca agaagagtat    2040
ttggagctac tgaacattct cttttcctga agataactaa ttttggaac attcagactt     2100 gggagtctgg acttttggag ggaagttcaa attgtggtct gcctctgcca tgtgttgttt    2160
tttagtcgga gagtggccct catttttttt gtcctgttta gctttatagt cgtagcagct    2220
agtagcgaaa tttaaccttg gattatggcc gtgttagtca aacaatcatt gatttatttc    2280 ctcccttttcg cgctgctttt cctgtacgca tctccgctgc ccttgattcg aggaccctgt   2340
tcacaacaca gggctctggc tttggagcct ctcgtttgta gcacttgcac gtagttaccc    2400
ggaccgaagc ttcaacacag atctgatagt ttaaacgctc ttcaactgga agagcggtta    2460
cccggaccga agcttcggcc ggggcccatc gatatccgcg ggcatgcctg cagtgcagcg    2520
tgacccggtc gtgcccctct ctagagataa tgagcattgc atgtctaagt tataaaaaat    2580
taccacatat ttttttgtc acacttgttt gaagtgcagt ttatctatct ttatacatat     2640
atttaaactt tactctacga ataatataat ctatagtact acaataatat cagtgtttta    2700
gagaatcata taaatgaaca gttagacatg gtctaaagga caattgagta ttttgacaac    2760
aggactctac agttttatct ttttagtgtg catgtgttct cctttttttt tgcaaatagc    2820
ttcacctata taatacttca tccattttat tagtacatcc atttagggtt tagggttaat    2880 ggttttata gactaatttt tttagtacat ctattttatt ctattttagc ctctaaatta     2940
agaaaactaa aactctattt tagtttttttt atttaataat ttagatataa aatagaataa    3000
aataaagtga ctaaaaatta aacaaatacc ctttaagaaa ttaaaaaaac taaggaaaca    3060
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca cccctccac accctctttc cccaacctcg     3420
tgttgttcgg agcgcacaca cacacaacca gatctccccc aaatccaccc gtcggcacct    3480
ccgcttcaag gtacgccgct cgtcctcccc cccccccct ctctaccttc tctagatcgg     3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt ttttgtttc gttgcatagg gtttggtttg     3780 ccctttttcct ttatttcaat atatgccgtg cacttgtttg tcgggtcatc ttttcatgct    3840 ttttttttgtc ttggttgtga tgatgtggtc tggttgggcg gtcgttctag atcggagtag    3900
aattctgttt caaactacct ggtggattta ttaatttttgg atctgtatgt gtgtgccata    3960
```

```
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat ttttttagcc ctgccttcat acgctattta    4440
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg cagattgcc    4620 gttagacatc tccctgtccc ttacacgttt cctgttgtct gagtttgttc caggtgtggg    4680
agttgcgttt ggcctcttcg acctcatctg gggcttcatc actccatctg attggagcct    4740 cttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880 taccccaca acaccattg atccagagag aatcactcag attcccttgg tgaaggcaca    5940
cacacttcag tcaggaacta cagttgtaag agggccgggg ttcacgggag agacattct    6000 tcgacgcact agtggaggac cattcgcgta caccattgtc aacatcaatg gcaacttcc    6060 ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
```

```
caggtttgag ttgattccag ttactgccac actcgagtaa ggatccgtcg acctgcagcc      6360
aagctttcgc gagctcgaga tccccgacat atgccccggt ttcgttgcga ctaacatgag      6420
ttcttggaca aatttgattg gacctgatga gatgatccaa cccgaggata tagcaaagct      6480
cgttcgtgca gcaatggaac ggccaaaccg tgcttttgtc cccaagaatg aggtgctatg      6540
catgaaggaa tctacccgtt gatgtccaac agtctcaggg ttaatgtcta tgtatcttaa      6600
ataatgttgt cggtattttg taatctcata tagattttca ctgtgcgacg caaaatatt      6660 aaataaatat tattattatc tacgttttga ttgagatatc atcaatatta taataaaaat      6720
atccattaaa cacgatttga tacaaatgac agtcaataat ctgatttgaa tatttattaa      6780
ttgtaacgaa ttacataaag atcgaataga aaatactgca ctgcaaatga aaattaacac      6840
atactaataa atgcgtcaaa tatctttgcc aagatcaagc ggagtgaggg cctcatatcc      6900
ggtctcagtt acaagcacgg tatccccgaa gcgcgctcca ccaatgccct cgacatagat      6960
gccgggctcg acgctgagga cattgcctac cttgagcatg gtctcagcgc cggctttaag      7020
ctcaatccca tcccaatctg aatatccat cccgcgccca gtccggtgta agaacgggtc      7080
tgtccatcca cctctgttgg gaattccggt ccgggtcacc tttgtccacc aagatggaac      7140
tgcggccagc ttgcatgcct gcagtgcagc gtgacccggt cgtgcccctc tctagagata      7200
atgagcattg catgtctaag ttataaaaaa ttaccacata ttttttttgt cacacttgtt      7260
tgaagtgcag tttatctatc tttatacata tatttaaact ttactctacg aataatataa      7320
tctatagtac tacaataata tcagtgtttt agagaatcat ataaatgaac agttagacat      7380
ggtctaaagg acaattgagt attttgacaa caggactcta cagttttatc ttttagtgt      7440 gcatgtgttc tccttttttt ttgcaaatag cttcacctat ataatacttc atccatttta      7500
ttagtacatc catttagggt ttaggttaa tggtttttat agactaattt ttttagtaca      7560
tctattttat tctattttag cctctaaatt aagaaaacta aaactctatt ttagtttttt      7620
tatttaataa tttagatata aaatagaata aaataaagtg actaaaaatt aaacaaatac      7680
cctttaagaa attaaaaaaa ctaaggaaac attttttcttg tttcgagtag ataatgccag      7740
cctgttaaac gccgtcgacg agtctaacgg acaccaacca gcgaaccagc agcgtcgcgt      7800
cgggccaagc gaagcagacg gcacggcatc tctgtcgctg cctctggacc cctctcgaga      7860
gttccgctcc accgttggac ttgctccgct gtcggcatcc agaaattgcg tggcggagcg      7920
gcagacgtga gccggcacgg caggcggcct cctcctcctc tcacggcacc ggcagctacg      7980
ggggattcct ttcccaccgc tccttcgctt tcccttcctc gcccgccgta ataaatagac      8040
accccctcca caccctcttt ccccaacctc gtgttgttcg gagcgcacac acacacaacc      8100
agatctcccc caaatccacc cgtcggcacc tccgcttcaa ggtacgccgc tcgtcctccc      8160 ccccccccc tctctaccct tctctagatcg gcgttccggt ccatggttag ggcccggtag      8220
ttctacttct gttcatgttt gtgttagatc cgtgtttgtg ttagatccgt gctgctagcg      8280
ttcgtacacg gatgcgacct gtacgtcaga cacgttctga ttgctaactt gccagtgttt      8340
ctctttgggg aatcctggga tggctctagc cgttccgcag acgggatcga tttcatgatt      8400
ttttttgttt cgttgcatag ggtttggttt gcccttttcc tttatttcaa tatatgccgt      8460
gcacttgttt gtcgggtcat cttttcatgc tttttttgt cttggttgtg atgatgtggt      8520
ctggttgggc ggtcgttcta gatcggagta gaattctgtt tcaaactacc tggtggattt      8580
attaattttg gatctgtatg tgtgtgccat acatattcat agttacgaat tgaagatgat      8640
ggatggaaat atcgatctag gataggtata catgttgatg cgggttttac tgatgcatat      8700
```

```
acagagatgc ttttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060
tttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca agtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgcatgc taatcactat     9660 aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tccccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
```

```
tctcccaact gggagacggg gactgatgtg cagctgcacg tgagctaaat ttttccctat    11100
aaatatgcat gaaatactgc attatcttgc cacagccact gccacagcca gataacaagt    11160
gcagctggta gcacgcaacg catagctctg gacttgtagc taggtagcca accggatcca    11220
cacgacacca tgctcgacac caacaaggtg tacgagatca gcaaccacgc caacggcctc    11280
tacgccgcca cctacctctc cctcgacgac tccggcgtgt ccctcatgaa caagaacgac    11340
gacgacatcg acgactacaa cctcaagtgg ttcctcttcc cgatcgacga cgaccagtac    11400
atcatcacct cctacgccgc caacaactgc aaggtgtgga acgtgaacaa cgacaagatt    11460
aatgtgtcaa cctactcctc caccaactcc atccagaagt ggcagatcaa ggccaacggc    11520
tcctcctacg tgatccagtc cgacaacggc aaggtgctca ccgccggcac cggccaggcc    11580
ctcggcctca tccgcctcac cgacgagtcc tccaacaacc cgaaccagca atggaacctg    11640
acgtccgtgc agaccatcca gctcccgcag aagccgatca tcgacaccaa gctcaaggac    11700
tacccgaagt actccccgac cggcaacatc gacaacggca cctccccgca gctcatgggc    11760
tggaccctcg tgccgtgcat catggtgaac gacccgaaca tcgacaagaa cacccagatc    11820
aagaccaccc cgtactacat cctcaagaag taccagtact ggcagagggc cgtgggctcc    11880
aacgtcgcgc tccgcccgca cgagaagaag tcctacacct acgagtgggg caccgagatc    11940
gaccagaaga ccaccatcat caacaccctc ggcttccaga tcaacatcga cagcggcatg    12000
aagttcgaca tcccggaggt gggcggcggt accgacgaga tcaagaccca gctcaacgag    12060
gagctcaaga tcgagtattc acatgagacg aagatcatgg agaagtacca ggagcagtcc    12120
gagatcgaca acccgaccga ccagtccatg aactccatcg gcttcctcac catcacctcc    12180
ctggagctct accgctacaa cggctccgag atccgcatca tgcagatcca gacctccgac    12240
aacgacacct acaacgtgac ctcctacccg aaccaccagc aggccctgct gctgctgacc    12300
aaccactcct acgaggaggt ggaggagatc accaacatcc cgaagtccac cctcaagaag    12360
ctcaagaagt actacttctg agtcatgagt catgagtcag ttaacctaga cttgtccatc    12420
ttctggattg ccaacttaa ttaatgtatg aaataaaagg atgcacacat agtgacatgc    12480
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccggccgaa gctggccgcg gaccgaattc ccatggagtc aaagattcaa    12780
atagaggacc taacagaact cgccgtaaag actggcgaac agttcataca gagtctctta    12840
cgactcaatg acaagaagaa aatcttcgtc aacatggtgg agcacgacac gcttgtctac    12900
tccaaaaata tcaaagatac agtctcagaa gaccaaaggg caattgagac ttttcaacaa    12960
agggtaatat ccggaaacct cctcggattc cattgcccag ctatctgtca ctttattgtg    13020
aagatagtgg aaaaggaagg tggctcctac aaatgccatc attgcgataa aggaaaggcc    13080
atcgttgaag atgcctctgc cgacagtggt cccaaagatg acccccacc cacgaggagc    13140 atcgtggaaa agaagacgt tccaaccacg tcttcaaagc aagtggattg atgtgatatc    13200
tccactgacg taagggatga cgcacaatcc cactatcctt cgcaagaccc ttcctctata    13260
taaggaagtt catttcattt ggagaggaca gggtacccgg ggatccacca tgtctccgga    13320
gaggagacca gttgagatta ggccagctac agcagctgat atggccgcgg tttgtgatat    13380
cgttaaccat tacattgaga cgtctacagt gaactttagg acagagccac aaacaccaca    13440
```

```
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcataataga aaccettagt atgtatttgt atttgtaaaa tacttctatc    14040
aataaatttt ctaattccta aaaccaaaat ccagggcgag ctcgaattcg agctcgagcc    14100
cgggtggatc tctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
cttttgtagc acttgcacgt agttacccga ctagacaatt cagtacatta aaaacgtccg    14340
caatgtgtta ttaagttgtc taagcgtcaa tttggaacaa gtggctatcg ccagatataa    14400
gaacttcgat ccgaaatatc gtttcaaaac tagaaaacag cgcggctttg gctaagccgc    14460
gcactatata ggattttggg cacctttga tggaacgtga aagcgtactg cgcactagtt    14520
atttaggttg aaccttggat atacggttct cactgcgcca atgcaaggct tgaaacttgg    14580
ttagtaatac gtactccctc cgtttctttt tatttgtcgc tggatagtgc aattttgcac    14640
tatcgagcga caaataaaaa gaaacggagg gagtatatga ttgtcagatg tagatatgtt    14700
tatttatata tcacatacag atatataaaa cagatcactt tttcagatat acagttccaa    14760
tgtcagccct gatcaccctg tcataaattg cacgtttcta attgatgttg cttcatggtc    14820
gtcatgagaa cctttctgaag aaatcgatga aggttgccaa cctttcaaag tttcagaaac    14880
cactttgcat gtacactaag ggctggtttg gcagcccaaa accagccagc gttttcctgg    14940
tcttttctcc cgggagaaag cccatgcata gattgtccct ggattattta tctgtgtcct    15000
ttggctaaaa attcgtccca atttcctgta ggaaactacc tcggccttgg gaggccaggc    15060
gattctccac cgcctcgtct cgtccatcct tcgatgctca cgcgtgcctc ctcggatgct    15120
atcctcaggc gattctccgt cgtctcgtct catccatcct cacgcgcgcc tcctccgacg    15180
ctatccccag gcgattctcc accgtctcgt ctcatccatc ctcatgtacg cctcgtccga    15240
tgctatccc agacgatttt ccgtcgtctc atctccttca tgctcgcgcg cgcctcctcc    15300
gacgctatcc ccaggcgatt tttctgccgt ctcgtctcct tcatgcccgc gcgcgcctcc    15360
tccgacgcta tccccaggcg atttttccgcc gtctcgtctc cttcatgccc gcgcgtgcct    15420
cctccgacgc tattcccacg agcgcctccg ccgccgctat ccccagacga ttttccgctg    15480
tctcgtctcc ttcatgcccg cgcgcccctc ctccgacgct atcccacga gcgcctccgc    15540
cgccgctcca ccgtcttccc cgccgccatc cccttaattc ctatagatct ggaccccgct    15600
ctactttcgt tggcatactt ttgcttggtg tgcgcgggct ggagtggaag gttgcgcatt    15660
cgatcacggg ggagaagtgg atcttgggtc ttggcaggct agggcggttg ccaggacgcc    15720
gtggtgtgca ttcatgggtc ctataaatct ttatcattac cgccttagga gctagttgta    15780
```

-continued

```
gttcacacat catatccttt tctgctcgac atcgtctggg gatgccctag gtgccctacc     15840
gaccctacgg cattgtcttg acctctatta gactctatgt catctagagc cttcttgggt     15900
ggccttttga ccccaaagcg accctatgat cttaccctaa cgaggtctcc cttggtgggg     15960
caagatccac tttgtccact taactgaaga tctgatcctc atcttgaaat ctttaatccc     16020
aaggtgactc tacgtcgtat gtggatgctc cgggtaacct gccaacccgg atcaccctaa     16080
gatctctttc ctaaggggcg agatctaggt tcctacgaga aagaagacga ccctgcacca     16140
ttgcggtccg tccggtccag agtgcgaacg tccggatgcg acacagggaa ggagtcgctc     16200
ctgcagcgag gtcgcagact gtccacacag cctcagaagg caccgccaga caatacatgt     16260
aatacccact ctgtaagaaa aacctaaaag gagaaagtat attcctttat ctatatgtgt     16320
gttatatttc tactcaccat cacatgtgaa catctcactt acacaaataa ataattaaca     16380
aaagacactc aaataaatta tgcatcatgc tcgacccttat tttgtgtgca ttctgttaca     16440
atataaaaat aatataaaaa acatatatta atatcaaaat ttggagattt aaccctaata     16500
tgcaaatcgg agtttagagg aaagaaagaa aaatgctata caaataaag gataaatat      16560 ataaataaag gtaaaactat taatactggt atattaattt gaacagttga cctaattatg     16620
aatatcacaa ctggtttgaa ttcaaatatg aaatccaaga atttggaaat aggaaaaatg     16680
gagataagaa taaaggaaaa gaattcttaa ctcggatggg cctgggaaac gaatttcggc     16740
ccacttcctg tgtccttagc tgtgcggctc agtccagtg                            16779
```

<210> SEQ ID NO 21
<211> LENGTH: 1307
<212> TYPE: PRT
<213> ORGANISM: Unknown
<220> FEATURE:
<223> OTHER INFORMATION: Acidaminococcus sp.

<400> SEQUENCE: 21

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190
```

```
Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
        210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
        290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
        370                 375                 380

Leu Arg Asn Ala Leu Tyr Glu Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
        450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
        530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
            595                 600                 605
```

```
Ser Thr Gln Leu Lys Ala Val Thr Ala His Phe Gln Thr His Thr Thr
610                 615                 620
Pro Ile Leu Leu Ser Asn Asn Phe Ile Glu Pro Leu Glu Ile Thr Lys
625                 630                 635                 640
Glu Ile Tyr Asp Leu Asn Asn Pro Lys Glu Pro Lys Lys Phe Gln
            645                 650                 655
Thr Ala Tyr Ala Lys Lys Thr Gly Asp Gln Lys Gly Tyr Arg Glu Ala
                660                 665                 670
Leu Cys Lys Trp Ile Asp Phe Thr Arg Asp Phe Leu Ser Lys Tyr Thr
            675                 680                 685
Lys Thr Thr Ser Ile Asp Leu Ser Ser Leu Arg Pro Ser Ser Gln Tyr
            690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
                725                 730                 735
Thr Gly Lys Leu Tyr Leu Phe Gln Ile Tyr Asn Lys Asp Phe Ala Lys
                740                 745                 750
Gly His His Gly Lys Pro Asn Leu His Thr Leu Tyr Trp Thr Gly Leu
            755                 760                 765
Phe Ser Pro Glu Asn Leu Ala Lys Thr Ser Ile Lys Leu Asn Gly Gln
770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Lys Leu Lys Asp Gln Lys Thr
                805                 810                 815
Pro Ile Pro Asp Thr Leu Tyr Gln Glu Leu Tyr Asp Tyr Val Asn His
            820                 825                 830
Arg Leu Ser His Asp Leu Ser Asp Glu Ala Arg Ala Leu Leu Pro Asn
            835                 840                 845
Val Ile Thr Lys Glu Val Ser His Glu Ile Ile Lys Asp Arg Arg Phe
850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
            900                 905                 910
Asn Leu Ile Tyr Ile Thr Val Ile Asp Ser Thr Gly Lys Ile Leu Glu
            915                 920                 925
Gln Arg Ser Leu Asn Thr Ile Gln Gln Phe Asp Tyr Gln Lys Lys Leu
            930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                965                 970                 975
His Glu Ile Val Asp Leu Met Ile His Tyr Gln Ala Val Val Val Leu
            980                 985                 990
Glu Asn Leu Asn Phe Gly Phe Lys Ser Lys Arg Thr Gly Ile Ala Glu
            995                 1000                1005
Lys Ala Val Tyr Gln Gln Phe Glu Lys Met Leu Ile Asp Lys Leu
    1010                1015                1020
```

-continued

```
Asn Cys Leu Val Leu Lys Asp Tyr Pro Ala Glu Lys Val Gly Gly
    1025            1030            1035

Val Leu Asn Pro Tyr Gln Leu Thr Asp Gln Phe Thr Ser Phe Ala
    1040            1045            1050

Lys Met Gly Thr Gln Ser Gly Phe Leu Phe Tyr Val Pro Ala Pro
    1055            1060            1065

Tyr Thr Ser Lys Ile Asp Pro Leu Thr Gly Phe Val Asp Pro Phe
    1070            1075            1080

Val Trp Lys Thr Ile Lys Asn His Glu Ser Arg Lys His Phe Leu
    1085            1090            1095

Glu Gly Phe Asp Phe Leu His Tyr Asp Val Lys Thr Gly Asp Phe
    1100            1105            1110

Ile Leu His Phe Lys Met Asn Arg Asn Leu Ser Phe Gln Arg Gly
    1115            1120            1125

Leu Pro Gly Phe Met Pro Ala Trp Asp Ile Val Phe Glu Lys Asn
    1130            1135            1140

Glu Thr Gln Phe Asp Ala Lys Gly Thr Pro Phe Ile Ala Gly Lys
    1145            1150            1155

Arg Ile Val Pro Val Ile Glu Asn His Arg Phe Thr Gly Arg Tyr
    1160            1165            1170

Arg Asp Leu Tyr Pro Ala Asn Glu Leu Ile Ala Leu Leu Glu Glu
    1175            1180            1185

Lys Gly Ile Val Phe Arg Asp Gly Ser Asn Ile Leu Pro Lys Leu
    1190            1195            1200

Leu Glu Asn Asp Asp Ser His Ala Ile Asp Thr Met Val Ala Leu
    1205            1210            1215

Ile Arg Ser Val Leu Gln Met Arg Asn Ser Asn Ala Ala Thr Gly
    1220            1225            1230

Glu Asp Tyr Ile Asn Ser Pro Val Arg Asp Leu Asn Gly Val Cys
    1235            1240            1245

Phe Asp Ser Arg Phe Gln Asn Pro Glu Trp Pro Met Asp Ala Asp
    1250            1255            1260

Ala Asn Gly Ala Tyr His Ile Ala Leu Lys Gly Gln Leu Leu Leu
    1265            1270            1275

Asn His Leu Lys Glu Ser Lys Asp Leu Lys Leu Gln Asn Gly Ile
    1280            1285            1290

Ser Asn Gln Asp Trp Leu Ala Tyr Ile Gln Glu Leu Arg Asn
    1295            1300            1305
```